(12) United States Patent
Chun et al.

(10) Patent No.: US 11,915,796 B2
(45) Date of Patent: Feb. 27, 2024

(54) METHOD FOR CALIBRATING A DATA SET OF A TARGET ANALYTE USING A NORMALIZATION COEFFICIENT

(71) Applicant: SEEGENE, INC., Seoul (KR)

(72) Inventors: Jong Yoon Chun, Seoul (KR); Young Jo Lee, Seoul (KR); Han Bit Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 1554 days.

(21) Appl. No.: 15/777,316

(22) PCT Filed: Nov. 21, 2016

(86) PCT No.: PCT/KR2016/013423
§ 371 (c)(1),
(2) Date: May 18, 2018

(87) PCT Pub. No.: WO2017/086762
PCT Pub. Date: May 26, 2017

(65) Prior Publication Data
US 2018/0336315 A1    Nov. 22, 2018

(30) Foreign Application Priority Data

Nov. 20, 2015 (KR) .................. 10-2015-0163173
Aug. 5, 2016 (KR) .................. 10-2016-0100343

(51) Int. Cl.
*G16B 50/00* (2019.01)
*C12Q 1/686* (2018.01)
*G16B 40/00* (2019.01)
*G16B 40/10* (2019.01)

(52) U.S. Cl.
CPC ............ *G16B 50/00* (2019.02); *C12Q 1/686* (2013.01); *G16B 40/00* (2019.02); *G16B 40/10* (2019.02)

(58) Field of Classification Search
None
See application file for complete search history.

(56) References Cited

U.S. PATENT DOCUMENTS

| | | |
|---|---|---|
| 2013/0115611 A1 | 5/2013 | Gunstream |
| 2014/0030720 A1 | 1/2014 | Gilly et al. |
| 2014/0272991 A1 | 9/2014 | Vijaysri Nair et al. |

OTHER PUBLICATIONS

Barbany, Gisela, et al. "Manifold-assisted reverse transcription—PCR with real-time detection for measurement of the BCR-ABL fusion transcript in chronic myeloid leukemia patients." Clinical Chemistry 46.7 (2000): 913-920.*
Roberts, A. M., et al.; "Calibration of Quantitative PCR Assays", American Statistical Association and the International Biometric Society Journal of Agricultural, Biological, and Environmental Statistics. vol. 12, No. 3, pp. 364-378, 2007.
Burns, M. J., et al.; "Standardisation of data from real-time quantitative PCR methods—evaluation of outliers and comparison of calibration curves", BMC Biotechnology, 5:31, 2005, pp. 1-13.
International Search Report from corresponding PCT Application No. PC/KR2016/013423, dated Feb. 14, 2017.

* cited by examiner

*Primary Examiner* — G. Steven Vanni
(74) *Attorney, Agent, or Firm* — Harness, Dickey & Pierce, P.L.C.

(57) ABSTRACT

The present invention relates to a method for calibrating a data set of a target analyte in a sample, wherein a normalization coefficient for calibrating the data set is provided by using a reference value, a reference cycle and the data set, and the calibrated data set is obtained by applying the normalization coefficient to the signal values of the data set. The present method is very effective in removing the inter- and intra-instrument signal variations of data sets. Furthermore, since the present method can be configured in software, the instant method is capable of being applied universally to various analytical instruments (e.g., a real-time PCR instrument) regardless of manufacturer. Accordingly, the method by the present invention would be very useful in diagnostic data analysis.

24 Claims, 35 Drawing Sheets

1) RFU represents relative fluorescence units.

1) AC represents the analytical cycle. The signal values at the analytical cycle of all the data sets are analyzed together.

1) RFU represents relative fluorescence units.

1) AC represents the analytical cycle. The signal values at the analytical cycle of all the data sets are analyzed together.

1) RFU represents relative fluorescence units.

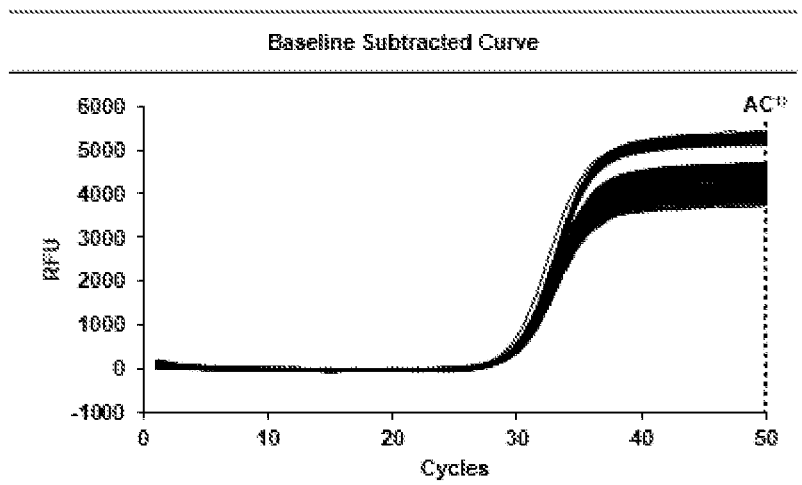

Baseline Subtracted Curve

RFU: Relative Fluorescence units

Analytical result of the data set with data normalization by SBN[2].

|  | Instrument 1 | Instrument 2 | Instrument 3 | Total |
|---|---|---|---|---|
| Min. | 3747 | 4178 | 5097 | 3747 |
| Max. | 4183 | 4729 | 5414 | 5414 |
| Range | 436 | 551 | 318 | 1668 |
| Mean | 3983 | 4465 | 5297 | 4582 |
| SD | 91 | 134 | 55 | 553 |
| CV (%) | 2.3% | 3.0% | 1.0% | 12.1% |

Min.: Minimum; Max.: Maximum; Range : Max-Min; SD: Standard Deviation; CV: Coefficient of variation 1) AC represents the analytical cycle. The signal values at the analytical cycle of all the data sets are analyzed together.

2) SBN represents the specific background signal based normalization

FIG. 4B

1) RFU represents relative fluorescence units.

1) AC represents the analytical cycle. The signal values at the analytical cycle of all the data sets are analyzed together.

2) SBN represents the specific background signal based normalization

1) RFU represents relative fluorescence units.

1) AC represents the analytical cycle. The signal values at the analytical cycle of all the data sets are analyzed together.

2) SBN represents the specific background signal based normalization

3) Instrument-specific reference value represent the reference value derived from standard data set of each instrument 1) RFU represents relative fluorescence units.

1) AC represents the analytical cycle. The signal values at the analytical cycle of all the data sets are analyzed together.

2) SBN represents the specific background signal based normalization

3) Instrument-specific reference value represent the reference value derived from standard data set of each instrument 1) RFU represents relative fluorescence units.

1) AC represents the analytical cycle. The signal values at the analytical cycle of all the data sets are analyzed together.

2) SBN represents the specific background signal based normalization

3) Instrument-specific reference value represent the reference value derived from standard data set of each instrument 1) RFU represents relative fluorescence units.

1) AC represents the analytical cycle. The signal values at the analytical cycle of all the data sets are analyzed together.

2) SBN represents the specific background signal based normalization

3) Instrument-specific reference value represent the reference value derived from standard data set of each instrument 1) RFU represents relative fluorescence units.

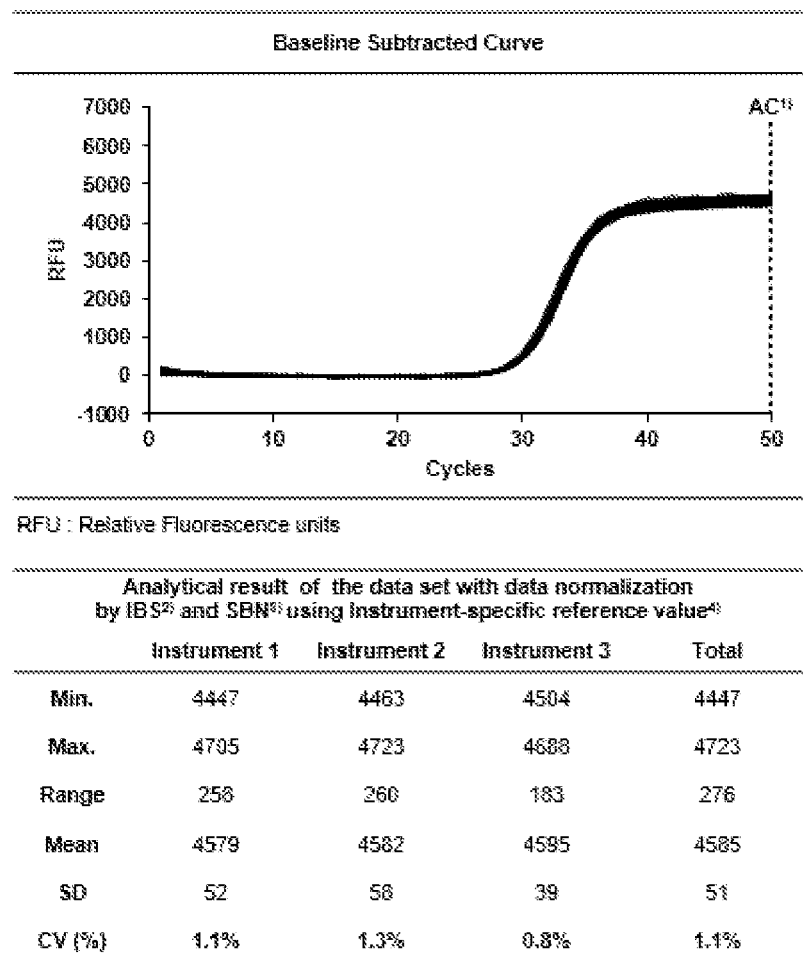

1) AC represents the analytical cycle. The signal values at the analytical cycle of all the data sets are analyzed together.

2) IBS represents the instrument blank signal subtraction

3) SBN represents the specific background signal based normalization

4) Instrument-specific reference value represent the reference value derived from standard data set of each instrument.

FIG. 10B

1) RFU represents relative fluorescence units.

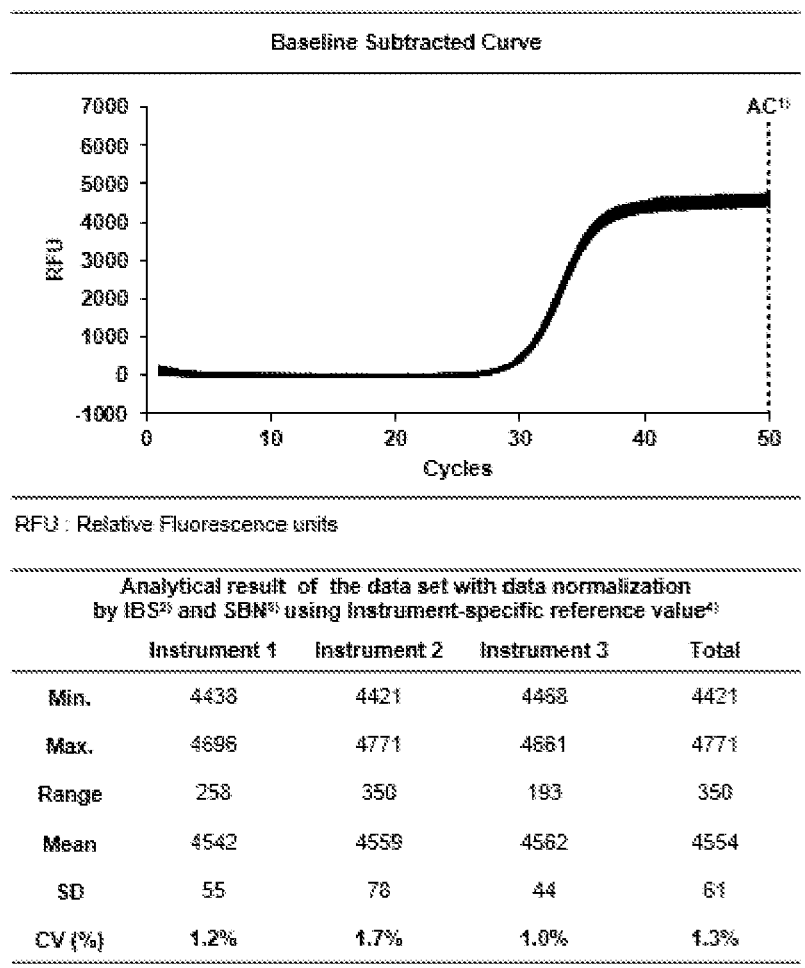

1) AC represents the analytical cycle. The signal values at the analytical cycle of all the data sets are analyzed together.

2) IBS represents the instrument blank signal subtraction

3) SBN represents the specific background signal based normalization

4) Instrument-specific reference value represent the reference value derived from standard data set of each instrument.

FIG. 11B

1) RFU represents relative fluorescence units.

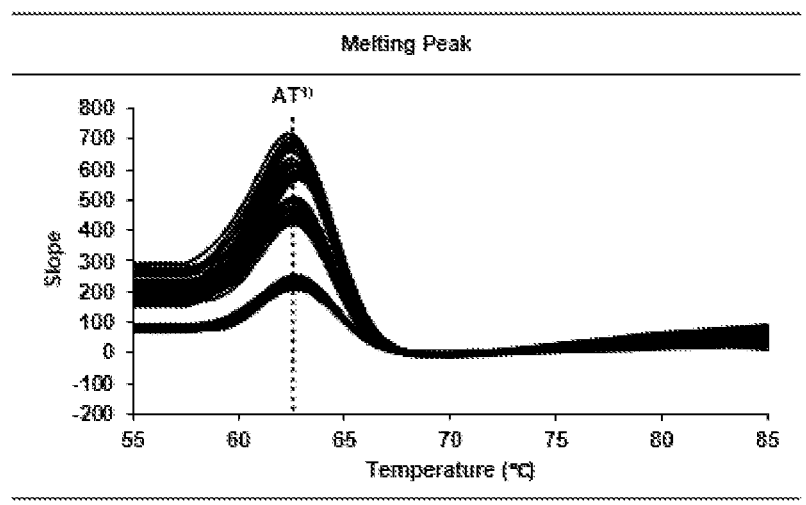

Slope: The change of relative fluorescence unit at each temperature

| | Analytical result of the melting data set without hardware adjustment or data normalization. | | | |
|---|---|---|---|---|
| | Instrument 1 | Instrument 2 | Instrument 3 | Total |
| Min. | 206 | 421 | 566 | 206 |
| Max. | 250 | 506 | 713 | 713 |
| Range | 44 | 85 | 147 | 507 |
| Mean | 227 | 467 | 623 | 439 |
| SD | 11 | 27 | 47 | 166 |
| CV (%) | 4.9% | 5.9% | 7.5% | 37.8% |

Min.: Minimum; Max.: Maximum; Range : Max-Min; SD: Standard Deviation; CV: Coefficient of variation 1) AT represents the analytical temperature. The signal values at the analytical temperatures of all the data sets are analyzed together.

FIG. 12B

1) RFU represents relative fluorescence units.

1) AT represents the analytical temperature. The signal values at the analytical temperatures of all the data sets are analyzed together.

1) RFU represents relative fluorescence units.

1) AT represents the analytical temperature. The signal values at the analytical temperatures of all the data sets are analyzed together.

2) IBS represents the instrument blank signal subtraction

3) SBN represents the specific background signal based normalization.

1) AT represents the analytical temperature. The signal values at the analytical temperatures of all the data sets are analyzed together.

2) IBS represents the instrument blank signal subtraction

3) SBN represents the specific background signal based normalization.

1) RFU represents relative fluorescence units.

1) AT represents the analytical temperature. The signal values at the analytical temperatures of all the data sets are analyzed together.

2) IBS represents the instrument blank signal subtraction

3) SBN represents the specific background signal based normalization.

1) RFU represents relative fluorescence units.

1) AT represents the analytical temperature. The signal values at the analytical temperatures of all the data sets are analyzed together.

2) IBS represents the instrument blank signal subtraction

3) SBN represents the specific background signal based normalization.

1) RFU represents relative fluorescence units.

1) AT represents the analytical temperature. The signal values at the analytical temperatures of all the data sets are analyzed together.

2) IBS represents the instrument blank signal subtraction

3) SBN represents the specific background signal based normalization.

1) RFU represents relative fluorescence units.
2) IBS represents the instrument blank signal subtraction
   SBN represents the specific background signal based normalization.
3) End-RFU represents relative fluorescence units at 50th cycle.
4) Threshold is used to determine the Ct value.

METHOD FOR CALIBRATING A DATA SET OF A TARGET ANALYTE USING A NORMALIZATION COEFFICIENT

FIELD OF THE INVENTION

The present invention relates to a method for calibrating a data set of a target analyte in a sample.

BACKGROUND OF THE INVENTION

A polymerase chain reaction (hereinafter referred to as "PCR") which is most widely used for the nucleic acid amplification includes repeated cycles of denaturation of double-stranded DNA, followed by oligonucleotide primer annealing to the DNA template, and primer extention by a DNA polymerase (Mullis et al., U.S. Pat. Nos. 4,683,195, 4,683,202 and 4,800,159; Saiki et al., (1985) Science 230, 1350-1354) A real-time polymerase chain reaction is one of PCR-based technologies for detecting a target nucleic add molecule in a sample in a real-time manner. For detecting a specific target analyte, the real-time PCR uses a signal-generating means for generating a fluorescence signal being detectable in a proportional manner with the amount of the target molecule. The generation of fluorescence signals may be accomplished by using either intercalators generating signals when intercalated between double-stranded DNA or oligonucleotides carrying fluorescent reporter and quencher molecules. The fluorescence signals whose intensities are proportional with the amount of the target molecule are detected at each amplification cycle and plotted against amplification cycles, thereby obtaining an amplification curve or amplification profile curve.

A sample analysis using fluorescence signals is performed as follow. When a luminant is supplied with energy through a light source such as LED, electron of the luminant is excited to a higher quantum state, then the luminant emits a light of specific wavelength by relaxation of the orbital electron to its ground state. Analytical instrument converts the light of specific wavelength to an electric signal using photodiode or CCD and provides information needed for sample analysis. Although the same amount of a luminant in a sample is analyzed, each analytical instrument provides different signal values because of the uneven illuminations of the light source (e.g., LED) and the performance variations of the light-electricity conversion device in the respective instruments. Such a signal difference between instruments is called as an inter-instrument variation. In addition to the inter-instrument variation, the analysis results of a plurality of reactions performed for the same kind and the same amount of the target analyte by a single identical analytical instrument may have variations in signal level because of the difference in reaction environments such as the position of reaction well where the reaction is performed on the instrument or delicate differences in composition or concentration of the reaction mixture. Such a signal difference among the reactions in a single instrument is known as an intra-instrument variation. Furthermore, an electrical noise signal is generated by an analytical instrument Itself even when a blank (matrix without analyte) is analyzed and it may be identified as a normal signal. However, such an electrical noise signal also creates a signal variation and is referred to as an instrument blank signal. The instrument blank signal is generated in a manner that a specific amount of signal value is added to or subtracted from the original signal value for each cycle.

For the precise and reliable analysis, such problems have to be solved and several methods are used to solve the problems. As a most basic solution, a hardware adjustment method is used. For instance, when the analytical instrument is manufactured, the property of some parts of each analytical instrument such as intensity of LED light source is calibrated or adjusted such that the level of an inter-instrument variation for the same sample is reduced and maintained within a proper range. Alternatively, a reference dye method may be used. The reference dye such as ROX™ or fluorescein which constantly generates a known amount of a signal is added in a reaction mixture such that the signal generated from a sample is calibrated based on the level of signal generated from the reference dye.

However, these prior art may have some limitations or shortcomings. The hardware adjustment method shows limited accuracy in calibration and an additional calibration is needed to remove a variation occurred by deterioration of the analytical instrument. Furthermore, the hardware adjustment method can reduce only the inter-instrument variation but cannot reduce the intra-instrument variation. The signal calibration using the reference dye increases the cost per reaction and the quantitative and qualitative variations in the reference dyes used in each reaction may cause another error. Furthermore, the use of the reference dye may increase the possibility of interference phenomenon between the reference dye and other dyes used for determining the presence of target analyte in the reaction mixture. The interference phenomenon is a very important problem, particularly in the multiplex PCR where multiple dyes are used and their fluorescence have to be detected. Besides, assigning one dye and one detection channel for the signal calibration causes a considerable disadvantage in view of the product competitiveness because it results in one less targets simultaneously detectable.

Accordingly, there are strong needs in the art to develop novel approaches for calibrating the data set and reducing the inter- and intra-instrument variations without direct adjusting of hardware or using the reference dye.

Throughout this application, various patents and publications are referenced and citations are provided in parentheses. The disclosure of these patents and publications in their entirety are hereby incorporated by references into this application in order to more fully describe this invention and the state of the art to which this invention pertains.

SUMMARY OF THE INVENTION

The present inventors have made intensive researches to develop novel approaches for obtaining more accurate and reliable calibration results of signal variations in a plurality of data sets wherein the variations are the inter-instrument and the intra-instrument variations of signals obtained from the instruments for acquiring data sets (e.g., real-time PCR system).

As a result, we have found that a calibrated data set can be obtained with accuracy and reliability when a normalization coefficient is provided by using an arbitrarily determined reference value, a reference cycle and the data set and is applied to the signal values of the plurality of data points. Furthermore, we have also found that the calibrated data set can be obtained with higher accuracy and reliability when an instrument blank signal value is removed from the signal value of the data set before the normalization coefficient is provided. Moreover, we have found that the calibrated data set can be obtained with higher accuracy and reliability when the reference value is determined upon consideration of an inter-instrument variation.

Accordingly, it is an object of this invention to provide a method for calibrating a data set of a target analyte in a sample.

It is another object of this invention to provide a computer readable storage medium containing instructions to configure a processor to perform a method for calibrating a data set of a target analyte in a sample.

It is still another object of this invention to provide a device for analyzing a method for calibrating a data set of a target analyte in a sample.

It is further object of this invention to provide a computer program to be stored on a computer readable storage medium to configure a processor, to perform a method for calibrating a data set of a target analyte in a sample.

Other objects and advantages of the present invention will become apparent from the detailed description to follow taken in conjugation with the appended claims and drawings.

BRIEF DESCRIPTION OF THE DRAWINGS

FIG. 4b represents baseline subtracted amplification curves of calibrated data sets obtained by calibration of three groups of raw data sets by the SBN using a common reference value, wherein the raw data sets are obtained respectively from three instruments without a hardware adjustment and analytical results of the inter- and the intra-instrument coefficient of variation of the calibrated data sets.

FIG. 10b represents baseline subtracted amplification curves of calibrated data sets obtained by calibration of three groups of raw data sets by the IBS-SBN using an instrument-specific reference value, wherein the raw data sets are obtained respectively from three instruments without a hardware adjustment and analytical results of the inter- and the intra-instrument coefficient of variation of the calibrated data sets.

FIG. 11b represents baseline subtracted amplification curves of calibrated data sets obtained by calibration of three groups of raw data sets by the IBS-SBN using an instrument-specific reference value, wherein the raw data sets are obtained respectively from three instruments with a hardware adjustment and analytical results of the inter- and the intra-instrument coefficient of variation of the calibrated data sets.

FIG. 12b represents melting peaks obtained by plotting the derivatives of the raw melting data sets obtained respectively from three instruments without a hardware adjustment and analytical results of the inter- and the intra-instrument coefficient of variation of maximum derivatives of the data sets.

DETAILED DESCRIPTION OF THIS INVENTION

I. Method for Calibrating a Data Set of a Target Analyte

In one aspect of this invention, there is provided a method for calibrating a data set of a target analyte in a sample comprising:

(a) providing a normalization coefficient for calibrating the data set; wherein the data set is obtained from a signal-generating process for the target analyte using a signal-generating means; wherein the data set comprises a plurality of data points comprising cycles of the signal-generating process and signal values at the cycles; wherein the normalization coefficient is provided by using a reference value, a reference cycle and the data set; wherein the reference cycle is selected from the cycles of the data set; wherein the reference value is an arbitrarily determined value; wherein the normalization coefficient is provided by defining a relationship between the reference value and a signal value at a cycle of the data set corresponding to the reference cycle; and (b) providing a calibrated data set by obtaining calibrated signal values by applying the normalization coefficient to the signal values of the data set.

The present inventors have made intensive researches to develop novel approaches for calibrating a data set and more effectively reducing the inter- and intra-instrument variation among a plurality of data sets which represent the presence or absence of target analyte, for instance target nucleic acid molecule. As results, we have found that the calibrated data set can be obtained with accuracy and reliability by providing a normalization coefficient by using a reference value, a reference cycle and a data set and applying the normalization coefficient to the signal values of the plurality of data points.

According to an embodiment, this approach is named herein as "Specific Background signal based Normalization (SBN)" method, because a specific background signal of a specific cycle i.e., a reference cycle in background region is used for a calibration.

The term used herein "normalization" refers to a process of reducing or eliminating a signal variation of a data set obtained from a signal-generating process. The term used herein "calibration" or "adjustment" refers to a correction of a data set, particularly a correction of a signal value of a data set, suitable for the aim of analysis. The normalization is one aspect of the calibration.

Figure 1:
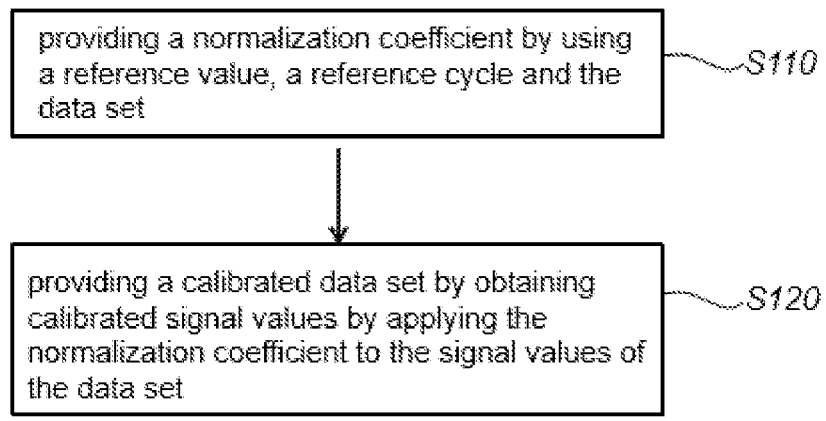
FIG. 1 represents a flow diagram illustrating an embodiment of the present method for calibrating a data set of a target analyte in a sample.

FIG. 1 represents a flow diagram illustrating an embodiment of the present method for calibrating a data set of a target analyte in a sample according to the SBN method. The present invention will be described in more detail as follows:

Step (a): Providing a Normalization Coefficient for Calibrating a Data Set(110)

According to the present method, a normalization coefficient for calibrating a data set is provided. The data set is obtained from a signal-generating process for a target analyte using a signal-generating means, and the data set comprises a plurality of data points comprising cycles of the signal-generating process and signal values at the cycles.

The terms used herein a target analyte may include various materials (e.g., biological materials and non-biological materials such as chemicals). Particularly, the target analyte may include biological materials such as nucleic acid molecules (e.g., DNA and RNA), proteins, peptides, carbohydrates, lipids, amino adds, biological chemicals, hormones, antibodies, antigens, metabolites and cells. More particularly, the target analyte may include nucleic acid molecules. According to an embodiment, the target analyte may be a target nucleic add molecule.

The term used herein "sample" may include biological samples (e.g., cell, tissue and fluid from a biological source) and non-biological samples (e.g., food, water and soil). The biological samples may include virus, bacteria, tissue, cell, blood (e.g., whole blood, plasma and serum), lymph, bone marrow aspirate, saliva, sputum, swab, aspiration, milk, urine, stool, vitreous humour, sperm, brain fluid, cerebrospinal fluid, joint fluid, fluid of thymus gland, bronchioalveolar lavage, ascites and amnion fluid. When a target analyte is a target nucleic acid molecule, the sample is subjected to a nucleic acid extraction process. When the extracted nucleic add is RNA, reverse transcription process is performed additionally to synthesize cDNA from the extracted RNA (Joseph Sambrook, et al., *Molecular Coning, A Laboratory Manual*, Cold Spring Harbor Laboratory Press, Cold Spring Harbor, N.Y. (2001)).

The term used herein "signal-generating process" refers to any process capable of generating signals in a dependent manner on a property of a target analyte in a sample, wherein the property may be, for instances, activity, amount or presence (or absence) of the target analyte, in particular the presence of (or the absence of) an analyte in a sample. According to an embodiment, the signal-generating process generates signals in a dependent manner on the presence of the target analyte in the sample.

Such signal-generating process may include biological and chemical processes. The biological processes may include genetic analysis processes such as PCR, real-time PCR, microarray and invader assay, immunoassay processes and bacteria growth analysis. According to an embodiment, the signal-generating process includes genetic analysis processes. The chemical processes may include a chemical analysis comprising production, change or decomposition of chemical materials. According to an embodiment, the signal-generating process may be a PCR or a real-time PCR.

The signal-generating process may be accompanied with a signal change. The term "signal" as used herein refers to a measurable output. The signal change may serve as an indicator indicating qualitatively or quantitatively the property, in particular the presence or absence of a target analyte. Examples of useful indicators include fluorescence intensity, luminescence intensity, chemiluminescence intensity, bioluminescence intensity, phosphorescence intensity, charge transfer, voltage, current, power, energy, temperature, viscosity, light scatter, radioactive intensity, reflectivity, transmittance and absorbance. The most widely used indicator is fluorescence intensity. The signal change may include a signal decrease as well as a signal increase. According to an embodiment, the signal-generating process is a process amplifying the signal values.

The term used herein "signal-generating means" refers to any material used in the generation of a signal indicating a property, more specifically the presence or absence of the target analyte which is intended to be analyzed.

A wide variety of the signal-generating means have been known to one of skill in the art. Examples of the signal-generating means may include oligonucleotides, labels and enzymes. The signal-generating means include both labels per se and oligonucleotides with labels. The labels may include a fluorescent label, a luminescent label, a chemiluminescent label, an electrochemical label and a metal label. The label per se like an intercalating dye may serve as signal-generating means. Alternatively, a single label or an interactive dual label containing a donor molecule and an acceptor molecule may be used as signal-generating means in the form of linkage to at least one oligonucleotide. The signal-generating means may comprise additional components for generating signals such as nucleolytkic enzymes (e.g., 5'-nucleases and 3'-nucleases).

Where the present method is applied to determination of the presence or absence of a target nucleic add molecule, the signal-generating process may be performed in accordance with a multitude of methods known to one of skill in the art. The methods include TaqMan™ probe method (U.S. Pat. No. 5,210,015), Molecular Beacon method (Tyagi et al., Nature Biotechnology, 14 (3):303 (1996)), Scorpion method (Whitcombe et al., Nature Biotechnology 17:804-807 (1999)), Sunrise or Amplifluor method (Nazarenko et al, Nucleic Adds Research, 25(12):2516-2521 (1997), and U.S. Pat. No. 6,117,635), Lux method (U.S. Pat. No. 7,537,886), CPT (Duck P, et al, Biotechniques, 9:142-148 (1990)), LNA method (U.S. Pat. No. 6,977,295), Plexor method (Sherrill C B, et al., Journal of the American Chemical Society, 126: 4550-4556 (2004)), Hybeacons™ (D. J. French, et al., Molecular and Cellular Probes (2001) 13, 363-374 and U.S. Pat. No. 7,348,141), Dual-labeled, self-quenched probe (U.S. Pat. No. 5,876,930), Hybridization probe (Bernard P S, et al, Clin Chem 2000, 46, 147-148), PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (PCT/KR2013/012312) and CER method (WO 2011/037306).

The term used herein "amplification" or "amplification reaction" refers to a reaction for increasing or decreasing signals. According to an embodiment of this invention, the amplification reaction refers to an increase (or amplification) of a signal generated depending on the presence of the target analyte by using the signal-generating means. The amplification reaction is accompanied with or without an amplification of the target analyte (e.g., nucleic acid molecule). Therefore, according to an embodiment of this invention, the signal-generating process is performed with or without an amplification of the target nucleic acid molecule. More particularly, the amplification reaction of present invention refers to a signal amplification reaction performed with an amplification of the target analyte.

The data set obtained from an amplification reaction comprises an amplification cycle.

The term used herein "cycle" refers to a unit of changes of conditions or a unit of a repetition of the changes of conditions in a plurality of measurements accompanied with changes of conditions. For example, the changes of conditions or the repetition of the changes of conditions include changes or repetition of changes in temperature, reaction time, reaction number, concentration, pH and/or replication number of a measured subject (e.g., target nucleic add molecule). Therefore, the cycle may include a condition (e.g., temperature or concentration) change cycle, a time or a process cycle, a unit operation cycle and a reproductive cycle. A cycle number represents the number of repetition of the cycle. In this document, the terms "cycle" and "cycle number" are used interchangeably.

For example, when enzyme kinetics is investigated, the reaction rate of an enzyme is measured several times as the concentration of a substrate is increased regularly. In this reaction, the increase in the substrate concentration may correspond to the changes of the conditions and the increasing unit of the substrate concentration may be corresponding to a cycle. For another example, when an isothermal amplification of nucleic add is performed, the signals of a single sample are measured multiple times with a regular interval of times under isothermal conditions. In this reaction, the reaction time may correspond to the changes of conditions and a unit of the reaction time may correspond to a cycle. According to another embodiment, as one of methods for detecting a target analyte through a nucleic add amplification reaction, a plurality of fluorescence signals generated from the probes hybridized to the target analyte are measured with a regular change of the temperature in the reaction. In this reaction, the change of the temperature may correspond to the changes of conditions and the temperature may correspond to a cycle.

Particularly, when repeating a series of reactions or repeating a reaction with a time interval, the term "cycle" refers to a unit of the repetition. For example, in a polymerase chain reaction (PCR), a cycle refers to a reaction unit comprising denaturation of a target nucleic acid molecule, annealing (hybridization) between the target nucleic acid molecule and primers and primer extension. The increases in the repetition of reactions may correspond to the changes of conditions and a unit of the repetition may correspond to a cycle.

According to an embodiment, where the target nucleic add molecule is present in a sample, values (e.g., Intensities) of signals measured are increased or decreased upon increasing cycles of an amplification reaction. According to an embodiment, the amplification reaction to amplify signals indicative of the presence of the target nucleic add molecule may be performed in such a manner that signals are amplified simultaneously with the amplification of the target nucleic add molecule (e.g., real-time PCR). Alternatively, the amplification reaction may be performed in such a manner that signals are amplified with no amplification of the target nucleic add molecule [e.g., CPT method (Duck P, et al., Biotechniques, 9:142-148 (1990)), Invader assay (U.S. Pat. Nos. 6,358,691 and 6,194,149)].

The target analyte may be amplified by various methods. For example, a multitude of methods have been known for amplification of a target nucleic acid molecule, including, but not limited to, PCR (polymerase chain reaction), LCR (ligase chain reaction, see U.S. Pat. No. 4,683,195 and No. 4683202; A Guide to Methods and Applications (Innis et al., eds, 1990); Wiedmann M, et al., "Ligase chain reaction (LCR)—overview and applications." PCR Methods and Applications 1994 February; 3(4):S51-64), GLCR (gap filling LCR, see WO 90/01069, EP 439182 and WO 93/00447), Q-beta (Q-beta replicase amplification, see Cahill P, et al., Clin Chem., 37(9):1482-5 (1991), U.S. Pat. No. 5,556,751), SDA (strand displacement amplification, see G T Walker et al., Nucleic Adds Res. 20(7):1691-1696 (1992), EP 497272), NASBA (nucleic add sequence-based amplification, see Compton, J. Nature 350(6313):91-2 (1991)), TMA (Transcription-Mediated Amplification, see Hofmann W P et al., J Clin Virol. 32(4):289-93 (2005); U.S. Pat. No. 5,888,779).) or RCA (Rolling Circle Amplification, see Hutchison C. A. et al., Proc. Natl Acad. Sci. USA. 102:17332-17336 (2005)).

According to an embodiment, the label used for the signal-generating means may comprise a fluorescence, more particularly, a fluorescent single label or an interactive dual label comprising donor molecule and acceptor molecule (e.g., an interactive dual label containing a fluorescent reporter molecule and a quencher molecule).

According to an embodiment, the amplification reaction used in the present invention may amplify signals simultaneously with amplification of the target analyte, particularly the target nucleic acid molecule. According to an embodiment, the amplification reaction is performed in accordance with a PCR or a real-time PCR.

The data set obtained from a signal-generating process comprises a plurality of data points comprising cycles of the signal-generating process and signal values at the cycles.

The term used herein "values of signals" or "signal values" means either values of signals actually measured at the cycles of the signal-generating process (e.g., actual value of fluorescence intensity processed by amplification reaction) or their modifications. The modifications may include mathematically processed values of measured signal values (e.g., intensities). Examples of mathematically processed values of measured signal values may include logarithmic values and derivatives of measured signal values. The derivatives of measured signal values may include multi-derivatives.

The term used herein "data point" means a coordinate value comprising a cycle and a value of a signal at the cycle. The term used herein "data" means any information comprised in data set. For example, each of cycles and signal values of an amplification reaction may be data. The data points obtained from a signal-generating process, particularly from an amplification reaction may be plotted with coordinate values in a rectangular coordinate system. In the rectangular coordinate system, the X-axis represents cycles of the amplification reaction and the Y-axis represents signal values measured at each cycles or modifications of the signal values.

The term used herein "data set" refers to a set of data points. The data set may include a raw data set which is a set of data points obtained directly from the signal-generating process (e.g., an amplification reaction) using a signal-generating means. Alternatively, the data set may be a modified data set which is obtained by a modification of the data set including a set of data points obtained directly from the signal-generating process. The data set may include an entire or a partial set of data points obtained from the signal-generating process or modified data points thereof.

According to an embodiment of this invention, the data set may be a mathematically processed data set of the raw data set. In particular, the data set may be a baseline subtracted data set for removing a background signal value from the raw data set. The baseline subtracted data set may be obtained by methods well known in the art (e.g., U.S. Pat. No. 8,560,240).

The term "raw data set" as used herein refers to a set of data points (including cycle numbers and signal values) obtained directly from an amplification reaction. The raw data set means a set of non-processed data points which are initially received from a device for performing a real-time PCR (e.g., thermocycler, PCR machine or DNA amplifier). In an embodiment of the present invention, the raw data set may include a raw data set understood conventionally by one skilled in the art. In an embodiment of the present invention, the raw data set may include a dataset prior to processing. In an embodiment of the present invention, the raw data set may include a dataset which is the basis for the mathematically processed data sets as described herein. In an embodiment of the present invention, the raw data set may include a data set not subtracted by a baseline (no baseline subtraction data set).

The method of the present invention may be a method for calibrating a single data set of a target analyte in a sample. Alternatively, the method for present invention may be a method for calibrating a plurality of data sets. According to an embodiment, a data set of the present invention may comprise a plurality of data sets. Particularly, the plurality of data sets is a plurality of data sets of same-typed target analytes.

According to an embodiment, the data set of step (a) may be a data set which is removed of an instrument blank signal. Alternatively, the data set of step (a) may be the data set which is not removed of an Instrument blank signal.

The term "$1^{st}$ calibrated data set" may be used herein in order to refer to the modified data set in which an instrument blank signal is removed from the raw data set. The $1^{st}$ calibrated data set may be interpreted as a modified data set and is distinguished from the finally calibrated data set or the $2^{nd}$ calibrated data set.

According to an embodiment, the instrument blank signal may be obtained by no use of the signal-generating means. Particularly, the instrument blank signal is a signal detected from a reaction performed without signal-generating means such as labels per se, or labeled oligonucleotides which generate a signal by the presence of the target analyte. Because such instrument blank signal is measured in the absence of the signal-generating means, a signal variation due to an instrument-to-instrument difference in ratios of signals generated per unit concentration of target analytes is not applied to the instrument blank signal.

The instrument blank signal may be determined and applied in various approaches. For example, the separate instrument blank signals may be determined for applying to their corresponding instruments. A single instrument blank signal may be applied to data sets obtained by a single instrument and different instrument blank signals each may be applied to the data sets obtained each of their corresponding instruments. Alternatively, different instrument blank signals each may be determined for applying to each of wells within a single instrument. Each well within a single instrument may have its own instrument blank signal and different instrument blank signals each may be applied to data sets obtained by each of their corresponding wells within a single instrument.

The data set which is removed of an instrument blank signal may be the data set in which an instrument blank signal is removed in whole or in part. The term of "removal" means subtracting or adding a value of signal from/to a data set. Particularly, the term "removal" refers to subtraction of a value of signal from a data set. When an instrument blank signal has a negative value, it may be removed by adding a value of signal.

According to an embodiment, the instrument blank signal may be obtained by no use of the signal-generating means. Particularly, the instrument blank signal may be measured using an empty well, an empty tube, a tube containing water or a tube containing a real-time PCR reaction mixture without signal-generating means such as fluorescence molecule conjugated oligonucleotide. A measurement of an instrument blank signal may be performed together with a signal-generating process or may be performed separately from a signal-generating process.

According to an embodiment, an instrument blank signal may be removed in whole in such a manner that measurement of the instrument blank signal is performed together with a signal-generating process and the measured instrument blank signal is subtracted from signal values of a data set obtained by the signal-generating process.

Alternatively, an instrument blank signal may be removed in part in such a manner that a certain value of a signal is subtracted from signal values of a data set obtained by a signal-generating process. The certain value of a signal may be any value so long as a signal corresponding to an instrument blank signal in a data set is reduced by the subtraction of the certain value of signal. For instance, the certain value of a signal may be determined based on a plurality of instrument blank signals measured from one instrument or a plurality of instruments. When it is troublesome to measure an instrument blank signal for each target analyte analysis experiment, an instrument blank signal may be removed from data sets in such a manner that a certain value of signal corresponding to a portion of the instrument blank signal is determined based on a plurality of instrument blank signals measured from one instrument or from a plurality of instruments and then the determined certain value of signal is subtracted from each of data sets.

Alternatively, the certain value of signal may be determined in such a range that a signal variation of a data set is reduced when the certain value of signal is subtracted from the data set and the signal values of the subtracted data set are calibrated with ratio according to the present method. As such, the data set reduced of an instrument blank signal may be provided by subtracting the certain value of signal which is a portion of the instrument blank signal without measurement of an instrument blank signal for each reaction.

According to an embodiment, the method further comprises the step of performing the signal-generating process to obtain a data set of the target analyte in the sample before the step (a).

According to an embodiment, the data set of the target analyte may indicate the presence or absence of the target analyte in the sample. In this case, the method provided by the present invention is described as "a method for calibrating data set representing the presence or absence of a target analyte in a sample". The calibration of a data set representing the presence or absence of a target analyte in a sample is performed to eventually for determining the presence or absence of a target analyte in a sample. The term used "determining the presence or absence of an analyte in a sample" means determining qualitatively or quantitatively the presence or absence of an analyte in a sample.

According to an embodiment, the normalization coefficient may be provided by using a reference value, a reference cycle and the data set.

The reference cycle is selected from the cycles of the data set. The reference value is an arbitrarily determined value. The normalization coefficient is provided by defining a relationship between the reference value and a signal value at a cycle of the data set corresponding to the reference cycle.

The reference cycle is a cycle selected for determining a specific signal value used for providing a normalization coefficient with a reference value. The reference cycle used for providing a normalization coefficient may be selected arbitrarily from cycles of the data set.

The reference cycle may encompass a reference temperature, a reference concentration or a reference time depending on the meaning of the cycle. For instance, a reference temperature may be a reference cycle of melting data set, wherein the unit of cycle is temperature. In the description regarding melting data set, the terms "reference cycle" and "reference temperature" may be used interchangeably.

According to an embodiment, the reference cycle is selected from a reference cycle group of each data set, wherein the reference cycle group of each data set is provided in the same manner to each other.

According to an embodiment, the reference cycle is selected from a reference cycle group of each data set, wherein the reference cycle group is generated based on an identical rule. The identical rule may be applied equally to the determination of the reference cycle in all data sets.

The reference cycle group of each data set is provided in the same manner to each other. The reference cycle group may be determined by various approaches. For example, the reference cycle group may comprise the cycles at which a similar level of signal values is measured. The reference cycle group may comprise the cycles at which a substantially identical level of signal values is measured. The reference cycle group may comprise the cycles where the coefficient of variation of signal values is within 5%, 6%, 7%, 8%, 9%, 10%.

When the data set is plotted as a sigmoidal response shape, the reference cycle group may comprise the cycles before and/dr after the amplification region (i.e., growth phase). The region before the amplification region may be baseline region or early stage region. The region after the amplification region may be the plateau region or late stage region. The reference cycle group may comprise a single cycle wherein the number of the single cycle of each data set is identical to one another.

The number of the reference cycle(s) determined in each data set may be identical to one another. Alternatively, the number of the reference cycle(s) determined in each data set may be different from one another.

According to an embodiment, the plurality of data sets is calibrated by using a reference cycle or cycles selected from a reference cycle group which is provided in the same manner (a common rule or a pre-determined criterion) to each other.

According to an embodiment, the same manner (a common rule or a pre-determined criterion) provides a reference group, wherein the normalization coefficients calculated from a data set with the reference cycle or cycles selected from the reference group may be substantially identical or in a range of narrow standard deviation (e.g. 15%, 10%, 8%, 5% or 4%).

According to an embodiment, when the data set comprises the plurality of data sets, an identical reference cycle is applied to a plurality of data sets to be analyzed with regard an identical criterion. According to an embodiment, the plurality of data sets is calibrated by using an identical reference cycle.

The signal variation of data sets used for intra or inter-comparison analysis or analyzed by the identical criterion such as the same threshold need to be minimized. A range of data sets to be analyzed with regard to an identical criterion may be determined by a purpose of analysis, such as, but not limited thereto, a plurality of data sets obtained from a target analyte, obtained from the same type of sample, or obtained by the same reaction mixture (e.g., the same fluorescent molecules or same probe) may be analyzed with regard to an identical criterion.

However, according to an embodiment, when the data set comprises a plurality of data sets, at least two data sets of the plurality of data sets are applied with different reference cycles from each other so long as the signal values of the different reference cycles are substantially identical.

Because a reference cycle is used for determining a specific signal value which is used for providing a normalization coefficient together with a reference value, the reference cycle would be selected from cycles of data set where the cycles are capable of providing a signal value.

The reference cycle may be a pre-determined cycle or may be determined by an experiment. The reference cycle may be selected from cycles of a data set. Specifically, the reference cycle is selected from cycles in a region of a data set where amplification of signal is not sufficiently detected.

For example, when the data set is obtained by a nucleic acid amplification process, it is preferable that the reference cycle is selected within a background signal region. The background region refers to ah early stage of a signal-generating process before amplification of signal is sufficiently detected.

The background region may be determined by various approaches. For instance, the end-point cycle of the background region may be determined with a cycle of the first data point having a slope more than a certain threshold in the first derivatives of the data set obtained by a nucleic acid amplification process. Alternatively, the start-point cycle of the background region may be determined with a starting cycle of the first peak in the first derivatives of the data set obtained by a nucleic acid amplification process. Otherwise, the end-point cycle of the background region may be determined with a cycle of a data point having a maximum curvature.

According to an embodiment, the amplification process of the signal value may be a process providing signal values of a background signal region and a signal amplification region and the reference cycle may be selected within the background signal region. More specifically, according to an embodiment, the signal-generating process may be a polymerase chain reaction (PCR) or a real-time polymerase chain reaction (real-time PCR) and the reference cycle may be selected within the background signal region before a signal amplification region of the polymerase chain reaction (PCR) or the real-time polymerase chain reaction (real-time PCR). The signal values of initial background region of data sets obtained by a plurality of PCRs or real-time PCRs using the same target analyte under the same reaction condition would have theoretically the same or at least similar value, because the signal values of initial background region may comprise very low level of the signal value generated by target analyte regardless of the concentration of the target analyte. Therefore, it is preferable that the reference cycle is selected within the background signal region.

Therefore, the number of the reference cycles may be not more than 50, 40, 30, 25, 20, 19, 18, 17, 16, 15, 14, 13, 12, 11, 10, 9 or 8. The reference cycle of the present invention may be selected with avoiding an initial noise signal. The number of the reference cycles may be not less than 0, 1, 2, 3, 4, 5, 6 or 7. Particularly, the reference cycle of the present invention may be determined from cycles 1-30, 2-30, 2-20, 2-15, 2-10, 2-8, 3-30, 3-20, 3-15, 3-10, 3-9, 3-8, 4-8, or 5-8 in the background region.

According to an embodiment, the reference cycle may be a single reference cycle. A single cycle may be used as a reference cycle, and a signal value at the reference cycle of a data set may be used for providing a normalization coefficient. Alternatively, according to an embodiment, the reference cycle may comprise at least two reference cycles.

The reference cycle may comprise at least two reference cycles and the signal values at the cycles of the data set corresponding to the reference cycles may comprise at least two signal values.

A normalization coefficient for calibration may be provided by using a signal value which is calculated from the respective signal values at the cycles of the data set corresponding to the at least two reference cycles. Alternatively, at least two normalization coefficients may be provided by using the respective signal values at the cycles of the data set corresponding to the at least two reference cycles, and a normalization coefficient for calibration may be provided from the at least two normalization coefficients. For example, $4^{th}$, $5^{th}$ and $6^{th}$ cycles may be designated as reference cycles, and the average of the signal values of $4^{th}$, $5^{th}$ and $6^{th}$ cycles of a data set may be used for providing a normalization coefficient. For another example, the $4^{th}$, $5^{th}$ and $6^{th}$ cycles may be designated as the reference cycles and the normalization coefficients for each reference cycle may be provided by using the respective signal values at the cycles of the data set corresponding to the reference cycles, and then the average of the provided normalization coefficients may be determined as the final normalization coefficient to be applied to the data set.

According to an embodiment, when a reference cycle is selected within a range of cycles of a data set, the reference cycle s selected from the cycles at which the signal values of the data sets to be analyzed with regard to an identical criterion would have the same value or at least similar value at the reference cycle.

A signal value used for providing a normalization coefficient to be applied to a plurality of data points for the calibration of a data set is determined by a reference cycle and the data set. Particularly, the normalization coefficient is provided by defining a relationship between the reference value and a signal value at a cycle of the data set corresponding to the reference cycle.

According to an embodiment, the method of present invention may further comprises the step of removing abnormal signals (e.g., spike signal or jump error) from a data set obtained by signal-generating process before the determination of the signal value used for providing a normalization coefficient from the reference cycle and the data set.

A reference value is a value used for providing a normalization coefficient. A reference value of the present invention refers to an arbitrary value that is applied to a reference cycle for the calibrations of signal values of a data set. The data sets to be analyzed by an identical criterion may be applied with the same reference value. When the data set to be calibrated is a plurality of data sets, the plurality of data sets may be calibrated by using an identical reference value and this is one of the important features of the embodiment of the present invention.

A reference value may be an arbitrarily determined value. Preferably, the reference value may be an arbitrarily determined value from a real number except zero. When the reference value is zero, the normalization coefficient cannot be determined. As used herein, "a reference value may be an arbitrarily determined value" means that a reference value may be determined non-limitedly so long as the presence of a target analyte in a sample is determined by the calibrated data set using the reference value. The reference value may be selected arbitrarily by an experimenter so long as the presence of a target analyte in a sample is determined by the calibrated data set using the reference value. Therefore, the reference value to be used for calibrating a data set may be determined within a range of signal values to be obtained at the reference cycle of the same-typed signal-generating processes as a signal-generating process by which the data set is obtained. The reference value may be obtained separately from a data set to be calibrated. Specifically, the reference value may be determined by a data set which is obtained from a signal-generating process of the same-typed of target analyte to a target analyte to be analyzed. Alternatively, the reference value may be obtained from a group of data sets comprising a data set to be calibrated.

Preferably, a reference value may be the same-typed value as the values of a data set to be calibrated and may have the same unit or dimension as the data set to be calibrated. However, even though the reference value and the signal value of the data set may have different units or dimensions from each other or the reference value has no unit or dimension, a proper normalization coefficient for each reaction may be provided using a ratio of the reference value to the signal value of the data set to be calibrated, such that a calibrated data set may be obtained using the normalization coefficient for each reaction.

According to an embodiment, the signal-generating process may be a plurality of signal-generating processes for the detection of the same type of target analytes, the data set may be a plurality of data sets and a reference values applied to each data set may be determined independently from another reference value. The expression used herein "the reference values may be determined independently" means that a reference value for a data set of the plurality of data sets may be determined without consideration of a reference value for another data set. Accordingly, when the data set of present invention comprises the plurality of data sets, at least two data sets of the plurality of data sets may be calibrated by using different reference values from each other or all of the data set may be calibrated by using an identical reference value.

The plurality of signal-generating processes may be a plurality of signal-generating processes for the detection of the same type of target analytes (i.e., the same-typed target analytes). The same type of target analytes may be a plurality of target analytes isolated from the same sample. Alternatively, the same type of target analytes may be a plurality of target analytes which is isolated from the different samples but detected by the same signal-generating means (e.g., the same probes or same primers).

According to an embodiment, the plurality of signal-generating processes may be a plurality of signal-generating processes for the same-typed target analyte performed in different reaction environments. Signal-generating processes in different reaction environments comprise various embodiments. Particularly, the signal-generating processes in different reaction environments may be a signal-generating processes performed on different instruments, performed in different wells or reaction tubes, performed for different samples, performed with target analytes of different concentrations, performed with different primers or probes, performed with different signal-generating dyes or performed by different signal-generating means.

According to an embodiment, the signal-generating process may comprise a plurality of signal-generating processes performed in different reaction vessels, and the data set may comprise a plurality of data sets obtained from the plurality of signal-generating processes. The plurality of signal-generating processes may be performed in different reaction vessels. The term used herein "reaction vessel" refers to a vessel or a portion of a device at which a reaction is processed by mixing a sample and signal-generating means (e.g., primers or probes). The expression used herein "the plurality of signal-generating processes may be performed in different reaction vessels" means that a signal-generating process is performed using a signal-generating means and a sample that are separated from another signal-generating means and sample for another signal-generating process. For example, the signal-generating processes performed in a plurality of tubes or In a plurality of wells of a plate may correspond to the plurality of signal-generating processes. The signal-generating processes which are performed in the same reaction vessel but in different times also may correspond to the plurality of signal-generating processes.

The plurality of signal-generating processes may be classified into several groups with regard to reaction environments (e.g., an instrument used). Particularly, the plurality of signal-generating processes performed in different instruments may be classified into different groups depending on the instruments performed. The plurality of data sets obtained from signal-generating processes which were performed in different instruments may be calibrated by using an identical reference value or may be calibrated by using different reference values for more fine calibration.

According to an embodiment, the plurality of signal-generating processes may be performed on different instruments from each other. When the instrument analyzes a single sample at one operation, the plurality of data sets obtained from this type of the plurality of signal-generating processes may be calibrated by using different reference values each other.

According to an embodiment, the plurality of data sets may be calibrated by using an identical reference value. According to an embodiment, the plurality of data sets may be calibrated by using an identical reference cycle.

When a plurality of data sets is calibrated by using an identical reference value (common reference value) which is applied to the plurality of data sets in common, all of the data sets are calibrated to have an identical signal value at a reference cycle, thereby reducing the signal variation of the data sets. Therefore, the normalization coefficients for data sets obtained from a plurality of signal-generating processes which is different in reaction environments may be obtained by using an identical reference value, which is one of the important features of the embodiment of the present invention. Particularly, each normalization coefficient for the data sets obtained from a plurality of signal-generating processes which is different in reaction environments may be obtained by using an identical reaction cycle and an identical reference value. According to an embodiment, the plurality of data sets obtained from different instruments may be calibrated by using an identical reference value.

According to an embodiment, the reference value is determined within the average f standard deviation (SD) of signal values at the cycles of the plurality of data sets corresponding to the reference cycle. When the reference value is determined within the range described above, a plurality of data sets may be normalized with minimizing the difference between the data set and the calibrated data set.

However, the plurality of data sets may be calibrated by using different reference values. Different reference values may be applied to a plurality of data sets to be analyzed by an identical criterion. According to an embodiment, at least two data sets of the plurality of data sets may be calibrated by using different reference values from each other.

The plurality of data sets may be classified into several groups with regard to reaction environments (e.g., an instrument used), and by considering differences of the reaction environments, a reference value appropriated each group may be determined and applied. Through this process, the signal variation among the plurality of data sets may be calibrated more precisely.

Where all of the plurality of the data sets may be classified into respective different groups from one another, a respective reference value is applied to each of the all data sets. When at least two data sets of the plurality of data sets may be classified into a group, a respective reference value is applied to each of the at least two data sets. For example, the data sets obtained in different wells within an instrument may be classified into the same group and the data sets obtained from different instruments may be classified into different groups. According to an embodiment, the different reference values may be applied to the data sets obtained using different instruments and the same reference value may be applied to the data sets obtained in different wells within an instrument. According to an embodiment, at least two data sets of the plurality of data sets may be calibrated by using different reference values from each other wherein the at least two data sets may be obtained using different instruments from each other.

According to an embodiment, the signal-generating process may be a plurality of signal-generating processes for the same type of target analyte performed in different reaction vessels, the data set may comprise a plurality of data sets obtained from the plurality of signal-generating processes, and at least two data sets of the plurality of data sets are calibrated by using different reference values from each other. For instance, to calibrate an inter-instrument signal variation more precisely, an instrument-specific standard data set of each instrument and its total signal change value may be obtained and then a reference value to be applied to a data set obtained by using a corresponding instrument may be determined using the total signal change value, which is another feature of the embodiment of the present invention.

The inter-instrument variation may be a signal variation between the separate data sets which are obtained by the signal-generating processes for the identical target analyte performed on the respective different instruments. Alternatively, the inter-instrument variation may be a signal variation between the separate data sets which are obtained by independent operations of the signal-generating processes for the identical target analyte on the identical instrument. For example, the independent operations of the signal-generating processes for the identical target analyte may be performed on the identical instrument with an operation time interval. In this case, the independent operation of an instrument may be considered as an instrument.

According to an embodiment, even though at least two data sets of the plurality of data sets may be calibrated by using different reference values, the at least two data sets of the plurality of data sets may be calibrated by using an identical reference cycle.

According to an embodiment, the reference value is determined by (i) a ratio of a total signal change value of a standard data set to a reference total signal change value; wherein the standard data set is obtained by using a reaction site which is identical to that used for obtaining the data set from the signal-generating process for the target analyte; wherein the reference total signal change value is determined by one or more data sets comprising a data set obtained from a signal-generating process using a reaction site which is different from that used for obtaining the data set from the signal-generating process for the target analyte and (ii) the standard data set. Particularly, a signal value at a reference cycle of a standard data set may be calibrated using a ratio of a total signal change value of a standard data set to a reference total signal change value, followed by determining a reference value from the signal value at the reference cycle of the calibrated standard data set.

A reference value may be determined using a reference total signal change value and a total signal change value of a standard data set.

According to an embodiment, the standard data set is obtained by using a reaction site which is identical to that used for obtaining the data set from the signal-generating process for the target analyte.

The reaction site is a physical space in which a process dr a reaction of the sample is performed. The reaction site may include an instrument (e.g., PCR instrument) and a part of an instrument (e.g., reaction well configured in PCR instrument). The reaction site is configured for a target analyte detection e.g., the PCR amplification.

The standard data set may be a data set obtained by performing a signal-generating process for a target analyte of known concentration. The standard data set may be obtained using an identical well(s) or instrument to that for obtaining the data set from the signal-generating process for the target analyte.

According to an embodiment, the standard data set may be obtained separately from a data set of a target analyte to be calibrated. When a calibration ratio for an instrument is calculated based on a standard data set obtained using the instrument, a signal-generating process for the standard data set is not necessarily performed by a reaction under the same conditions as reaction conditions by which a data set of a target analyte in a sample is obtained.

According to another embodiment, the standard data set may be obtained together with the data set of the target analyte to be calibrated. The standard data set may be obtained by a reaction performed under the same reaction conditions as reaction conditions by which a data set of a target analyte in a sample is obtained. A fine calibration for compensating a signal variation found in each instrument run may be achieved.

Since the standard data set is a data set for a target analyte of known concentration, the standard data set can be used for determining a reference value by comparative analysis of the common factors between the standard data set and another data set for a target analyte of the same concentration as the known concentration. Specifically, the target analyte of known concentration may be a target analyte of a standard concentration. The common factors may be those which theoretically have constant values when an identical signal-generating process is performed under an identical condition. The common factor may be, for instance, a total signal change value, a cycle number of a first data point having a signal value more than a threshold or a signal value at a cycle in baseline region.

According to an embodiment, the data set may be calibrated by using a total signal change value as one of the common factor. The term used herein "total signal change value" means a signal change amount (increased or decreased) of the data set. The total signal change value may be a signal change amount (increased or decreased) of the entire data set or may be a signal change amount (increased or decreased) of a partial region of the data set. For example, the total signal change value may be a signal change value at the cycle having the greatest signal change value. Particularly, the total signal change value may be a difference between a signal value of baseline and a maximum signal value of the data set or a difference between a signal value of baseline and a signal value of the last cycle of the data set.

Meanwhile, when the total signal change value is determined within a region of the data set, the total signal change value may be a difference between the first cycle and the last cycle of the region of the data set or a difference between the maximum signal value and the minimum signal value of the region of the data set. Constant total signal change values may be obtained theoretically from the same or different instruments when signal-generating processes are performed using target analytes of an identical concentration under an identical condition. Therefore, the calibration based on the total signal change value may reduce a variation between a plurality of the data sets.

A reference total signal change value refers to a total signal change value used in determining a normalization coefficient in comparison with a total signal change value of a standard data set.

According to an embodiment, the reference total signal change value is may be determined by one or more data sets comprising a data set obtained from a signal-generating process using the reaction site which is different from that used for obtaining the data set from the signal-generating process for the target analyte.

Specifically, the reference total signal change value may be determined by the data set obtained from a signal-generating process using the reaction site which is different from that used for obtaining the data set from the signal-generating process for the target analyte together with the data set obtained from a signal-generating process using the reaction site which is identical to that used for obtaining the data set from the signal-generating process for the target analyte.

More specifically, the reference total signal change value may be determined by the data set obtained from a signal-generating process using the reaction site which is different from that used for obtaining the data set from the signal-generating process for the target analyte.

The reference total signal change value may be a total signal change value obtained separately from the standard data set.

According to an embodiment, the reference total signal change value may be a pre-determined total signal change value. The reference total signal change value may be obtained by using a reference (or standard) vessel(s) or instrument(s) with substantially identical standard material use used for obtaining the total change value of the standard data set.

The reference total signal change value of the present invention may be determined by a data set obtained from a signal-generating process for the target analyte of known concentration. Alternatively, the reference total signal change value of the present invention may be calculated from total signal change values of a plurality of data sets obtained from a plurality of signal-generating processes for the target analyte of known concentration. In this case, the reference total signal change value is an average or median value of a plurality of data sets obtained from a plurality of signal-generating processes for the target analyte of known concentration or may be predetermined by an experimenter based on the results of a plurality of signal-generating processes for the target analyte of known concentration.

Alternatively, according to an embodiment, when the standard data set is a plurality of standard data sets, the reference total signal change value may be determined from the plurality of standard data sets. For instance, one of the total signal change values of the plurality of standard data sets may be determined as a reference total signal change value. Alternatively, an average or median value of the total signal change values of the plurality of standard data sets may be determined as a reference total signal change value.

According to an embodiment, the reference value may be determined within a range of a plurality of signal values at reference cycles of a plurality of data sets to be analyzed with regard to an identical criterion. When the reference value is determined within a range of a plurality of signal values at reference cycles of a plurality of data sets to be analyzed with regard to an identical criterion, the plurality of data sets may be calibrated with minimizing difference between the data set and the calibrated data set.

According to an embodiment, the normalization coefficient for a data set may be provided by using a reference value and a reference cycle and the data set. More particularly, the normalization coefficient may be provided by using a reference value and a signal value at a cycle of the data set to be calibrated wherein the cycle is corresponding to the reference cycle. The normalization coefficient may be a value applied to a plurality of data points of a data set obtained from a reaction, thereby calibrating the data set.

When the data set comprises the plurality of data sets, the plurality of data sets may be obtained from the plurality of signal-generating processes in different reaction vessels. The normalization coefficient may be provided for each data set of the plurality of data sets. The plurality of data sets may be calibrated by applying the normalization coefficients. For reducing signal variation shown between data sets to be analyzed by an identical criterion, the normalization coefficient appropriate to the data set is provided by the present method. The normalization coefficient is applied to signal values at a plurality of data points of the data set, thereby obtaining calibrated signal values to provide a calibrated data set.

The normalization coefficient may be provided by using a reference value, a reference cycle and the data set. The normalization coefficient may be provided by defining a relationship between the reference value and a signal value at a cycle of the data set corresponding to the reference cycle. The relationship between the reference value and a signal value at a cycle of the data set corresponding to the reference cycle may be defined by various ways, for example, the relationship may be defined mathematically. The signal value at the cycle of the data set corresponding to the reference cycle (i.e., at the reference cycle-corresponding cycle of the data set) may be a signal value without modification or may be a signal value modified mathematically. Particularly, the relationship between the reference value and a signal value at a cycle of the data set corresponding to the reference cycle may be a difference between the reference value and a signal value at the cycle of the data set corresponding to the reference cycle. More particularly, the difference between the reference value and a signal value at the cycle of the data set corresponding to the reference cycle may be a ratio of the signal value at the cycle of the data set corresponding to the reference cycle to the reference value.

The cycle of the data set corresponding to the reference cycle is a reference cycle-corresponding cycle of the data set. According to an embodiment, the signal value of a reference cycle-corresponding cycle of the data set may be a single signal value. Alternatively, according to an embodiment, the signal value of a reference cycle-corresponding cycle of the data set may be a plurality of signal values.

The normalization coefficient may be provided by defining a relationship between the reference value and a signal value or by defining a relationship between the reference value and a plurality of signal values. The plurality of signal values may be obtained at a reference cycle or a plurality of reference cycles.

When the normalization coefficient is provided by a reference value and a signal value at the reference cycle-corresponding cycle of the data set, the normalization coefficient may be provided by a ratio of the signal value at the reference cycle-corresponding cycle of the data set to the reference value.

When the normalization coefficient is provided by a reference value and a plurality of signal values at the reference cycle-corresponding cycles of the data set, the plurality of signal values at the reference cycle-corresponding cycle of the data set may be designated by a plurality of reference cycles or a reference cycle.

For example, when $3^{rd}$ cycle is designated as a reference cycle, the plurality of signal values at the reference cycle-corresponding cycle may comprise a signal value at $3^{rd}$ cycle and signal values at the cycles which are positioned one cycle before/after the $3^{rd}$ cycle. For another example, when $2^{rd}$, $3^{rd}$ and $4^{th}$ cycles are designated as reference cycles, the plurality of signal values at the reference cycle-corresponding cycle may comprise signal values at $2^{nd}$, $3^{nd}$ and $4^{th}$ cycle which are the reference cycle-corresponding cycles.

The relationship between the plurality of signal values designated by reference cycle(s) and a reference value may be defined by various ways. For example, the relationship between the plurality of signal values and a reference value may be defined by a ratio of an average, median, minimum or maximum value of the plurality of signal values or an average value of threshold-below signal values of the plurality of signal values to the reference value. Preferably, the relationship between the plurality of signal values designated by reference cycle(s) and a reference value may be defined by a ratio of an average value of the plurality of signal values to the reference value. When the plurality of signal values is used to provide the normalization coefficient, the influence of an abnormal signal value on calibration of a data set becomes negligible.

For example, when a signal value at the reference cycle-corresponding cycle of the data set is 0 (zero), all of the calibrated signal values of the data set may have the same value. The occurrence of such erroneous result may be much more reduced by using a plurality of signal values for providing the normalization coefficient than by using a single signal value. According to an embodiment, when a normalization coefficient is 0 (zero), all or some of signal values for providing the normalization coefficient may be changed to other signal values.

According to an embodiment, the normalization coefficient is provided by using a reference value and a signal value at the reference cycle-corresponding cycle of the data set.

The normalization coefficient may be calculated by following mathematical equation:

[Normalization coefficient=a signal value at the cycle of the data set corresponding to the reference cycle/reference value]

For instance, the normalization coefficient may be calculated as 1.48, when a data set obtained by performing a real-time PCR for detection of a target analyte is calibrated on conditions that (a) the $5^{th}$ cycle is designated as a reference cycle; (b) the value of 9000 is designated as a reference value; (c) the signal value at the cycle of the data set corresponding to the reference cycle is the value of 13,285 and (d) the relationship between the signal value at the reference cycle-corresponding cycle of the data set and the reference value is a ratio of the signal value at the reference cycle-corresponding cycle of the data set to the reference value. A calibrated data set may be provided by obtaining calibrated signal values by applying the normalization coefficient (1.48) to the signal values of the plurality of data points.

According to an embodiment, the normalization coefficient may be provided by defining a ratio of a signal value at the reference cycle-corresponding cycle of the data set to the reference value. The normalization coefficient may be calculated by following mathematical equation:

[Normalization coefficient=α×(a signal value at the cycle of the data set corresponding to the reference cycle/reference value)].

The α may be a real number except for 0 (zero), preferably, may be the number of 1. The α is a constant for adjusting a normalization coefficient property when the reference value is determined dependent on other factors. A signal level of a reaction may be controllable through calibration of signal values of a data set with adjusting the reference value or the value of a, thereby controlling an amount of a reaction mixture used for signal-generating process.

All of data points of a data set may be calibrated by using an identical normalization coefficient in accordance with an identical mathematical equation. Alternatively, all or a portion of data points of a data set may be calibrated by using different normalization coefficients respectively or by using an identical normalization coefficient in accordance with different mathematical equations.

Step (b): Providing a Calibrated Data Set by Applying a Normalization Coefficient (S120)

A calibrated data set may be provided by obtaining calibrated signal values by applying the normalization coefficient to the signal values of the data set. Particularly, a calibrated data set may be provided by obtaining calibrated signal values by applying the normalization coefficient to the signal values of the plurality of data points.

The normalization coefficient may be applied to the signal values of the data set by various approaches.

When the normalization coefficient is provided by the ratio of the signal value at the reference cycle-corresponding cycle of the data set to the reference value, a calibrated data set may be provided by obtaining calibrated signal values.

According to an embodiment, the calibrated signal value is obtained by using the following mathematical equation 1:

Calibrated signal value=signal value/normalization coefficient     Equation 1

The signal value of equation 1 is uncalibrated signal value. The uncalibrated signal value refers to a signal value of a data set before the data set is calibrated by the normalization coefficient. Therefore, the uncalibrated signal value may be a measured signal value or a processed signal value of the measured signal value. The process may be a process performed independently from a calibration process using the normalization coefficient. For example, the signal value processing may be performed by adding or subtracting a certain amount of value to or from the signal value. Particularly, the process may be removing an instrument blank signal in whole or in part from the measured signal value.

The calibrated signal value refers to a signal value calibrated by the normalization coefficient. The calibrated data set may be provided by using the calibrated signal value for the signal value of the data set without further calibration.

Alternatively, the calibrated data set may be provided by using the calibrated signal value for the signal value of the data set with further modification. For instance, the signal value calibrated by the normalization coefficient may be further calibrated by adding or subtracting a certain amount of value to or from the calibrated signal value. Particularly, the signal value calibrated by the normalization coefficient may be further calibrated by subtracting baseline signal value.

According to an embodiment, the calibrated data set is used for qualitative or quantitative detection of the target analyte in the sample.

According to an embodiment, the data set of the present invention may be obtained from a signal-generating process for the target analyte using a signal-generating means without a reference dye, which is one of the features of the embodiment of the present invention. According to a conventional technology a reference dye is contained in a reaction mixture for calibration (see WO2012/083235). This prior art may have some limitations or shortcomings.

Introducing the reference dye into a reaction mixture may increase the possibility of an interference phenomenon between the reference dye and other) dyes used for determining the presence of target analyte. In contrast, the present invention can calibrate a data set without introducing the reference dye into a reaction mixture comprising signal-generating means.

In the method of the present invention, the data set is capable of being calibrated by using the signal value of a target analyte without introducing the reference dye into a reaction mixture comprising signal-generating means, whereby it is possible to calibrate the data set more precisely and effectively than conventional method using the reference dye together with signal-generating means and to overcome various issues associated with variations in analytical results.

In Example described below, the CVs (coefficient of variation) of the inter- and intra-Instrument variations of two groups of data sets were calculated and compared. The data sets of group 1 were obtained by calibrating raw data sets according to the method of the present invention wherein the raw data sets were obtained by a real-time PCR using three instruments without a hardware adjustment. The data sets of group 2 were obtained by the same real-time PCR using three instruments with a hardware adjustment.

Furthermore, the CVs of the inter- and intra-instrument variations of two groups of melting data sets were calculated and compared. The melting data sets of group 1 were obtained by calibrating raw melting data sets according to the method of the present invention wherein the raw melting data sets were obtained by performing a melting analysis using products of a real-time PCR using three instruments without a hardware adjustment. The melting data sets of group 2 were obtained by performing a melting analysis using products of a real-time PCR using three instruments with a hardware adjustment.

As a result, it was verified that the CVs (coefficient of variation) of the inter- and intra-instrument variations of the data sets or the melting data sets of group 1 is much smaller than those of the data sets or the melting data sets of group 2. As such, it would be understood that the method of the present invention may be an alternative solution of a hardware adjustment not only for an amplification data set but also for a melting data set.

Meanwhile, according to the method of the present invention, a level of signal values of a data set may be controlled by modulating the reference value. As a result, a normalized data set with statistical significance and may be obtained even when a small amount of signal-generating means (e.g., primers and probes) is used, finally determining the presence or absence of a target analyte in a sample.

According to an embodiment, the reference value may be selected to be higher than a maximum signal value of a baseline of the data set; wherein the signal-generating process may be a plurality of signal-generating processes for the same-typed target analyte performed in different reaction environments; wherein the data set is a plurality of data sets; wherein the plurality of data sets is calibrated by using an identical reference cycle and an identical reference value.

The reference value may be selected to be higher than a maximum signal value of a baseline of the data set such that the ratio of the reference value to a maximum signal value of a baseline of the data set may become, not limited to, 1.1, 1.2, 1.3, 1.4, 1.5, 1.6, 1.7, 1.8, 1.9, 2, 3, 4, 5, 6, 7, 8, 9, 10, 15, 20, 30, 40, 50, 60, 70, 80, 90, 100, 200, 300, 400, and 500.

Interestingly, we have found that the present invention can minimize a signal variation of a plurality of data sets along with increasing the level of signal, values of a plurality of data sets to a desirable level.

In Example described below, two groups of data sets were compared. The data sets of group 1 were obtained by using various concentrations of signal-generating means such that the data sets of group 1 comprise data sets having various levels of signal values. The data sets of group 2 were obtained in such a manner that a raw data set was obtained by using low concentration of signal-generating means, followed by calibrating the raw data set using a plurality of reference values adjusted to calibrate the level of signal values of the raw data set to reach the various levels of signal values of data sets of group 1. As a result, it was verified that data sets of groups 1 and 2 exhibited similar patterns of an amplification curve and similar Ct values.

Furthermore, we verified that the CV of the calibrated raw data set obtained using low concentration of signal-generating means was substantially identical to that of the pre-calibrated raw data.

II. Storage Medium, Device and Computer Program

In another aspect of this invention, there is provided a computer readable storage medium containing instructions to configure a processor to perform a method for calibrating a data set of a target analyte in a sample, the method comprising:
 (a) providing a normalization coefficient for calibrating the data set; wherein the data set is obtained from a signal-generating process for the target analyte using a signal-generating means; wherein the data set comprises a plurality of data points comprising cycles of the signal-generating process and signal values at the cycles; wherein the normalization coefficient is provided by using a reference value, a reference cycle and the data set; wherein the reference cycle is selected from the cycles of the data set; wherein the reference value is an arbitrarily determined value; wherein the normalization coefficient is provided by defining a relationship between the reference value and a signal value at a cycle of the data set corresponding to the reference cycle; and
 (b) providing a calibrated data set by obtaining calibrated signal values by applying the normalization coefficient to the signal values of the data set.

In another aspect of this invention, there is provided a computer program to be stored on a computer readable storage medium to configure a processor to perform a method for calibrating a data set of a target analyte in a sample, the method comprising:
 (a) providing a normalization coefficient for calibrating the data set; wherein the data set is obtained from a signal-generating process for the target analyte using a signal-generating means; wherein the data set comprises a plurality of data points comprising cycles of the signal-generating process and signal values at the cycles; wherein the normalization coefficient is provided by using a reference value, a reference cycle and the data set; wherein the reference cycle is selected from the cycles of the data set; wherein the reference value is an arbitrarily determined value; wherein the normalization coefficient is provided by defining a relationship between the reference value and a signal value at a cycle of the data set corresponding to the reference cycle; and
 (b) providing a calibrated data set by obtaining calibrated signal values by applying the normalization coefficient to the signal values of the data set.

The program instructions are operative, when performed by the processor, to cause the processor to perform the present method described above. The program instructions for performing the method for calibrating a data set of a target analyte in a sample may comprise an instruction to provide a normalization coefficient for calibrating the data set by using a reference value, a reference cycle and the data set; and an instruction to provide a calibrated data set by obtaining calibrated signal values by applying the normalization coefficient to the signal values of the data set.

The present method described above is implemented in a processor, such as a processor in a stand-alone computer, a network attached computer or a data acquisition device such as a real-time PCR machine.

The types of the computer readable storage medium include various storage medium such as CD-R, CD-ROM, DVD, flash memory, floppy disk, hard drive, portable HDD, USB, magnetic tape, MINIDISC, nonvolatile memory card, EEPROM, optical disk, optical storage medium, RAM, ROM, system memory and web server.

The data set may be received through several mechanisms. For example, the data set may be acquired by a processor resident in a PCR data acquiring device. The data set may be provided to the processor in a real time as the data set is being collected, or it may be stored in a memory unit or buffer and provided to the processor after the experiment has been completed. Similarly, the data set may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. Similarly, the data set may be provided to a server system via a network connection (e.g., LAN, VPN, intranet, Internet and wireless communication network) to a client such as a notebook or a desktop computer system.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

In still further aspect of this invention, there is provided a device for calibrating data set of a target analyte in a sample, comprising (a) a computer processor and (b) the computer readable storage medium described above coupled to the computer processor.

According to an embodiment, the device further comprises a reaction vessel to accommodate the sample and signal-generating means, a temperature controlling means to control temperatures of the reaction vessel and/or a detector to detect signals at amplification cycles.

According to an embodiment, the computer processor permits not only to receive values of signals at cycles but also to analyze a sample or data set or obtain a calibrated data set of a target analyte in a sample. The processor may be prepared in such a manner that a single processor can do all performances described above. Alternatively, the processor unit may be prepared in such a manner that multiple processors do multiple performances, respectively.

According to an embodiment, the processor may be embodied by installing software into conventional devices for detection of target nucleic add molecules (e.g. real-time PCR device).

According to an embodiment, a calibrated data set is provided in such a manner that data set of a target analyte is obtained and the normalization coefficient is provided by using an arbitrarily determined reference value, a reference cycle and the data set, follow by obtaining calibrated signal values by applying the normalization coefficient to the signal values of the data set.

A reference value and a reference cycle may be arbitrarily determined by users or system suppliers. Alternatively, a reference value and a reference cycle may be determined by a device of the present invention. For example, the device of the present invention which collecting a plurality of data sets may be capable of determining a reference cycle from cycles in a background region regarding signal values of the accumulated plurality of data sets. Furthermore, the device of the present invention may be capable of determining a reference value within the average±standard deviation (SD) of signal values at the cycles of the plurality of data sets corresponding to the reference cycle regarding signal values of the accumulated plurality of data sets. In addition, the device of the present invention may be capable of determining a reference value regarding a ratio of a standard data set to a reference standard data set and a signal value of the reference cycle of the standard data set.

The features and advantages of this invention will be summarized as follows:

(a) According to the present invention, a data set is calibrated conveniently by applying a normalization coefficient to the data set to be calibrated such that the inter- and intra-instrument signal variations of data sets are reduced effectively. Particularly, not only the inter-instrument signal variations but also the intra-instrument signal variations between signal-generating processes caused by performing signal-generating processes in different positions (e.g., different reaction vessels or different wells) within an instrument are reduced, thereby the data set is capable of being analyzed with a high accuracy and reproductively.

(b) The present invention needs not a reference dye. More interestingly, the present method may calibrate a data set in more accurate and more economic manner than conventional signal calibration methods using a reference dye. For reducing inter-Instrument variation, the conventional calibration methods using the reference dye demand that the inter-instrument variation of an optical channel for detecting the reference dye and the inter-instrument variation of an optical channel for detecting a target analyte have to be the same. Therefore, the conventional calibration methods may not successfully solve problems associated with the inter-instrument variation by using only the reference dye and therefore they need an additional calibration through a hardware adjustment. Furthermore, for reducing the intra-instrument signal variation, the conventional methods require that conditions (e.g., quantity or quality of a reference dye) for using a reference dye in reaction mixtures have to be the same in all reaction mixtures, which may be also considered as shortcomings of the conventional methods.

(c) According to the present invention, a data set can be calibrated without introducing the reference dye into a reaction mixture such that a wavelength band allocation for calibration is not necessary. Therefore, there is no fluorescence interference caused by the reference dye, which is a great advantage especially in high multiplex real-time PCR.

(d) The calibration method of the present invention can be configured in software so that the method of the present invention is capable of being applied universally to various analytical instruments (e.g., real-time PCR instruments) regardless of manufacturers. Therefore, the method of the present invention is much more convenient and versatile than conventional hardware calibration methods.

(e) The signal variation is a serious problem in detecting RNA viruses using degenerated primers And/or probes. The signal variation between data sets can be reduced to dramatically through the present invention. Therefore, the present invention can be an excellent solution for the signal variation caused by using degenerated primers and/or probes for detecting RNA viruses.

(f) According to the present invention, the level of signal values of a data set is controllable by adjusting the reference value. As a result, a normalized data set with statistical significance may be obtained even when smaller amounts of signal-generating means (e.g., dNTPs or enzyme primers and probes) are used.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1: Calibration of Data Set by Using Specific Background Signal-Based Normalization (SBN) and Analysis of Calibrated Data Set The method of controlling the input or output signal intensity in hardware-wise is widely used for minimizing the intra-instrument signal variations in a real-time PCR. For example, the output intensity of the light source (e.g., LED and Halogen lamp) is adjusted or the input intensity of the signal is controlled in the filter of a detector for calibration of signals.

In Examples, the Specific Background signal-based Normalization (SBN) method of the present invention was used for calibrating variations in the amplified signals of data sets.

The signal variations in the following three groups of data sets were compared and analyzed: (i) a group of data sets obtained from an instrument without a hardware adjustment; (ii) a group of data sets obtained from an instrument with a hardware adjustment; and (iii) a group of data sets software-wise calibrated by the SBN.

<1-1> Preparation of Data Set

A real-time PCR for a target nucleic acid molecule was performed using a TaqMan probe as a signal-generating means with 50 cycles of an amplification in three CFX96™ Real-Time PCR Detection Systems (Bio-Rad) listed in Table 1. The target nucleic add molecule was a genomic DNA of *Ureaeplasma urealyticum*. The interactive dual label was provided by TaqMan probe labeled with a reporter molecule (FAM) and a quencher molecule (BHQ-1).

The reaction was conducted in the tube containing a target nucleic add molecule, a downstream primer, an upstream primer, TaqMan probe, and Master Mix containing $MgCl_2$, dNTPs and Taq DNA polymerase. The tube containing the reaction mixture was placed in the real-time thermocycler (CFX96, Bio-Rad). The reaction mixture was denatured for 15 min at 95° C. and subjected to 50 cycles of 10 sec at 95° C., 60 sec at 60° C., 10 sec at 72° C. Detection of the signal was performed at 60° C. of each cycle.

The 96 reactions in the respective 96-wells were carried out under the same condition in the respective instruments using the samples containing the same target nucleic add of the same concentration. By analyzing the data sets obtained from the above reactions, the level of an inter-instrument or intra-instrument signal variation and the level of reduction in the signal variations by the SBN method were analyzed.

A total of six groups of raw data sets were prepared, including three groups of data sets obtained from the reactions in the instrument without a hardware adjustment and the other three groups of data sets obtained from the reactions in the instrument with a hardware adjustment. Each group includes 96 data sets obtained from the 96 well-reactions.

The baseline subtracted data sets were obtained from the raw data sets. The baseline subtracted data sets were prepared according to the following way. The baseline was established from the third cycle to the cycle just before the signal amplification occurrence and then a regression straight line equation was calculated for the cycles in the established baseline region. The baseline subtracted data sets were prepared by subtracting the signal values calculated with the regression straight line equation at the corresponding cycle from the signal values measured at the respective cycles.

TABLE 1

| Name | Real-time PCR Instrument |
| --- | --- |
| Instrument 1 | CFX96 Real-time Cycler (Bio-Rad) |
| Instrument 2 | |
| Instrument 3 | |

<1-2> Analysis of Data Set Obtained from Instrument without Hardware Adjustment

The raw data sets and their baseline subtracted data sets obtained in Example <1-1> were used. The signal variations were analyzed in three groups of raw data sets obtained from the instruments without a hardware adjustment and in three groups of baseline subtracted data sets.

Figure 2A:
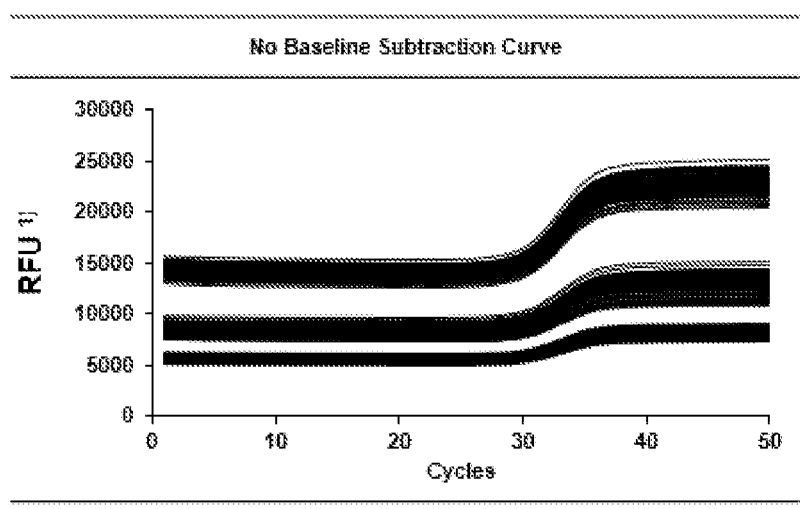
FIG. 2a represents amplification curves of three groups of raw data sets obtained respectively from three instruments without a hardware adjustment to show the inter-instrument and the intra-instrument variation of background signals.

In order to compare the background signal intensities of three instruments, amplification curves without baseline subtraction (No Baseline Subtraction Curve) were obtained by plotting the raw data sets without baseline subtraction (FIG. 2A).

As shown in FIG. 2A, the background signals of the respective instruments were shown to be separated from each other, which is unlike to the theoretical expectation that background signals having the same intensities will be plotted for amplification reactions under the same condition. In addition, it was observed that there was a distinct difference in the background signal intensity between the reactions performed in the differently located wells within the same instrument.

In order to compare signal variations in the amplification region, the amplification curves with baseline subtraction (Baseline Subtracted Curve) were prepared by plotting the baseline subtracted data sets obtained from the respective three instruments.

Figure 2B:
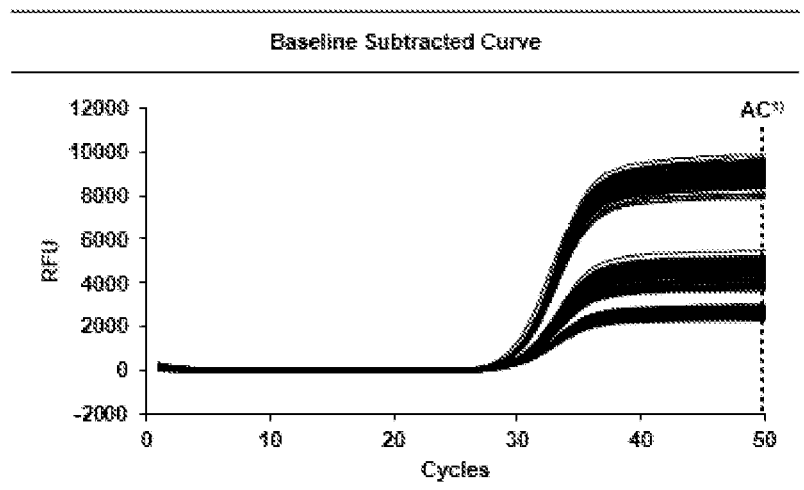
FIG. 2b represents baseline subtracted amplification curves of three groups of raw data sets obtained respectively from three instruments without a hardware adjustment and analytical results of the inter- and the intra-instrument coefficient of variation of the data sets.

The last cycle (i.e., $50^{th}$ cycle) of the baseline subtracted data sets was designated as an analytical cycle and the coefficient of variation (CV) of the amplification signals at $50^{th}$ cycle was calculated (FIG. 2B).

The coefficient of variation (CV) is defined as the ratio of the standard deviation to the arithmetic mean for the data.

The intra-instrument coefficient of variation was calculated from the standard deviation and the arithmetic mean of signal values at a specific cycle among the results of multiple reactions measured on a single instrument.

The inter-instrument coefficient of variation (CV) was calculated from the standard deviation and the arithmetic mean of signal values at a specific cycle in the resulting data sets of all reactions measured in three instruments used in the experiments.

The coefficients of variations of the amplification signals at the last cycle of amplification curves with baseline subtraction were represented in FIG. 2B. The intra-instrument coefficients of variations of the amplification signals of the instruments 1, 2, and 3 were analyzed as 5.2%, 9.1%, and 4.5%, respectively and the inter-instrument coefficient of variation of the amplification signals of the instruments 1, 2, and 3 was analyzed as 49.3%.

<1-3> Analysis of Data Set Obtained from Instrument with Hardware Adjustment

The raw data sets and their baseline subtracted data sets obtained in Example <1-1> were used. The signal variations were analyzed in three groups of raw data sets obtained from the instruments with a hardware adjustment and in three groups of baseline subtracted data sets.

Figure 3A:
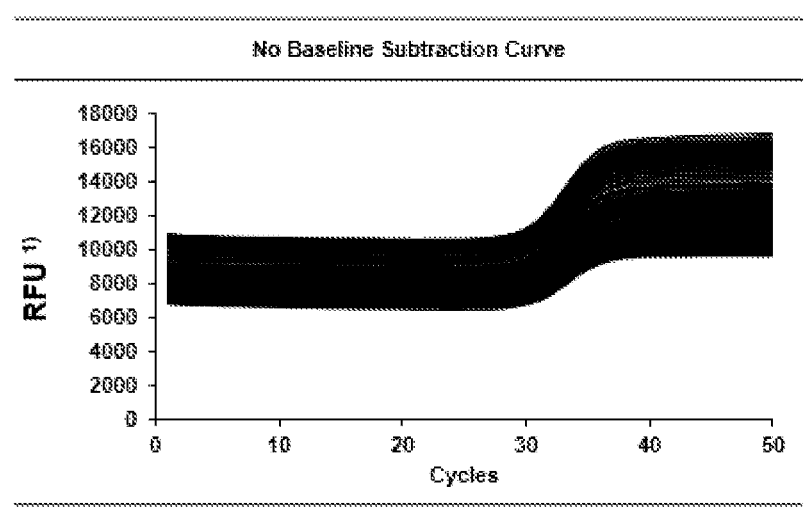
FIG. 3a represents amplification curves of three groups of raw data sets obtained respectively from three instruments with a hardware adjustment to show the inter-instrument and the intra-instrument variation of background signals.

The amplification curves without baseline subtraction (No Baseline Subtraction Curve) were analyzed according to the same method as described in Example <1-2>. As shown in FIG. 3A, even though the inter-instrument background signal variations became reduced compared to the instruments without a hardware adjustment, it was verified that there still remained widely distributed background signal variations between the instruments and between the reactions.

Figure 3B:
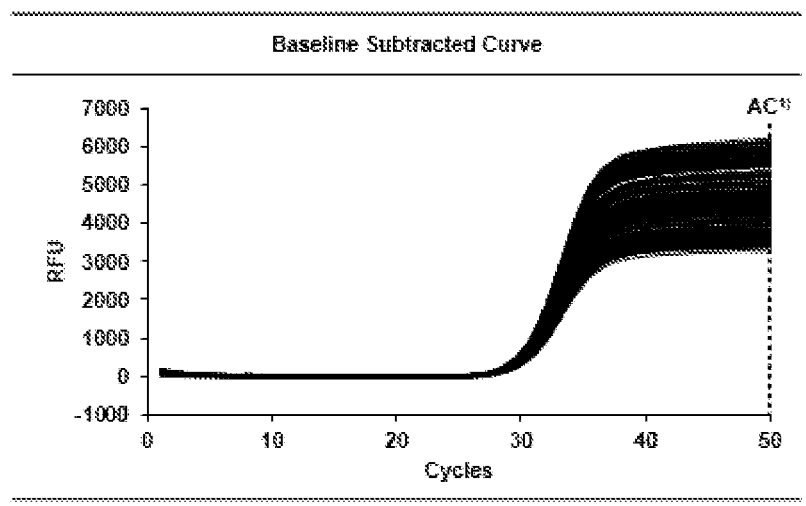
FIG. 3b represents baseline subtracted amplification curves of three groups of raw data sets obtained respectively from three instruments with a hardware adjustment and analytical results of the inter- and the intra-instrument coefficient of variation of the data sets.

The coefficients of variations of the amplification signals at the last cycle of the amplification curves with baseline subtraction (Baseline Subtracted Curve) were analyzed with the same way as described in Example <1-2>. As shown in FIG. 3B, the intra-Instrument coefficients of variations of the amplification signals of the instruments 1, 2, and 3 were analyzed as 5.3%, 7.8%, and 5.5%, respectively and the inter-instrument coefficient of variation of the amplification signals of the instruments 1, 2, and 3 was analyzed as 17.7%.

When the above results were compared with the results of the data sets obtained from the instrument without a hardware adjustment in Example <1-2>, it was proved that the inter-instrument coefficient of variation of the amplification signals was reduced by 31.6% P (percentage points) while there was negligent difference in the intra-instrument coefficient of variation of the amplification signals.

From the above results, it can be concluded that even though the calibration by the hardware adjustment can reduce partly the inter-instrument coefficient of variation of the amplification signals of the instruments, a considerable level of signal variations between the instruments still exists and the coefficient of variation of the amplification signals between the wells within a single instrument cannot be reduced by the hardware adjustment.

<1-4> Analysis of Data Set Software-Wise Calibrated Using SBN

The Specific Background signal-based Normalization (SBN) is a method of proportionally normalizing the data sets using the signal value at a reference cycle and the reference value, in which a specific cycle in a background signal region (baseline region) of the data sets to be calibrated is designated as the reference cycle. In order to normalize a plurality of data sets with regard to the same reference, both the reference value and the reference cycle may be equally applied to the data sets to be normalized. In case a plurality of data sets are divided into several groups according to reaction environments (e.g., an instrument used for amplification), reference values may be calculated in considering different reaction conditions between the groups and each reference value calculated may be applied to a respective group.

<1-4-1> Calibration of Data Set Using SBN Applied with Common Reference Value

In this Example, the data sets were calibrated by applying a single common reference value to data sets obtained from all instruments. The raw data sets of six groups obtained in Example <1-1> were software-wise calibrated using the SBN according to the following steps.

<Step 1>

A specific cycle in the background region (baseline region) of the raw data sets was designated as a reference cycle. The $5^{th}$ cycle is designated as the reference cycle in this Example.

<Step 2>

A reference value was designated for normalization with a specific background signal. The value of RFU 8,400 was designated as the reference value in this Example.

<Step 3>

A normalization coefficient was calculated from both of the signal value at the cycle of the raw data sets corresponding to the reference cycle and the reference value designated in the above step 2.

Normalization coefficient=Signal Value of Reference Cycle÷Reference Value.

<Step 4>

The signal values at all cycles were calibrated using the normalization coefficient.

Calibrated Signal Value(RFU)=Signal Value of Raw Data Set(RFU)÷Normalization Coefficient.

The calibrated six groups of data sets were obtained by calibrating the six groups of the raw data sets provided in Example <1-1> according to the above steps 1 to 4.

Figure 4A:
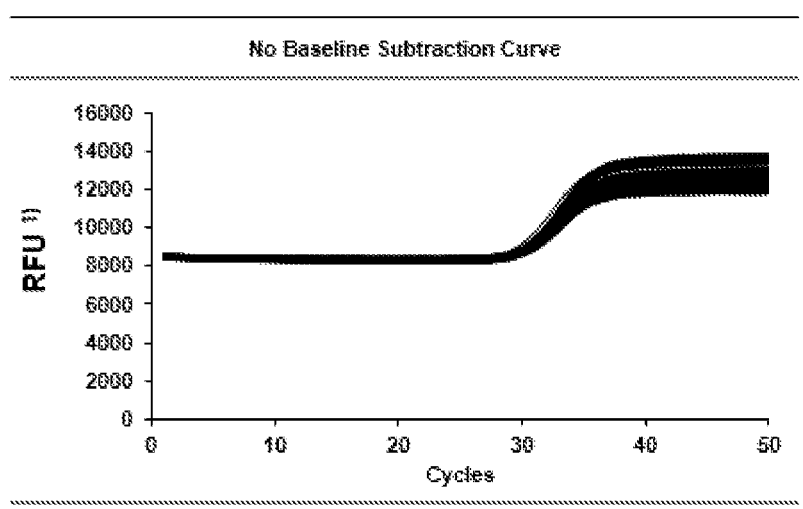
FIG. 4a represents amplification curves of calibrated data sets obtained by calibration of three groups of raw data sets by specific background signal based normalization method (SBN) of present invention using common reference value, wherein the raw data sets are obtained respectively from three instruments without a hardware adjustment.

A. Analysis of the Results of Calibration of the Data Sets Obtained from an Instrument without a Hardware Adjustment The data sets obtained from the instrument without a hardware adjustment were calibrated by the SBN, and the resulting calibrated data sets were analyzed. FIGS. 4A and 4B show the amplification curves (FIG. 4A) and the intra- and inter-instrument coefficients of variations (CVs) (FIG. 4B) for the calibrated data sets which were provided by calibrating the data sets obtained from the instrument without a hardware adjustment through the steps 1 to 4.

The amplification curves were obtained by plotting the calibrated data sets. FIG. 4A shows the amplification curves provided by plotting the calibrated data sets without baseline subtraction (No Baseline Subtraction Curve), in which the intensities of the background signals can be compared. As represented in FIG. 4A, the distribution of the background signal variations between the instruments was strikingly reduced by the calibration using the SBN. In particular, all of the RFUs at the $5^{th}$ cycle (i.e., the reference cycle) were identical to the reference value designated, addressing that there is no variation in the background signals.

In addition, the baseline subtracted amplification curves (Baseline Subtracted Curve) were obtained by subtracting the baseline from the calibrated data sets and plotting the baseline subtracted data sets, and then the coefficient of variation at $50^{th}$ cycle was calculated. In FIG. 4B representing the baseline subtracted curves, the signal variations in the amplification region were compared. The coefficients of variations of the amplification signals at the last cycle were analyzed. The intra-instrument coefficients of variations of the amplification signals were 2.3%, 3.0% and 1.0%, respectively and the inter-instrument coefficient of variation of the amplification signals was 12.1%.

The following three coefficients of variations were compared and analyzed: (i) the coefficient of variation of the signals in the data sets obtained from the instrument without a hardware adjustment in Example <1-2>; (ii) the coefficient of variation of the signals in the data sets obtained from the instrument with a hardware adjustment in Example <1-3>; and (iii) the coefficient of variation of the signals in the calibrated data sets provided by calibrating the data sets with the SBN, wherein the data sets had been obtained from the instrument without a hardware adjustment.

As shown in Table 2, the calibrated data sets provided by calibrating the data sets with the SBN, wherein the data sets had been obtained from the instrument without a hardware adjustment, have following characteristics: When compared with the data sets obtained from the instrument without a hardware adjustment, (i) the intra-instrument coefficient of variation of the amplification signals was reduced by more than a half; and (ii) the inter-instrument coefficient of variation of the amplification signals was remarkably reduced by 37.2 P % (percentage points). In addition, when compared with the data sets obtained from the instrument with a hardware adjustment, (i) the intra-instrument coefficient of variation of the amplification signals was reduced by more than a half; and (ii) the inter-instrument coefficient of variation of the amplification signals was reduced by 5.6 P % (percentage points).

It would be demonstrated that the signal calibration method of the invention using the SBN can reduce signal variations between the wells within an instrument as well as between the instruments. In particular, it would be understood that the SBN has more excellent calibration effect than methods of adjusting a hardware of an instrument, addressing that a signal calibration effect better than that of a hardware adjustment can be successfully accomplished by using only the SBN without a hardware adjustment of an instrument.

TABLE 2

| | | Calibration Method Specific Background signal-based Normalization(SBN) | | |
|---|---|---|---|---|
| | | − | − | + |
| | | Hardware Adjustment | | |
| | | − | + | − |
| Results of Analysis of Amplification Signal (Coefficient of Variation, CV, %) | Instrument 1 | 5.2 | 5.3 | 2.3 |
| | Instrument 2 | 9.1 | 7.8 | 3.0 |
| | Instrument 3 | 4.5 | 5.5 | 1.0 |
| | Total | 49.3 | 17.7 | 12.1 |

Figure 5A:
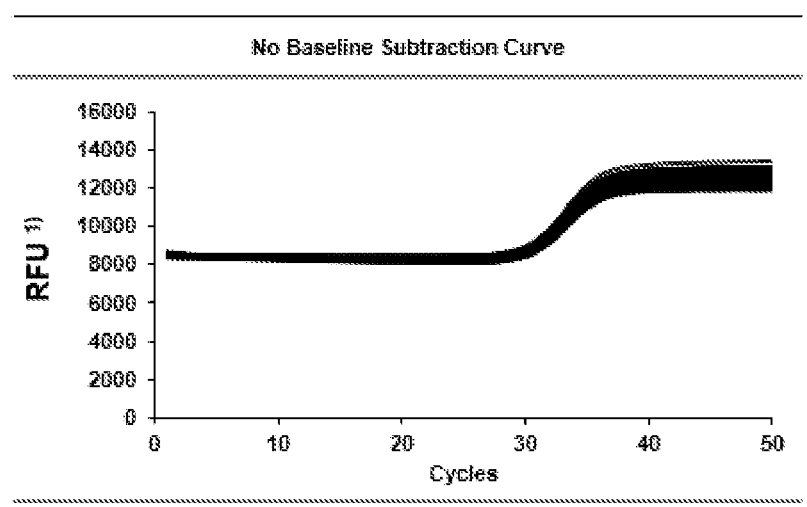
FIG. 5a represents amplification curves of calibrated data sets obtained by calibration of three groups of raw data sets by the SBN using a common reference value, wherein the raw data sets are obtained respectively from three instruments with a hardware adjustment.
Figure 5B:
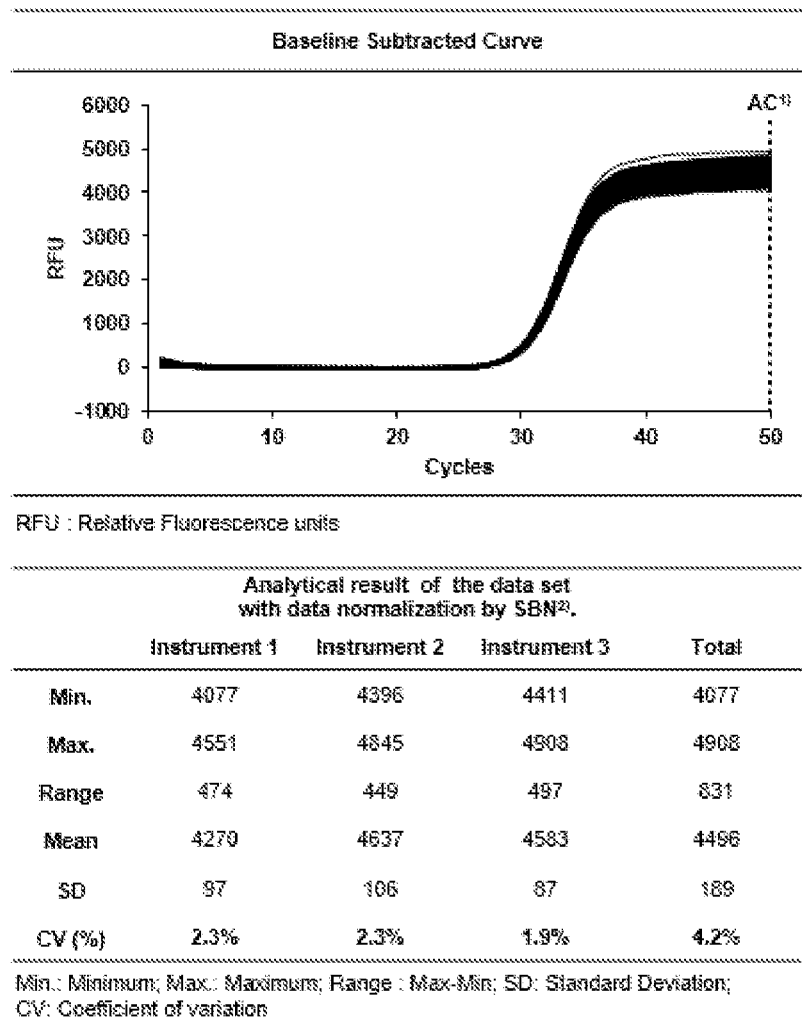
FIG. 5b represents baseline subtracted amplification curves of calibrated data sets obtained by calibration of three groups of raw data sets by the SBN using a common reference value, wherein the raw data sets are obtained respectively from three instruments with a hardware adjustment and analytical results of the inter- and the intra-instrument coefficient of variation of the calibrated data sets.

B. Analysis of the Results of Calibration of Data Sets Obtained from an Instrument with a Hardware Adjustment The data sets obtained from the instrument with a hardware adjustment were further calibrated by the SBN, and the resulting calibrated data sets were analyzed. FIGS. 5A and 5B show the amplification curves (FIG. 5A) and the intra- and inter-instrument coefficients of variations (FIG. 5B) for the calibrated data sets which were provided by calibrating the data sets obtained from the instrument with a hardware adjustment through the steps 1 to 4.

The amplification curves were obtained by plotting the calibrated data sets. FIG. 5A shows the amplification curves without baseline subtraction (No Baseline Subtraction Curve) for the calibrated data sets, in which the signal intensities in the background region can be compared. As represented in FIG. 5A, the inter-instrument background signal variations were highly reduced by the calibration using the SBN. In particular, all of the RFUs at $5^{th}$ cycle (i.e., the reference cycle) were identical to the reference value designated, addressing that there is no variation in the background signals.

In addition, the baseline subtracted amplification curves (Baseline Subtracted Curve) were obtained by subtracting the baseline from the calibrated data sets and plotting the baseline subtracted data sets, and then the coefficient of variation at $50^{th}$ cycle was calculated. In FIG. 5B representing the baseline subtracted curves, the signal variations in the amplification region were compared. The coefficients of variations of the amplification signals were analyzed. The intra-instrument coefficients of variations of the amplification signal were 2.3%, 2.3% and 1.9%, respectively and the inter-instrument coefficient of variation of the amplification signals was 4.2%.

The following three coefficients of variations were compared and analyzed: (i) the coefficient of variation of the signals in the data sets obtained from the instrument without a hardware adjustment in Example <1-2>; (ii) the coefficient of variation of the signals in the data sets obtained from the instrument with a hardware adjustment in Example <1-3>; and (iii) the coefficient of variation of the signals in the calibrated data sets provided by calibrating the data sets with SBN, wherein the data sets had been obtained from the instrument with a hardware adjustment.

As shown in Table 3, the calibrated data sets provided by calibrating the data sets with the SBN, wherein the data sets had been obtained from the instrument with a hardware adjustment, have following characteristics: When compared with the data sets obtained from the instrument without a hardware adjustment, (i) the intra-instrument coefficient of variation of the amplification signals was reduced by more than a half and (ii) the inter-instrument coefficient of variation of the amplification signals was remarkably reduced by 45.1 P % (percentage points). In addition, when compared with the data sets obtained from the instrument with a hardware adjustment, (i) the intra-instrument coefficient of variation of the amplification signals was reduced by more than a half; and (ii) the inter-instrument coefficient of variation of the amplification signals was remarkably reduced by 13.5 P % (percentage points).

It would be demonstrated that the signal calibration method of the invention using the SBN can reduce the signal variations between the wells within an instrument as well as between the instruments. In particular, it would be understood that the additional calibration effects on the data sets can be accomplished when the data sets obtained from the instrument with a hardware adjustment is further normalized by the SBN.

TABLE 3

| | | Calibration Method Specific Background signal-based Normalization(SBN) | | |
|---|---|---|---|---|
| | | − | − | + |
| | | Hardware Adjustment | | |
| | | − | + | + |
| Results of Analysis of Amplification | Instrument 1 | 5.2 | 5.3 | 2.3 |
| | Instrument 2 | 9.1 | 7.8 | 2.3 |

TABLE 3-continued

|  |  | Calibration Method Specific Background signal-based Normalization(SBN) | | |
|---|---|---|---|---|
|  |  | − | − | + |
|  |  | Hardware Adjustment | | |
|  |  | − | + | + |
| Signal (Coefficient of Variation, CV, %) | Instrument 3 | 4.5 | 5.5 | 1.9 |
|  | Total | 49.3 | 17.7 | 4.2 |

<1-4-2> Calibration of Data Set by SBN Using Instrument-Specific Reference Value Determined Based on Total Signal Change Value In this Example, a data set was calibrated using an instrument-specific reference value which h had as been determined with considering inter-instrument variations. The instrument-specific reference value is determined by using the ratio of a reference total signal change value (R-TSC) and a total signal change value (TSC) of a standard data sets of each instrument.

The reference total signal change value (R-TSC) can be determined from the total signal change value of the a data sets obtained from a standard instrument or the total signal change value of a plurality of data sets. In addition, the reference total signal change value (R-TSC) can be determined by the experimenter based on the results of a plurality of signal-generating processes for the corresponding target analyte.

The standard data set refers to a data set obtained through a signal-generating process for a target analyte of known concentration (standard concentration). The standard data set of each instrument is obtained by performing a signal-generating process on the instrument using a target analyte of known concentration.

The total signal change value (TSC) means a signal change amount (increased or decreased) of a corresponding data set. The instrument-specific total signal change value of a standard data set is calculated from a standard data set which is obtained from each instrument.

In order to determine the instrument-specific reference value, a standard data set of each instrument was obtained by using a target analyte of standard concentration and then the instrument-specific total signal change value (TSC) of the standard data set were determined, after which the ratio of the instrument-specific total signal change value of the standard data set to the pre-determined reference total signal change value (R-TSC) was calculated. A signal value at a reference cycle of the standard data set was calibrated using the calculated ratio and then the resulting calibrated signal value at the reference cycle was determined as the reference value to be applied to a data set obtained from a corresponding instrument.

The inter-instrument variation was additionally reduced by calibrating a data set obtained from a corresponding instrument using the determined instrument-specific reference value.

In the steps 1 to 3 below, the instrument-specific reference value was determined from the instrument-specific standard data set, and in the step 4, each raw data set obtained in Example <1-1> was calibrated using the determined instrument-specific reference value.

<Step 1>

An instrument-specific standard data set was obtained by performing a standard signal-generating process using a target analyte of standard concentration under the same reaction condition as that of practical signal-generating processes performed for obtaining data sets from a real experimental sample. A signal value and a total signal change value to determine a reference value were obtained from the standard data set.

Since the $5^{th}$ cycle was designated as a reference cycle in Example, the signal value at the $5^{th}$ cycle of the standard data set was designated as the signal value for use in the determination of the reference value.

In order to calculate the total signal change value of the standard data set, the baseline was subtracted from the obtained standard data set to yield a baseline subtracted data set as described in Example <1-1>. The total signal change value was calculated from the baseline subtracted data sets. The RFU at the last $50^{th}$ cycle (End-Point) of the baseline subtracted data set was designated as the total signal change value.

In this Example, three standard data sets were prepared from each instrument, and the total signal change value and the signal value used for determining the reference value were calculated. Specifically, the mean of the three total signal change values calculated from three instrument-specific standard data sets was designated as the total signal change value of the relevant instrument. The mean of the three signal values at the reference cycle calculated from three instrument-specific standard data sets was designated as the signal value used for determining the reference value of the relevant instrument.

The total signal change values (TSCs) and signal values to be used for determining the reference values of the standard data sets obtained from the instruments 1, 2, and 3 without or with a hardware adjustment were measured as shown in Table 4.

TABLE 4

|  | Total Signal Change Value (TSC) of Standard Data Sets (RFU) | | Signal Value at Reference Cycle of Standard Data Sets (Signal Value for Determining Reference Value) (RFU) | |
|---|---|---|---|---|
|  | Hardware Adjustment | | | |
|  | − | + | − | + |
| Instrument 1 | 2538 | 3513 | 5489 | 7011 |
| Instrument 2 | 4808 | 5470 | 8858 | 9898 |
| Instrument 3 | 8414 | 4601 | 13623 | 8390 |

<Step 2>

The reference total signal change value (R-TSC) used for determining the instrument-specific reference value together with the calculated total signal change value, was designated. In this Example, the RFU 4560, which is similar to the mean of the total signal change values of the data sets obtained from three instruments with a hardware adjustment of Example <1-1>, was designated as the reference total signal change value (See FIG. 3B).

<Step 3>

The reference values to be applied to the respective instruments were calculated with the following equation using three values of (i) the total signal change value of the standard data sets (step 1), (ii) the signal value of the reference cycle of the standard data sets (step 1), and (iii) the reference total signal change value (step 2).

Reference Value=Signal Value at Reference Cycle of Standard Data Set÷(Total Signal Change Value of Standard Data Set/Reference Total Signal Change Value)

The reference values to be used for calibrating the data sets obtained from the respective instruments 1, 2, and 3 without or with a hardware adjustment were determined as shown in Table 5.

TABLE 5

| Hardware Adjustment | Instrument Number | A) Total Signal Change Value of Standard Data Set (TSC) | B) Reference Total Signal Change Value (R-TSC) | C) Ratio of TSC to R-TSC [A/B] | D) Signal Value Of Reference Cycle of Standard Data Set | E) Determined Reference Value [D/C] |
|---|---|---|---|---|---|---|
| − | 1 | 2538 | 4560 | 0.5566 | 5489 | 9862 |
|   | 2 | 4808 | 4560 | 1.0545 | 8858 | 8400 |
|   | 3 | 8414 | 4560 | 1.8453 | 13623 | 7383 |
| + | 1 | 3513 | 4560 | 0.7705 | 7011 | 9099 |
|   | 2 | 5470 | 4560 | 1.1995 | 9898 | 8251 |
|   | 3 | 4601 | 4560 | 1.0090 | 8390 | 8316 |

<Step 4>

The six groups of raw data sets provided in Example <1-1> were calibrated through the same method as described in Example <1-4-1> using the reference values determined in the above step 3 and resulted in the calibrated six groups of data sets.

Figure 6A:
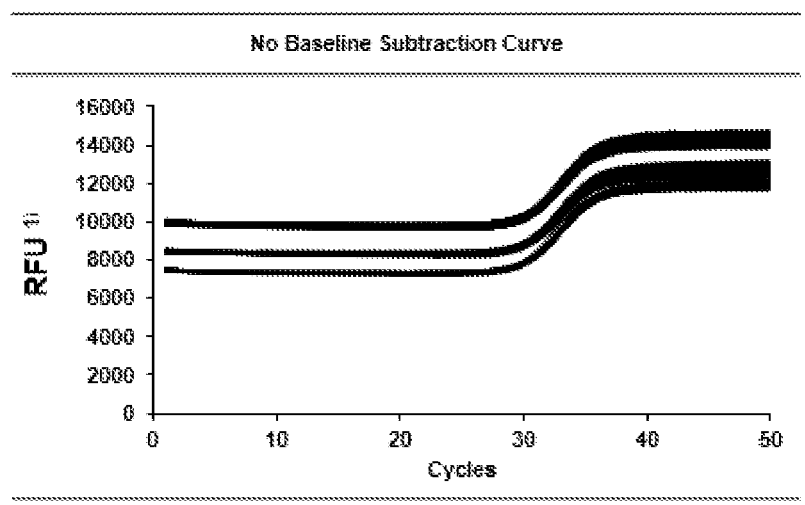
FIG. 6a represents amplification curves of calibrated data sets obtained by calibration of three groups of raw data sets by the SBN using an instrument-specific reference value, wherein the raw data sets are obtained respectively from three instruments without a hardware adjustment.
Figure 6B:
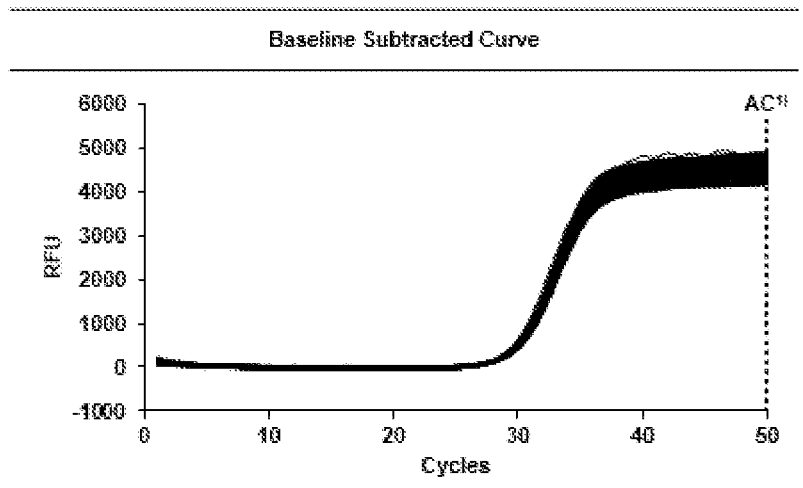
FIG. 6b represents baseline subtracted amplification curves of calibrated data sets obtained by calibration of three groups of raw data sets by the SBN using an instrument-specific reference value, wherein the raw data sets are obtained respectively from three instruments without a hardware adjustment and analytical results of the inter- and the intra-instrument coefficient of variation of the calibrated data sets.

A. Analysis of the Results of Calibration of Data Sets Obtained from an Instrument without a Hardware Adjustment The data sets obtained from an instrument without a hardware adjustment were calibrated by the SBN using the instrument-specific reference value, and the resulting calibrated data sets were analyzed. FIGS. 6A and 6B show the amplification curves (FIG. 6A) and the intra- and inter-instrument coefficients of variations (FIG. 69) for the calibrated data sets which were provided by calibrating the data sets obtained from the instrument without a hardware adjustment through the steps 1 to 4.

The amplification curves were obtained by plotting the calibrated data sets. FIG. 6A shows the amplification curves provided by plotting the calibrated data sets without baseline subtraction (No Baseline Subtraction Curve), in which the intensities of the signals in the background and amplification regions can be compared. The signal values at the $5^{th}$ cycle of the data sets from the three instruments were calibrated into RFU 9862, 8400, and 7383 (i.e., the instrument-specific reference values), respectively and thus the signals in the background region became similar to one another and the signals in the amplification region also became similar to one another.

In addition, the baseline subtracted amplification curves (Baseline Subtracted Curve) were obtained by subtracting the baseline from the calibrated data sets and plotting the baseline subtracted data sets, and then the coefficient of variation at the $50^{th}$ cycle was calculated. In FIG. 6B representing the baseline subtracted amplification curve, the signal variations in the amplification region were compared. The coefficients of variations of the amplification signals were analyzed. The intra-instrument coefficients of variations of the amplification signals were 2.3%, 3.0% and 1.0%, respectively and the inter-instrument coefficient of variation of the amplification signal was 3.0%.

The following three coefficients of variations were compared and analyzed: (i) the coefficient of variation of the signals in the data sets obtained from the instrument without a hardware adjustment in Example <1-2>; (ii) the coefficient of variation of the signals in the data sets obtained from the instrument with hardware adjustment in Example <1-3>; and (iii) the coefficient of variation of the signals in the calibrated data sets provided by calibrating the data sets with the SBN using the instrument-specific reference value of this Example, in which the data sets had been obtained from the instrument without a hardware adjustment.

As shown in Table 6, the calibrated data sets provided by calibrating the data sets with the SBN using the instrument-specific reference value, wherein the data sets had been obtained from the instrument without a hardware adjustment, have following characteristics: When compared with the data sets obtained from the instrument without a hardware adjustment, (i) the intra-instrument coefficient of variation of the amplification signal was reduced by more than a half; and (ii) the inter-instrument coefficient of variation of the amplification signal was remarkably reduced by 46.3 P % (percentage points). In addition, when compared with the data sets obtained from the instrument with a hardware adjustment, (i) the inter-instrument coefficient of variation of the amplification signals was reduced by more than a half; and (ii) the inter-instrument coefficient of variation of the amplification signals was reduced by 14.7 P % (percentage points).

It would be demonstrated that the signal calibration method of the invention can effectively reduce both the inter-instrument signal variations and the inter-well signal variations within an instrument even by adjusting the instrument-specific reference values using the instrument-specific standard data sets.

TABLE 6

| Calibration Method | SBN Using Instrument-Specific Reference Value | − | − | + |
|---|---|---|---|---|
|   | Hardware Adjustment | − | + | − |
| Result of Analysis of Amplification | Instrument 1 | 5.2 | 5.3 | 2.3 |
|   | Instrument 2 | 9.1 | 7.8 | 3.0 |
|   | Instrument 3 | 4.5 | 5.5 | 1.0 |
| Signal (Coefficient of Variation, CV %) | Total | 49.3 | 17.7 | 3.0 |

Figure 7A:
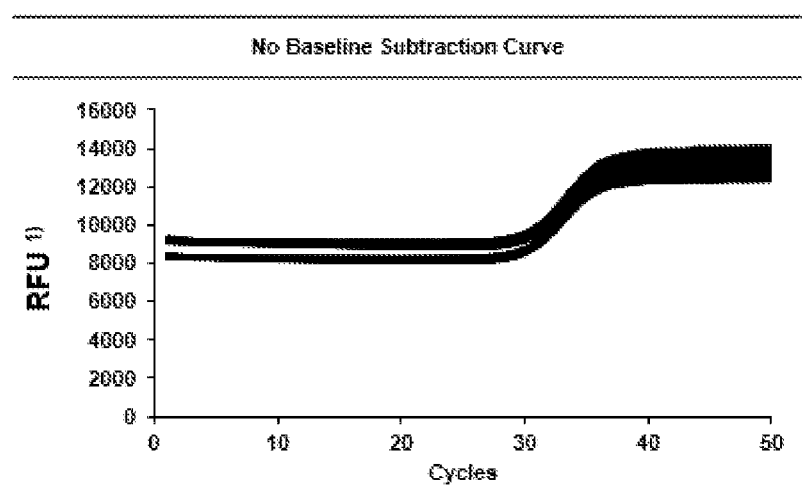
FIG. 7a represents amplification curves of calibrated data sets obtained by calibration of three groups of raw data sets by the SBN using an instrument-specific reference value, wherein the raw data sets are obtained respectively from three instruments with a hardware adjustment.
Figure 7B:
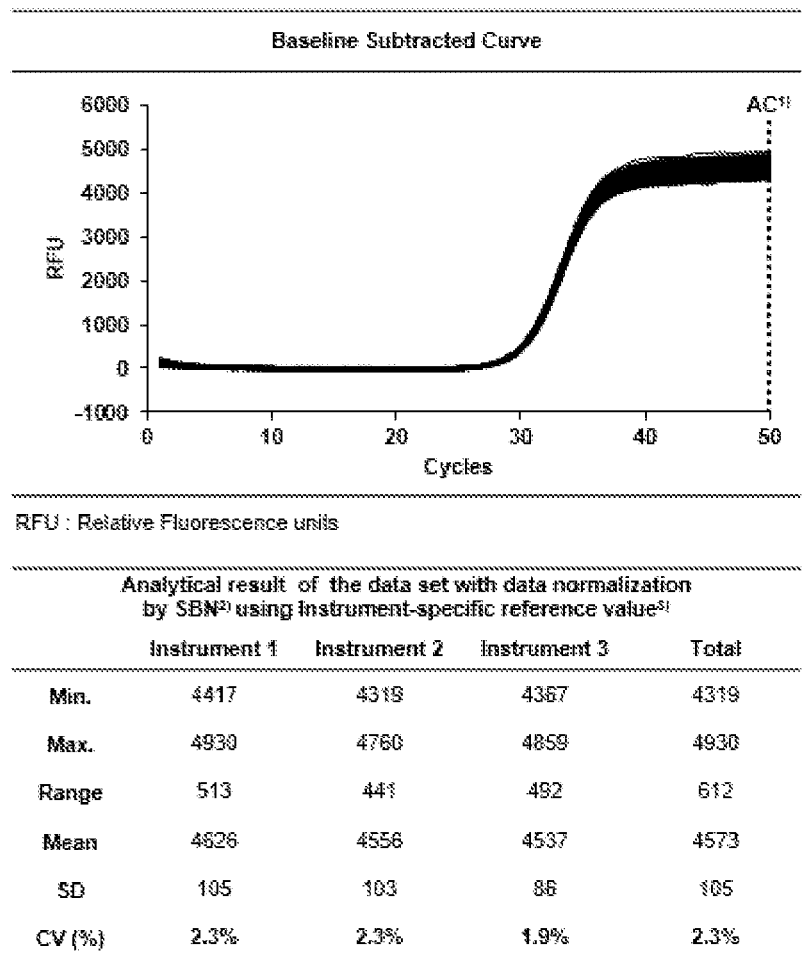
FIG. 7b represents baseline subtracted amplification curves of calibrated data sets obtained by calibration of three groups of raw data sets by the SBN using an instrument-specific reference value, wherein the raw data sets are obtained respectively from three instruments with a hardware adjustment and analytical results of the inter- and the intra-instrument coefficient of variation of the calibrated data sets.

B. Analysis of the Results of Calibration of Data Sets Obtained from an Instrument with a Hardware Adjustment The data sets obtained from an instrument with a hardware adjustment were further calibrated by the SBN using an instrument-specific reference value, and the resulting calibrated data sets were analyzed. FIGS. 7A and 7B show the amplification curves (FIG. 7A) and the intra- and inter-instrument coefficients of variations (FIG. 7B) for the calibrated data sets which were provided by calibrating the data sets obtained from the instrument with a hardware adjustment through the steps 1 to 4.

The amplification curves were obtained by plotting the calibrated data sets. FIG. 7A shows the amplification curves without baseline subtraction (No Baseline Subtraction Curve) for the calibrated data sets, in which the signal intensities in the background and amplification regions can be compared. The signal values at the $5^{th}$ cycle of the data sets from the respective three instruments were calibrated into RFU 9099, 8251, and 8316 (i.e., the instrument-specific reference values), respectively and thus the signals in the background region became similar to one another and the signals in the amplification region also became similar to one another.

In addition, the baseline subtracted amplification curves were obtained by subtracting the baseline from the calibrated data sets and plotting the baseline subtracted data sets, and then the coefficient of variation at the $50^{th}$ cycle was calculated. In FIG. 7B representing the baseline subtracted curve (Baseline Subtracted Curve), the signal variations in the amplification region were compared. The coefficients of variation of the amplification signals were analyzed. The intra-instrument coefficients of variations of the amplification signals were 2.3%, 2.3% and 1.9%, respectively and the inter-instrument coefficient of variation of the amplification signals was 2.3%.

The following three coefficients of variations were compared and analyzed: (i) the coefficient of variation of the signals in the data sets obtained from the instrument without a hardware adjustment in Example <1-2>; (ii) the coefficient of variation of the signals in the data sets obtained from the instrument with a hardware adjustment in Example <1-3>; and (iii) the coefficient of variation of the signal in the calibrated data sets provided by calibrating the data sets by the SBN using the instrument-specific reference value of this Example, in which the data sets had been obtained from the instrument with a hardware adjustment.

As shown in Table 7, the calibrated data sets provided by calibrating the data sets by the SBN using the instrument-specific reference value, wherein the data sets had been obtained from the instrument with a hardware adjustment, have following characteristics: When compared with the data sets obtained from the instrument without a hardware adjustment, (i) the intra-instrument coefficient of variation of the amplification signals was reduced by more than a half; and (ii) the inter-instrument coefficient of variation of the amplification signals was remarkably reduced by 47 P % (percentage points). In addition, when compared with the data sets obtained from the instrument with a hardware adjustment, (i) the intra-instrument coefficient of variation of the amplification signals was reduced by more than a half; and (ii) the inter-instrument coefficient of variation of the amplification signals was remarkably reduced by 15.4 P % (percentage points).

It would be demonstrated that the signal calibration method of the invention can effectively reduce both the inter-instrument signal variations and the inter-well signal variations within an instrument even by adjusting the instrument-specific reference values using the instrument-specific reference data sets. In particular, it would be understood that the additional calibration effects on the data sets can be accomplished when the data sets obtained from the instrument with a hardware adjustment is further normalized by the SBN.

TABLE 7

| Calibration Method | SBN Using Instrument-Specific Reference Value | – | – | + |
|---|---|---|---|---|
| | Hardware Adjustment | – | + | – |
| Result of Analysis of Amplification | Instrument 1 | 5.2 | 5.3 | 2.3 |
| | Instrument 2 | 9.1 | 7.8 | 2.3 |
| | Instrument 3 | 4.5 | 5.5 | 1.9 |
| Signal (Coefficient of Variation, CV %) | Total | 49.3 | 17.7 | 2.3 |

The present method for calibrating signals from a real-time PCR instrument using the SBN can be used to reduce both the intra-instrument variations of signals and the inter-Instrument variations of signals with easy and software access. Furthermore, the present calibration method can be universally applied to various real-time PCR instruments because it adjusts the data sets in a software-wise manner not hardware-wise. Moreover, the method of the invention is able to additionally calibrate signals that have been already hardware-wise calibrated. Instruments such as Real-time PCR instruments have been subjected to a hardware adjustment before being put on a market. Where applied to Instruments with hardware adjustment, the present method can provide more precisely calibrated instruments.

Example 2: Calibration and Analysis of the Data Set by Using Instrument Blank Signal Subtraction and Specific Background Signal Based Normalization (IBS-SBN)

The calibration of the data sets using the SBN will be more accurate if a signal value corresponding to an Instrument blank signal is subtracted from the data sets. In this Example, the method of Instrument Blank signal Subtraction and Specific Background signal-based Normalization (IBS-SBN) was used for the calibration of the amplified signal variations.

The amplification signal variations in the following three groups of data sets were compared and analyzed: (i) a group of data sets obtained from an instrument without a hardware adjustment of Example <1-1>; (ii) a group of data sets obtained from an instrument with a hardware adjustment of Example <1-1>; and (iii) a group of data sets obtained by calibrating the data sets of Example <1-1> software-wise by the IBS-SBN.

<2-1> Measurement of Instrument Blank Signal

Raw data sets generally include both of signals generated by the fluorescent molecule and an instrument blank signal generated basically in the absence of the fluorescent molecule. Accordingly, it is preferable to measure an instrument blank signal and subtract it from raw data sets in order to utilize signals generated only by the fluorescent molecule and thus obtain more accurate results.

In this Example, the signal measured from an empty tube was used as the instrument blank signal.

The measurement of an instrument blank signal may be performed around the temperature for detecting signals of a real-time PCR or may be performed in the presence or absence of the repetition of an amplification cycle. In this Example, 10 cycles of the amplification were performed under the same condition as described in Example <1-1> and the signal value measured at the $10^{th}$ cycle was used as the instrument blank signal. The instrument blank signal was measured respectively as shown in Table 9.

TABLE 9

| Name | Instrument Blank Signal of Instrument without Hardware Adjustment | Instrument Blank Signal of Instrument with Hardware Adjustment |
| --- | --- | --- |
| Instrument 1 | RFU 2525 | RFU 2977 |
| Instrument 2 | RFU 3152 | RFU 3638 |
| Instrument 3 | RFU 3629 | RFU 3010 |

<2-2> Obtaining the $1^{st}$ Calibrated Data Set by Instrument Blank signal Subtraction (IBS)

The $1^{st}$ calibrated data set was obtained by subtracting the instrument blank signal of Example <2-1> from the raw data sets of Example <1-1> as the following equation:

$1^{st}$ Calibrated Data Set=Raw Data set−Instrument Blank Signal

By the calculation using the above equation, a total of six groups of $1^{st}$ calibrated data sets were provided, including three groups of the $1^{st}$ calibrated data sets obtained by using the raw data sets of the instruments without a hardware adjustment and the other three groups of the $1^{st}$ calibrated data sets obtained by using the raw data sets of the instruments with a hardware adjustment.

<2-3> Calibration of Data Set by SBN and Analysis of Calibrated Data Set

The $2^{nd}$ calibrated data sets were provided by applying the SBN of Example <1-4> to the $1^{st}$ calibrated data sets, and then analyzed.

<2-3-1> Calibration of Data Set Using IBS-SBN Applied with Common Reference Value In this Example, the six groups of the $1^{st}$ calibrated data sets obtained by Instrument Blank signal Subtraction (IBS) of Example <2-2> were software-wise calibrated using the SBN according to the following steps.

<Step 1>

A specific cycle in the baseline region of the data sets is designated as a reference cycle. In this Example, the $5^{th}$ cycle was designated as the reference cycle.

<Step 2>

A reference value is designated for the normalization with a specific background signal. In this Example, the value of RFU 5,350 was designated as the reference value.

<Step 3>

A normalization coefficient was calculated from both of the signal value at the cycle corresponding to the reference cycle in the $1^{st}$ calibrated data set and the reference value designated in the above step 2.

Normalization Coefficient=Signal Value at Reference Cycle÷Reference Value

<Step 4>

The signal values at all cycles were calibrated using the normalization coefficient.

$2^{nd}$ Calibrated Signal Value(RFU)=Signal Value of $1^{st}$ Calibrated Data Set(RFU)+Normalization Coefficient.

The six groups of the $2^{nd}$ calibrated data sets were obtained by calibrating the six groups of the $1^{st}$ calibrated data sets provided by Example <2-2> according to the steps 1 to 4.

Figure 8A:
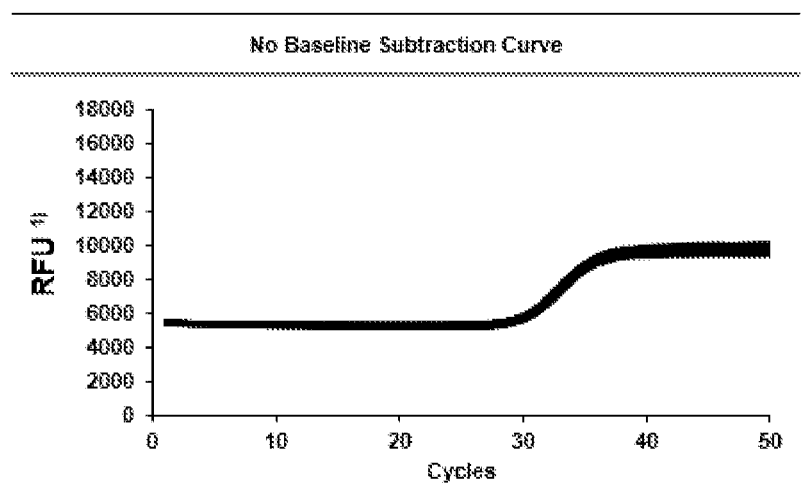
FIG. 8a represents amplification curves of calibrated data sets obtained by calibration of three groups of raw data sets by the instrument blank signal subtraction and specific background signal based normalization the IBS-SBN method of the present invention using a common reference value, wherein the raw data sets are obtained respectively from three instruments without a hardware adjustment.
Figure 8B:
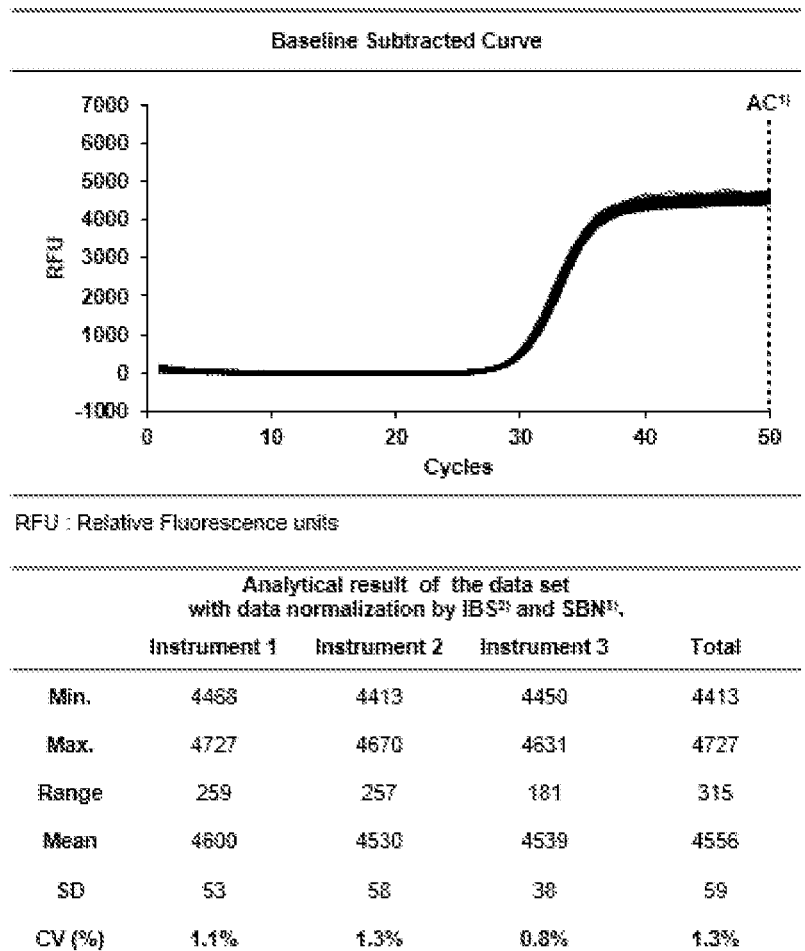
FIG. 8b represents baseline subtracted amplification curves of calibrated data sets obtained by calibration of three groups of raw data sets by the IBS-SBN using a common reference value, wherein the raw data sets are obtained respectively from three instruments without a hardware adjustment and analytical results of the inter- and the intra-instrument coefficient of variation of the calibrated data sets.

A. Analysis of the Results of Calibration of the Data Sets Obtained from an Instrument without a Hardware Adjustment The $2^{nd}$ calibrated data set were obtained by calibrating the data sets obtained from an instrument without a hardware adjustment with the IBS-SBN, and the resulting $2^{nd}$ calibrated data sets were analyzed. FIGS. 8A and 8B show the amplification curves (FIG. 8A) and the intra- and inter-instrument coefficients of variations (FIG. 8B) for the $2^{nd}$ calibrated data sets which were provided by subtracting the instrument blank signals from the data sets obtained from an instrument without a hardware adjustment and then calibrating them through the steps 1 to 4.

The amplification curves were obtained by plotting the $2^{nd}$ calibrated data sets. FIG. 8A shows the amplification curves provided by plotting the $2^{nd}$ calibrated data sets without baseline subtraction (No Baseline Subtraction Curve), in which the intensities of the background signals can be compared. The distribution of the background signal variations between the instruments was highly reduced by the IBS-SBN. In particular, all of the RFUs at the $5^{th}$ cycle (i.e., the reference cycle) were identical to the reference values designated, addressing that there is no variation in the background signals.

In addition, the baseline subtracted amplification curves (Baseline Subtracted Curve) were obtained by subtracting the baseline from the $2^{nd}$ calibrated data sets and plotting the baseline subtracted data sets, and then the coefficient of variation at the $50^{th}$ cycle was calculated. In FIG. 8B representing the baseline subtracted curves, the signal variations in the amplification region were compared. The coefficients of variations of the amplification signals at the last cycle were analyzed. The intra-instrument coefficients of variations of the amplification signals were 1.1%, 1.3% and 0.8% respectively and the inter-instrument coefficient of variation of the amplification signals was 1.3%.

The following three coefficients of variations were compared and analyzed: (i) the coefficient of variation of the signals in the data sets obtained from the instrument without a hardware adjustment in Example <1-2>; (ii) the coefficient of variation of the signals in the data sets obtained from the instrument with a hardware adjustment in Example <1-3>; and (iii) the coefficient of variation of the signals in the $2^{nd}$ calibrated data sets provided by calibrating the data sets by the IBS-SBN in which the data sets had been obtained from the instrument without a hardware adjustment.

As shown in Table 10, the calibrated data sets provided by calibrating the data sets with the IBS-SBN, wherein the data sets were obtained from the instrument without a hardware adjustment, have following characteristics: When compared with the data sets obtained from the instrument without a hardware adjustment, (i) the intra-instrument coefficient of variation of the amplification signals was reduced by more than a half; and (ii) the inter-instrument coefficient of variation of the amplification signals was remarkably reduced by 48.0 P % (percentage points). In addition, when compared with the data sets obtained from the instrument with a hardware adjustment, (i) the intra-instrument coefficient of variation of the amplification signals was reduced by more than a half; and (ii) the inter-instrument coefficient of variation of the amplification signals was remarkably reduced by 16.4 P % (percentage points).

It would be demonstrated that the signal calibration method of the invention using the IBS-SBN can reduce both the inter-instrument signal variations and the inter-well signal variations within an instrument. In particular, it would be understood that the IBS-SBN had superior calibration effects to the method of calibrating the instrument in hardware-wise, addressing that a signal calibration effect better than that of the hardware calibration can be successfully accomplished by using only the IBS-SBN without a hardware adjustment of the instrument.

TABLE 10

| Calibration Method | Instrument Blank Signal Subtraction and Specific Background signal-based Normalization (IBS-SBN) | – | – | + |
|---|---|---|---|---|
| | Hardware Adjustment | – | + | – |
| Results of Analysis of Amplification Signal (Coefficient of Variation, CV %) | Instrument 1 | 5.2 | 5.3 | 1.1 |
| | Instrument 2 | 9.1 | 7.8 | 1.3 |
| | Instrument 3 | 4.5 | 5.5 | 0.8 |
| | Total | 49.3 | 17.7 | 1.3 |

Figure 9A:
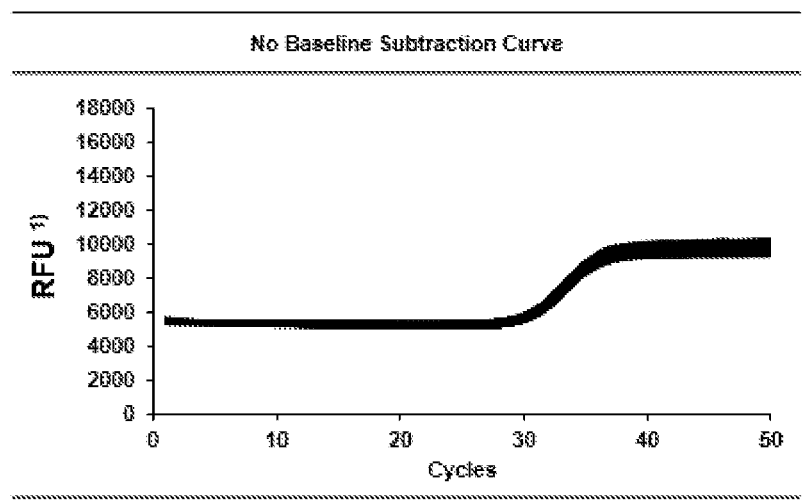
FIG. 9a represents amplification curves of calibrated data sets obtained by calibration of three groups of raw data sets by the IBS-SBN using a common reference value, wherein the raw data sets are obtained respectively from three instruments with a hardware adjustment.
Figure 9B:
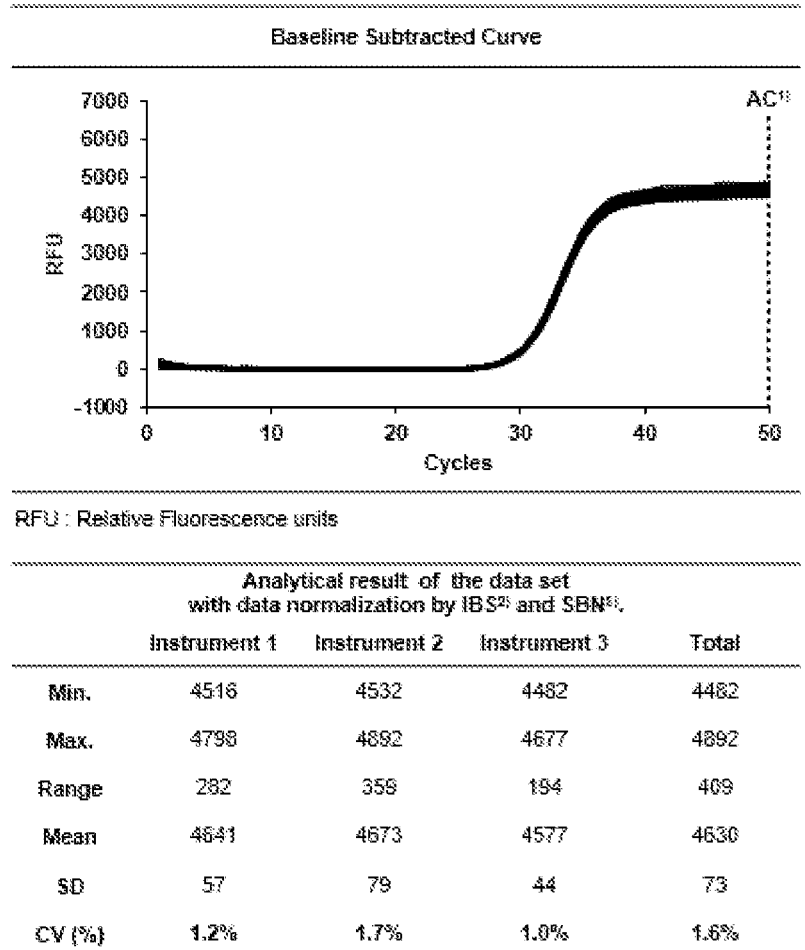
FIG. 9b represents baseline subtracted amplification curves of calibrated data sets obtained by calibration of three groups of raw data sets by the IBS-SBN using a common reference value, wherein the raw data sets are obtained respectively from three instruments with a hardware adjustment and analytical results of the inter- and the intra-instrument coefficient of variation of the calibrated data sets.

B. Analysis of the Results of Calibration of Data Sets Obtained from an instrument with a Hardware Adjustment The data sets obtained from an instrument with a hardware adjustment were further calibrated by the IBS-SBN and resulted in the $2^{nd}$ calibrated data sets. The resulting $2^{nd}$ calibrated data sets were analyzed. FIGS. 9A and 9B show the amplification curves (FIG. 9A) and the intra- and inter-instrument coefficients of variations (FIG. 9B) for the $2^{nd}$ calibrated data sets which were provided by subtracting the instrument blank signals from the data sets obtained from the instrument with a hardware adjustment and then calibrating them through the steps 1 to 4.

The amplification curves were obtained by plotting the $2^{nd}$ calibrated data sets. FIG. 9A shows the amplification curves without baseline subtraction (No Baseline Subtraction Curve) for the $2^{nd}$ calibrated data sets, in which the signal intensities in the background region can be compared. The inter-instrument background signal variations were highly reduced by using the IBS-SBN (see FIG. 9A). In particular, all of the RFUs at the $5^{th}$ cycle (i.e., the reference cycle) were identical to the reference value designated, addressing that there is no variation in the background signals.

In addition, the baseline subtracted amplification curves (Baseline Subtracted Curve) were obtained by subtracting the baseline from the $2^{nd}$ calibrated data sets and plotting the baseline subtracted data sets, and then the coefficient of variation at $50^{th}$ cycle was calculated. In FIG. 9B representing the baseline subtracted curves, the signal variations in the amplification region were compared. The coefficients of variations of the amplification signals at the last cycle were analyzed. The intra-instrument coefficients of variations of the amplification signals were 1.2%, 1.7% and 1.0%, respectively and the inter-instrument coefficient of variation of the amplification signals was 1.6%.

The following three coefficients of variations were compared and analyzed: (i) the coefficient of variation of the signals in the data sets obtained from the instrument without a hardware adjustment in Example <1-2>; (ii) the coefficient of variation of the signals in the $1^{st}$ data sets obtained from the instrument with a hardware adjustment in Example <1-3>; and (iii) the coefficient of variation of the signals in the $2^{nd}$ calibrated data sets provided by calibrating the data sets by the IBS-SBN, wherein the data sets were obtained from the instrument with a hardware adjustment.

As shown in Table 11, the calibrated data sets provided by calibrating the data sets with the IBS-SBN, wherein the data sets were obtained from the instrument with a hardware adjustment, have following characteristics: When compared with the data sets obtained from the instrument without a hardware adjustment, (i) the intra-instrument coefficient of variation of the amplification signals was reduced by more than a half; and (ii) the inter-instrument coefficient of variation of the amplification signals was remarkably reduced by 47.3 P % (percentage points). In addition, when compared with the data sets obtained from the instrument with a hardware adjustment, (i) the intra-instrument coefficient of variation of the amplification signals was reduced by more than a half; and (ii) the inter-instrument coefficient of variation of the amplification signals was remarkably reduced by 16.1 P % (percentage points).

It would be demonstrated that the signal calibration method of the invention using the IBS-SBN can effectively reduce both the inter-instrument signal variations and the inter-well signal variations within an instrument. In particular, it would be understood that the additional calibration effects on the data sets can be accomplished when the data sets obtained from the instrument with a hardware adjustment is further normalized by the IBS-SBN.

TABLE 11

| Calibration Method | Instrument Blank Signal Subtraction and Specific Background signal-based Normalization (IBS-SBN) | – | – | + |
|---|---|---|---|---|
| | Hardware Adjustment | – | + | – |
| Results of Analysis of Amplification Signal (Coefficient of Variation, CV %) | Instrument 1 | 5.2 | 5.3 | 1.2 |
| | Instrument 2 | 9.1 | 7.8 | 1.7 |
| | Instrument 3 | 4.5 | 5.5 | 1.0 |
| | Total | 49.3 | 17.7 | 1.6 |

<2-3-2> Calibration of Data Set by IBS-SBN Using Instrument-Specific Reference Value Determined Based on Total Signal Change Value In this Example, the data sets were calibrated using an instrument-specific reference value which had been determined with considering inter-instrument variations.

In the steps 1-3 below, the instrument-specific reference values were determined from the instrument-specific standard data sets, and in the step 4 below, the $1^{st}$ calibrated data sets obtained in Example <2-2> were calibrated respectively using the determined instrument-specific reference values.

<Step 1>

An instrument-specific standard data set was obtained by performing a standard signal-generating process using a target analyte of standard concentration under the same reaction condition as that of practical signal-generating processes performed for obtaining data sets from a real experimental sample. A signal value and d total signal change value to determine a reference value were obtained from the standard data set.

Since the $5^{th}$ cycle was designated as a reference cycle in Example, the signal value at the $5^{th}$ cycle of the standard data set was designated as the signal value for use in determination of the reference value.

In order to calculate the total signal change value of the standard data sets, the $1^{st}$ calibrated data sets were provided through the same steps as described in Example <2-2> using the obtained standard data sets and the baseline subtracted data sets were provided by subtracting the baseline from the obtained standard data sets according to the same methods as described in Example <1-1>. The total signal change values were calculated from the baseline subtracted data sets. The RFU at the last $50^{th}$ cycle (End-Point) of the baseline subtracted data set was designated as the total signal change value.

In this Example, three standard data sets were obtained from each instrument, and the total signal change value and the signal value used for determining the reference value were calculated. Specifically, the mean of the three total signal change values calculated from three instrument-specific standard data sets was designated as the total signal change value of the relevant instrument. The mean of the three signal values at the reference cycle calculated from three instrument-specific standard data sets was designated as the signal value used for determining the reference value of the relevant instrument.

The total signal change values (TSCs) and signal values to be used for determining the reference values of the standard data sets obtained from the instruments 1, 2, and 3 without or with a hardware adjustment were measured as shown in Table 12.

TABLE 12

|  | Total Signal Change Value (TSC) of Standard Data Sets (RFU) | | Signal Value at Reference Cycle of Standard Data Sets (Signal Value Used for Determining Reference Value) (RFU) | |
| --- | --- | --- | --- | --- |
| Hardware Adjustment | − | + | − | + |
| Instrument 1 | 2538 | 3513 | 2964 | 4034 |
| Instrument 2 | 4808 | 5470 | 5706 | 6260 |
| Instrument 3 | 8414 | 4601 | 9994 | 5380 |

<Step 2>

The reference total signal change value (R-TSC) used for determining the instrument-specific reference value together with the calculated total signal change value, was designated. In this Example, the RFU 4560, which is similar to the mean of the total signal change values of the data sets obtained from three instruments with a hardware adjustment of Example <1-1>, was designated as the reference total signal change value (FIG. 3B).

<Step 3>

The reference values to be applied to the respective instruments were calculated from three values of (i) the total signal change value of the standard data sets (step 1), (ii) the signal value of the reference cycle of the standard data sets (step 1), and (iii) the reference total signal change value (step 2) and were shown in Table 13.

TABLE 13

| Hardware Adjustment | Instrument Number | A) Total Signal Change Value of Standard Data Sets (TSC) | B) Reference Total Signal Change Value (R-TSC) | C) Ratio of TSC To R-TSC [A/B] | D) Signal Value at Reference Cycle of Standard Data Sets | E) Determined Reference Value [D/C] |
| --- | --- | --- | --- | --- | --- | --- |
| − | 1 | 2538 | 4560 | 0.5566 | 2964 | 5325 |
|   | 2 | 4808 | 4560 | 1.0545 | 5706 | 5411 |
|   | 3 | 8414 | 4560 | 1.8453 | 9994 | 5416 |
| + | 1 | 3513 | 4560 | 0.7705 | 4034 | 5236 |
|   | 2 | 5470 | 4560 | 1.1995 | 6260 | 5218 |
|   | 3 | 4601 | 4560 | 1.0090 | 5380 | 5332 |

<Step 4>

The six groups of the $1^{st}$ calibrated data sets prepared using the Instrument Blank signal Subtraction (IBS) in Example <2-2> were calibrated through the same method as described in Example <2-3-1> using the reference value determined in the above step 3 and resulted in the six groups of the $2^{nd}$ calibrated data sets.

Figure 10A:
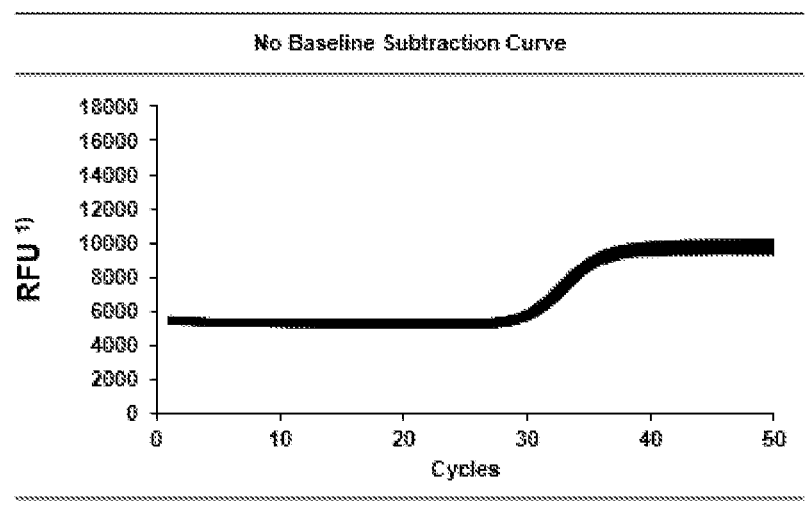
FIG. 10a represents amplification curves of calibrated data sets obtained by calibration of three groups of raw data sets by the IBS-SBN using an instrument-specific reference value, wherein the raw data sets are obtained respectively from three instruments without a hardware adjustment.

A. Analysis of the Results of Calibration of Data Sets Obtained from an Instrument without a Hardware Adjustment The data sets obtained from an instrument without a hardware adjustment were calibrated by the IBS-SBN using the instrument-specific reference value, and the resulting $2^{nd}$ calibrated data sets were analyzed. FIGS. 10A and 10B show the amplification curves (FIG. 10A) and the intra- and inter-instrument coefficients of variations (FIG. 10B) for the $2^{nd}$ calibrated data sets which were provided by subtracting the instrument blank signals from the data sets obtained from the instrument without a hardware adjustment and then calibrating them through the steps 1 to 4. The amplification curves were obtained by plotting the $2^{nd}$ calibrated data sets. FIG. 10A shows the amplification curves provided by plotting the $2^{nd}$ calibrated data sets without baseline subtraction (No Baseline Subtraction Curve), in which the intensities of the signals in the background and amplification regions can be compared. As a result of analysis, it was verified that the signal values at $5^{th}$ cycle of the data sets from the respective three instruments were calibrated into RFU 5325, 5411, and 5416 (i.e., the instrument-specific reference values), respectively and thus the signals in the background region became similar to one another and the signals in the amplification region also became similar to one another.

In addition, the baseline subtracted amplification curves were obtained by subtracting the baseline from the $2^{th}$ calibrated data sets and plotting the baseline subtracted data sets, and then the coefficient of variation at the $50^{th}$ cycle was calculated. In FIG. 10B representing the baseline subtracted amplification curve (Baseline Subtracted Curve), the signal variations in the amplification region were compared. The coefficients of variations of the amplification signals were analyzed. The intra-instrument coefficients of variations were 1.1%, 1.3% and 0.8%, respectively and the inter-instrument coefficient of variation of the amplification signals was 1.1%.

The following three coefficients of variations were compared and analyzed: (i) the coefficient of variation of the signals in the data sets obtained from the instrument without a hardware adjustment in Example <1-2>; (ii) the coefficient of variation of the signals in the data sets obtained from the instrument with a hardware adjustment in Example <1-3>; and (iii) the coefficient of variation of the signals in the $2^{nd}$ calibrated data sets provided by calibrating the data sets with IBS-SBN using the instrument-specific reference value of this Example, in which the data sets had been obtained from the instrument without a hardware adjustment.

As shown in Table 14, the $2^{nd}$ calibrated data sets provided by calibrating the data sets with the IBS-SBN using the instrument-specific reference value, wherein the data sets had been obtained from the instrument without a hardware adjustment, have following characteristics: When compared with the data sets obtained from the instrument without a hardware adjustment, (i) the intra-instrument coefficient of variation of the amplification signals was reduced by more than a half; and (ii) the inter-instrument coefficient of variation of the amplification signals was remarkably reduced by 48.2 P % (percentage points). In addition, when compared with the data sets obtained from the instrument with a hardware adjustment, (i) the intra-instrument coefficient of variation of the amplification signals was reduced by more than a half; and (ii) the inter-instrument coefficient of variation of the amplification signals was reduced by 16.6 P % (percentage points).

It would be demonstrated that the present method of calibrating the data sets using the IBS-SBN can effectively reduce the inter-instrument signal variations and the inter-well signal variations within an instrument even by adjusting the instrument-specific reference values using the instrument-specific standard data sets.

When compared to the method using the SBN of Example <1-4>, the calibration method using the IBS-SBN with the instrument-specific reference value is more effective in reducing the signal variations between the instruments and between the wells within an instrument.

TABLE 14

| Calibration Method | IBS-SBN Using Instrument-Specific Reference Value | – | – | + |
|---|---|---|---|---|
| | Hardware Adjustment | – | + | – |
| Results of Analysis of Amplification Signal (Coefficient of Variation, CV %) | Instrument 1 | 5.2 | 5.3 | 1.1 |
| | Instrument 2 | 9.1 | 7.8 | 1.3 |
| | Instrument 3 | 4.5 | 5.5 | 0.8 |
| | Total | 49.3 | 17.7 | 1.1 |

Figure 11A:
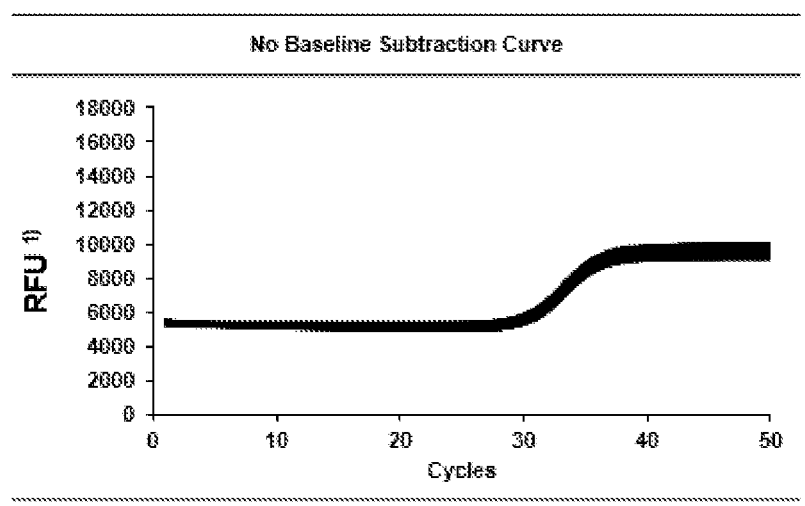
FIG. 11a represents amplification curves of calibrated data sets obtained by calibration of three groups of raw data sets by the IBS-SBN using an instrument-specific reference value, wherein the raw data sets are obtained respectively from three instruments with a hardware adjustment.

B. Analysis of the Results of Calibration of Data Sets Obtained from an Instrument with a Hardware Adjustment The data sets obtained from an instrument with a hardware adjustment were further calibrated by the IBS-SBN with the instrument-specific reference value and resulted in the $2^{nd}$ calibrated data sets. The resulting $2^{nd}$ calibrated data sets were analyzed. FIGS. 11A and 11B show the amplification the amplification curves (FIG. 11A) and the intra- and inter-instrument coefficients of variations (FIG. 11B) for the $2^{nd}$ calibrated data sets which were provided by subtracting the instrument blank signals from the data sets obtained from the instrument with a hardware adjustment and then calibrating them through the steps 1 to 4. The amplification curves were obtained by plotting the $2^{nd}$ calibrated data sets. FIG. 11A shows the amplification curves without baseline subtraction (No Baseline Subtraction Curve) for the $2^{nd}$ calibrated data sets, in which the signal intensities in the background and amplification regions can be compared. As a result of analysis, it was verified that the signal values at $5^{th}$ cycle of the data sets from the respective three instruments were calibrated into RFU 5236, 5218, and 5332, (i.e. the instrument-specific reference values), respectively and thus the signals in the background region became similar to one another and the signals in the amplification region also became similar to one another.

In addition, the baseline subtracted amplification curves (Baseline Subtracted Curve) were obtained by subtracting the baseline from the $2^{nd}$ calibrated data sets and by plotting the baseline subtracted data sets, and then the coefficient of variation at the $50^{th}$ cycle was calculated. In FIG. 11B representing the amplification curves with baseline subtraction, the signal variations in the amplification region were compared. The coefficients of variations of the amplification signals were analyzed. The intra-instrument coefficients of variations of the amplification signals were 1.2%, 1.7% and 1.0% respectively and the inter-instrument coefficient of variation of the amplification signals was 1.3%.

The following three coefficients of variations were compared and analyzed: (i) the coefficient of variation of the signals in the data sets obtained from the instrument without a hardware adjustment in Example <1-2>; (ii) the coefficient of variation of the signals in the data sets obtained from the instrument with a hardware adjustment in Example <1-3>; and (iii) the coefficient of variation of the signals in the $2^{nd}$ calibrated data sets provided by calibrating the data sets with the IBS-SBN using the instrument-specific reference value, wherein the data sets had been obtained from the instrument with a hardware adjustment.

As shown in Table 15, the $2^{nd}$ calibrated data sets provided by calibrating the data sets with the IBS-SBN using the instrument-specific reference value, wherein the data sets had been obtained from the instrument with a hardware adjustment, have following characteristics: When compared with the data sets obtained from the instrument without a hardware adjustment, (i) the intra-instrument coefficient of variation of the amplification signals was reduced by more than a half; and (ii) the inter-instrument coefficient of variation of the amplification signals was remarkably reduced by 48 P % (percentage points). In addition, when compared with the data sets obtained from the instrument with a hardware adjustment, (i) the intra-instrument coefficient of variation of the amplification signals was reduced by more than a half; and (ii) the inter-instrument coefficient of variation of the amplification signals was remarkably reduced by 16.4 P % (percentage points).

It would be demonstrated that the present method of calibrating the data sets using the IBS-SBN can effectively reduce the inter-instrument signal variations and the inter-well signal variations within an instrument even by adjusting the instrument-specific reference values using the instrument-specific standard data set. In particular, it would be understood that the additional calibration effects on the data set can be accomplished when the data set obtained from a the instrument with a hardware adjustment was further normalized by the IBS-SBN with the instrument-specific reference value.

When compared to the method using the SBN of Example <1-4> (see Table 8), the method of the IBS-SBN using the instrument-specific reference value has more excellent effects than the method of the SBN using the instrument-specific reference value in terms of an additional calibration effects on the instrument with a hardware adjustment.

TABLE 15

| Calibration Method | | IBS-SBN Using Instrument-Specific Reference Value | – | – | + |
|---|---|---|---|---|---|
| | | Hardware Adjustment | – | + | – |
| Results of Analysis of Amplification Signal (Coefficient of Variation, CV %) | Instrument 1 | | 5.2 | 5.3 | 1.2 |
| | Instrument 2 | | 9.1 | 7.8 | 1.7 |
| | Instrument 3 | | 4.5 | 5.5 | 1.0 |
| | Total | | 49.3 | 17.7 | 1.3 |

The present method of calibrating the signals of a real-time PCR instrument using the IBS-SBN can be used to reduce the intra- and inter-instrument signal variations with easy and software access and has a superior calibration effect to the method using the SBN.

When the SBN or IBS-SBN is used, the cycle intended to be normalized (i.e., reference cycle) can be designated within the signal generating region as well as the background region in which the indicated signal is not generated. This means that the normalization method itself has signal calibration effects and there is a difference only in the calibration level according to the reference cycle depending on the position of reference cycle. The melting signal variations in the melting curve analysis were calibrated by utilizing the above mentioned characteristics of the present method in the following Example 3.

Example 3: Calibration and Analysis of the Melting Data Set by Using Instrument Blank Signal Subtraction and Specific Background Signal Based Normalization (IBS-SBN)

In the above Examples 1 and 2, the nucleic add amplification data sets were calibrated using the SBN or IBS-SBN. In Example 3, it is investigated whether the melting data sets can be calibrated software-wise by the present method.

The melting signal variations in the following three groups of data sets were compared and analyzed: (i) a group of melting data sets obtained from an instrument without a hardware adjustment; (ii) a group of melting data sets obtained from an instrument with a hardware adjustment; and (ii) a group of calibrated melting data sets obtained by calibrating the melting data sets software-wise using the IBS-SBN.

<3-1> Preparation of Melting Data Sets

A melting analysis for a target nucleic add molecule was performed using a PTOCE assay as a signal-generating means with 50 cycles of an amplification in the six CFX96™ Real-Time PCR Detection Systems (Bio-Rad) listed in Table 16. The target nucleic add molecule was a DNA of Human beta-globin. The interactive dual label was provided by CTO labeled with a reporter molecule (Quasar 670) and a quencher molecule (BHQ-1) (dual-labeled CTO).

The reaction was conducted in the tube containing a target nucleic add molecule, a downstream primer, an upstream primer, dual-labeled CTO, PTO and Master Mix containing $MgCl_2$, dNTPs and Taq DNA polymerase. The tube containing the reaction mixture was placed in the real-time thermocycler (CFX96, Bio-Rad). The reaction mixture was denatured for 15 min at 95° C. and subjected to 50 cycles of 30 sec at 95° C., 60 sec at 60° C., 30 sec at 72° C. The melting data sets were obtained by detecting temperature dependent fluorescent signals while the real-time PCR products were heated from 55° C. to 85° C. by 0.5° C.

The 96 reactions on the respective 96-wells were carried out under the same condition in the respective instruments using the samples containing the same target nucleic add of the same concentration. By analyzing the melting data sets obtained from the above reactions, the level of the intra- and inter-instrument melting signal variations and the level of the reduction in melting signal variations made by the present method were analyzed.

A total six groups of raw melting data sets consisting of the fluorescence value (RFU) per temperature were prepared by using a total six PCR Instruments consisting of three instruments without a hardware adjustment and the other three instruments with a hardware adjustment. Each group includes 96-data sets obtained from 96-well reactions.

The derivatives of the raw melting data sets were calculated as the negative derivatives from the raw melting data sets. In order to calculate the derivatives, the Least Square Method was applied to the raw melting data sets according to the following equation and the derivatives of the raw melting data sets were obtained as the negative derivatives.

$$s_i = -\frac{\sum_{i=I-a}^{I+b}(x_i - \bar{x})(y_i - \bar{y})}{\sum_{i=I-a}^{I+b}(x_i - \bar{x})^2}$$

$$\bar{x} = \frac{\sum_{i=I-a}^{I+b} x_i}{n}, \bar{y} = \frac{\sum_{i=I-a}^{I+b} y_i}{n}$$

I: a cycle number of data sets of which derivatives are to be calculated $x_i$: a cycle number of $i^{th}$ cycle $y_i$: a signal intensity measured at $i^{th}$ cycle si the amount of data change at $i^{th}$ cycle "a" and "b": an integer from 0 to 10 n: a+b+1, a number of data used to calculate derivatives $\bar{x}$: a mean value of cycle numbers from "I–a" to "I+b"

$\bar{y}$: a mean value of signal intensities measured at cycles from "I–a" to "I+b"

In Examples, "1" is used for "a" and "b". For data points at which "I–a" is less than "1", the "a" may be altered to permit "I–a" to become "1". For data points at which "I+b" is more than the number of all data points, the "b" may be altered to permit "I+b" to be equal to the number of all data points.

The melting curves were obtained by plotting the raw melting data sets and the melting derivative curves (melting peaks) were obtained by plotting the derivatives of the raw melting data sets.

TABLE 16

| Name of Instruments | Hardware adjustment | Real-time PCR Instrument |
|---|---|---|
| Instrument 1 | No adjustment | CFX96 Real-time Cycler (Bio-Rad) |
| Instrument 2 | | |
| Instrument 3 | | |
| Instrument 4 | Adjustment | |
| Instrument 5 | | |
| Instrument 6 | | |

<3-2> Analysis of Melting Data Set Obtained from Instrument without Hardware Adjustment The raw melting data sets and their derivatives obtained in Example <3-1> were used. The signal variations were analyzed in three groups of raw melting data sets obtained from the instruments without a hardware adjustment and in three groups of the derivatives of the raw melting data sets.

Figure 12A:
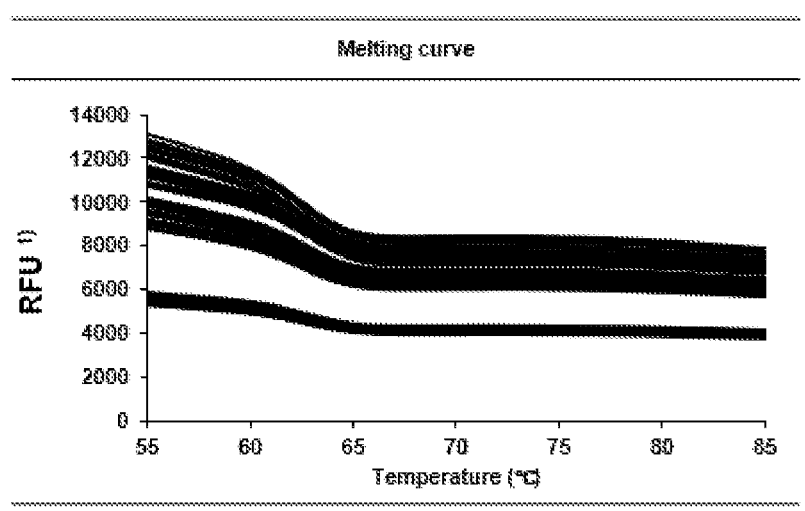
FIG. 12a represents melting curves of three groups of raw melting data sets obtained respectively from three instruments without a hardware adjustment.

The melting curves were obtained by plotting the raw melting data sets in order to identify the overall melting signal patterns of three instruments (FIG. 12A).

As a result of analyzing the melting curves, as shown in FIG. 12A, the signals between the instruments were divided each other, which is unlike to the theoretical expectation that the same value of derivatives will be plotted for amplification reactions under the same condition. In addition, it was observed that there was a signal difference between the reactions performed in the differently located wells within the identical instrument.

In order to compare signal variations in the melting curve analysis, the melting derivative curves (melting peaks) were prepared by plotting the derivatives of the raw melting data sets which were obtained from the respective three instruments. The variation of the melting peak is the variation of the derivatives of the melting data set.

The point at which the value (slope) of the melting peak was maximized was designated as an analytical temperature and the coefficient of variation of the value of the melting peak at the analytical temperature were calculated.

The coefficient of variation of the melting peak i.e., the coefficient of variation of derivative of the melting data set is the coefficient of variation of the value of melting peaks at the analytical temperature. The method of calculating the coefficient of variation is described in Example <1-2>.

The coefficient of variation of the melting peak was represented in FIG. 12B. The intra-instrument coefficients of variations of the melting peaks were analyzed as 4.9%, 5.9%, and 7.5%, respectively and the inter-instrument coefficient of variation of the melting peaks was analyzed as 37.8%.

<3-3> Analysis of Melting Data Set Obtained from Instrument with Hardware Adjustment The signal variations were analyzed by the same method as described in Example <3-2> between three groups of the raw melting data sets obtained from the instrument with a hardware adjustment in Example <3-1> and three groups of the derivatives of the raw melting data sets.

Figure 13A:
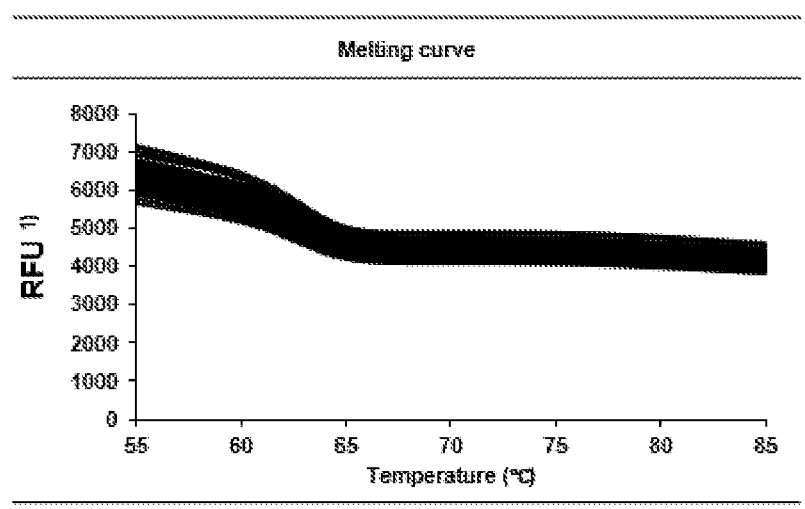
FIG. 13a represents melting curves of three groups of raw melting data sets obtained respectively from three instruments with a hardware adjustment.

The melting curves were analyzed according to the same method as described in Example <3-2>. As shown in FIG. 13A, it was revealed that the inter-instrument signal variations were reduced compared to the melting data sets obtained from the instrument without a hardware adjustment. However, there still remained widely distributed signal variations between the instruments and between the reactions.

Figure 13B:
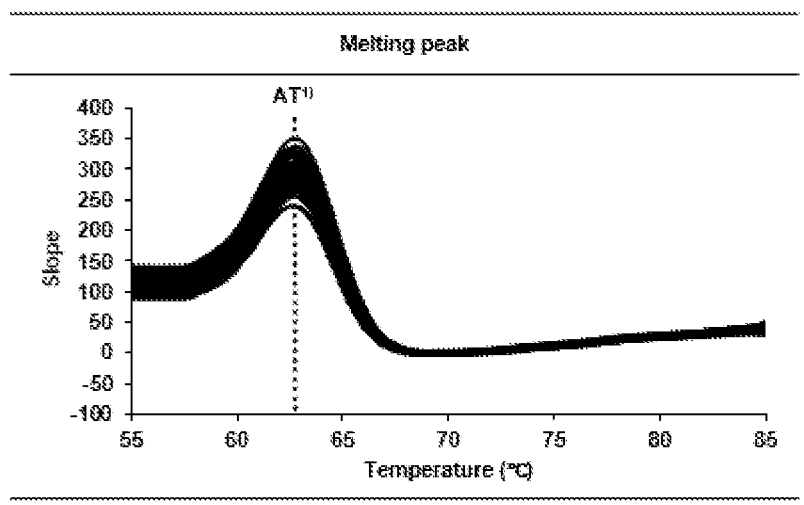
FIG. 13b represents melting peaks obtained by plotting the derivatives of the raw melting data sets obtained respectively from three instruments with a hardware adjustment and analytical results of the inter- and the intra-instrument coefficient of variation of maximum derivatives of the data sets.

The coefficient of variation of the melting derivative curves (melting peaks) was calculated according to the same method as described in Example <3-2>. As shown in FIG. 13B, it was revealed that the intra-instrument coefficient of variations of the melting peaks analyzed as 5.8%, 8.3%, and 7.9%, respectively and the inter-instrument coefficient of variation of the melting peaks was analyzed as 7.5%.

When the above results were compared with the results of the melting data sets obtained from the instrument without a hardware adjustment in Example <3-2>, it was proved that the inter-instrument coefficient of variation of the melting peaks was reduced by 30.3 P % (percentage points) while there was negligent difference in the intra-instrument coefficient of variation of the melting peak.

From the above results, it can be concluded that even though the calibration induced by the hardware adjustment can reduce partly the inter-instrument coefficient of variation of the melting peak, a considerable level of signal variations between the instruments still exists and the coefficient of variation of the melting peak between the wells within a single instrument cannot be reduced by the hardware adjustment.

<3-4> Analysis of Melting Data Set Software Calibrated Using IBS-SBN

<3-4-1> Instrument Blank Signal Measurement

The instrument blank signal can be measured according to the same method as described in Example <2-1>.

Because the signals are detected at various temperatures in the melting analysis, it is possible to measure separate instrument blank signals at various temperatures and to apply each measured instrument blank signal according to the respective temperatures.

In this example, the instrument blank signal was measured at the single temperature and the signal value at $10^{th}$ cycle of the data sets was used as the instrument blank signal, in which the data sets were obtained by performing 10 cycles of amplification using an empty tube under the same real-time PCR reaction condition as described in Example <2-1>. The instrument blank signals were measured respectively as in Table 17.

TABLE 17

| Name | Instrument Blank Signal of Instrument without Hardware Adjustment | Name | Instrument Blank Signal of Instrument with Hardware Adjustment |
|---|---|---|---|
| Instrument 1 | RFU 1480 | Instrument 4 | RFU 1517 |
| Instrument 2 | RFU 1847 | Instrument 5 | RFU 1680 |
| Instrument 3 | RFU 1700 | Instrument 6 | RFU 1418 |

<3-4-2> Preparation of the $1^{st}$ Calibrated Melting Data Set by Instrument Blank signal Subtraction (IBS)

The $1^{st}$ calibrated melting data sets were obtained by subtracting the instrument blank signal in Example <3-4-1> from the raw melting data sets in Example <3-1> as following equation.

$1^{st}$ Calibrated Melting Data Set=Raw Data Set −Instrument Blank Signal

By the calculation using the above equation, a total of six groups of $1^{st}$ calibrated melting data sets were provided, which includes three groups of the $1^{st}$ calibrated melting data sets obtained by using the raw melting data set obtained from the instrument without a hardware adjustment and the other three groups of the $1^{st}$ calibrated melting data sets obtained by using the raw melting data set obtained from the instrument with a hardware adjustment.

<3-4-3> Calibration of $1^{st}$ Calibrated Melting Data Set by SBN and Analysis of Calibrated Melting Data Set The signals were calibrated by Specific Background signal-based Normalization (SBN) according to the same method as described in the <2-3>.

<3-4-3-1> Calibration of $1^{st}$ Calibrated Melting Data Set Using SBN Applied with Common Reference Value In this Example, the sib groups of $1^{st}$ calibrated melting data sets obtained in Example <3-4-2> were software-wise calibrated using the SBN according to the following steps. A single reference value was applied to the melting data sets obtained from all of the instruments.

<Step 1>

In order to apply the SBN to the melting curve analysis in which the unit of the cycle is the temperature, the point intended to be normalized, in other words, the specific temperature of the melting data sets is designated as the reference temperature i.e., the reference cycle. In this example, the melting data sets were calibrated with the reference temperatures of 55° C. and 85° C. and the results were compared each other.

<Step 2>

A reference value is designated for the normalization with the specific signal. In this example, when the reference temperature was 55° C., the reference value was designated as RFU 4,900, and when the reference temperature was 85° C., the reference value was designated as RFU 2,700.

<Step 3>

A normalization coefficient is calculated from the signal value corresponding to the reference temperature in the $1^{st}$ calibrated melting data sets and the reference value provided in the step 2.

Normalization coeffcient=Signal Value at Reference Temperature÷Reference Value

<Step 4>

The signal values at all temperatures are calibrated using the normalization coefficient.

$2^{nd}$ Calibrated Signal Value(RFU)=Signal Value of $1^{st}$ Calibrated Melting Data Set(RFU)÷Normalization Coefficient.

The six groups of the $2^{nd}$ calibrated melting data sets were obtained by calibrating the six groups of the $1^{st}$ calibrated melting data sets prepared from the <3-4-2> according to the steps 1 to 4.

A. Analysis of the Results of Calibration of Melting Data Sets Obtained from an Instrument without a Hardware Adjustment The melting data sets obtained from the instrument without a hardware adjustment were calibrated by the IBS-SBN and resulted in the $2^{nd}$ calibrated melting data sets. The obtained $2^{nd}$ calibrated melting data sets were analyzed.

Figure 14A:
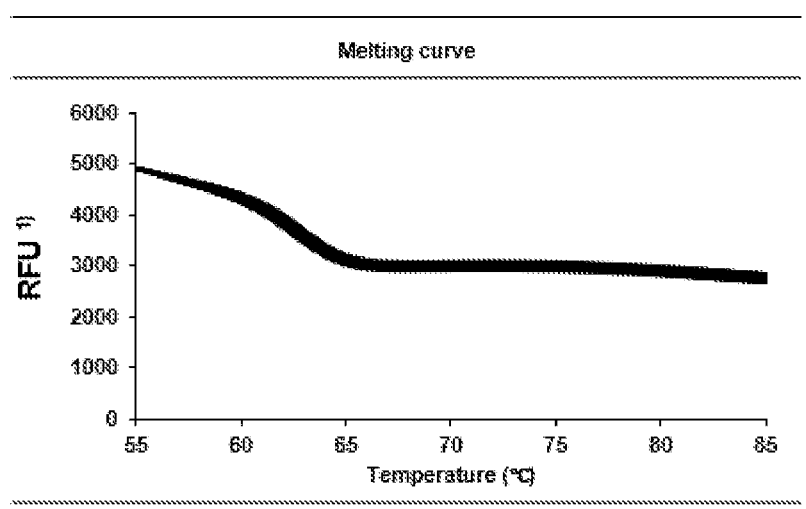
FIG. 14a represents melting curves of calibrated melting data sets obtained by calibration of three groups of raw melting data sets by the IBS-SBN using a common reference value and a reference temperature of 55° C. as a reference cycle, wherein the raw melting data sets are obtained respectively from three instruments without a hardware adjustment.
Figure 14B:
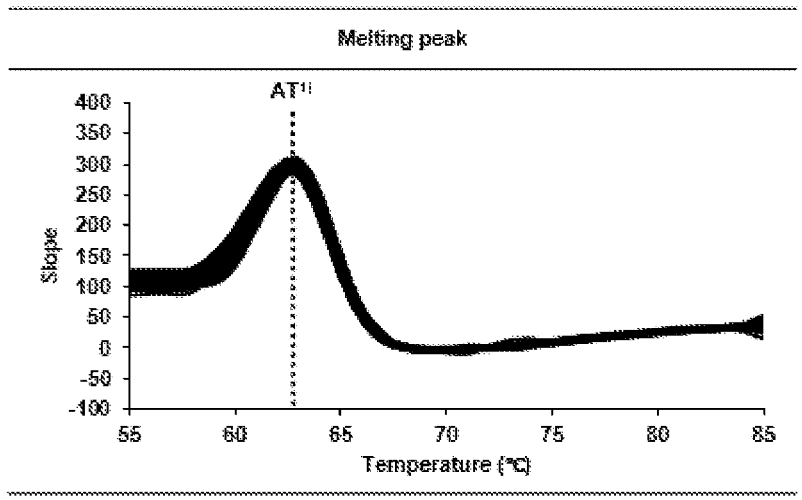
FIG. 14b represents melting peaks obtained by plotting the derivatives of the calibrated melting data sets obtained by calibration of three groups of raw melting data sets by the IBS-SBN using a common reference value and a reference temperature of 55° C. as a reference cycle, wherein the raw melting data sets are obtained respectively from three instruments without a hardware adjustment and analytical results of the inter- and the intra-instrument coefficient of variation of maximum derivatives of the data sets.
Figure 14C:
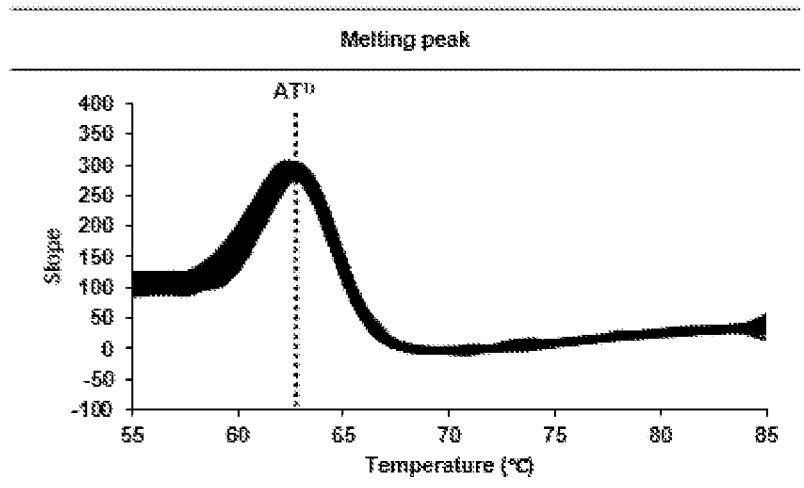
FIG. 14c represents melting peaks obtained by plotting the derivatives of the calibrated melting data sets obtained by calibration of three groups of raw melting data sets by the IBS-SBN using a common reference value and a reference temperature of 85° C. as a reference cycle, wherein the raw melting data sets are obtained respectively from three instruments without a hardware adjustment and analytical results of the inter- and the intra-instrument coefficient of variation of maximum derivatives of the data sets.

FIGS. 14A, 14B and 14C show the amplification curves (FIG. 14A) and the intra- and inter-instrument coefficients of variations (FIGS. 14B and 14C) for the $2^{nd}$ calibrated melting data sets which were provided by subtracting the instrument blank signals from the melting data sets obtained from the instrument without a hardware adjustment and then calibrating them through the steps 1 to 4.

The melting curves were obtained by plotting the $2^{nd}$ calibrated melting data sets. FIG. 14A shows melting curves provided by plotting the $2^{nd}$ calibrated melting data sets without baseline subtraction, in which the intensities of the melting signals can be compared. As a result of analysis, it was verified that the inter-instrument signal variations were remarkably reduced when the signals were calibrated using the IBS-SBN at the reference temperature of 55° C. In particular, all of the RFUs at the reference temperature of 55° C. were identical with the reference value designated, addressing that there is no signal variation.

In addition, the derivatives of raw melting data sets were obtained from the $2^{nd}$ calibrated melting data sets, the melting derivative curves (melting peaks) were obtained by plotting the derivatives of raw melting data sets and the coefficient of variation at the reference temperature of 55° C. or 85° C. was calculated.

FIG. 14B shows the melting peaks of the $2^{nd}$ calibrated melting data sets which were calibrated with the reference temperature of 55° C. The coefficients of variations of the melting peaks (i.e., the coefficients of variations of derivatives of the melting data sets) were analyzed. The intra-instrument coefficients of variations of the melting peaks were 1.8%, 1.1%, and 1.8% respectively and the inter-instrument coefficient of variation of the melting peaks was 1.8%.

FIG. 14C shows the melting peak of the $2^{nd}$ calibrated melting data sets which were calibrated with the reference temperature of 85°. The coefficients of variations of the melting peaks were analyzed. The intra-instrument coefficients of variations of the melting peaks were 1.5%, 1.9%, and 2.5% respectively and the inter-instrument coefficient of variation of the melting peaks was 2.3%.

The following three coefficients of variations were compared and analyzed: (i) the coefficient of variation of the melting peaks calculated from the derivatives of the melting data sets obtained from the instrument without a hardware adjustment in Example <3-2>; (ii) the coefficient of variation of the melting peaks calculated from the derivatives of the melting data sets obtained from the instrument with a hardware adjustment in Example <3-3>; and (iii) the coefficient of variation of the melting peaks calculated from the derivatives of the $2^{nd}$ calibrated melting data sets provided by calibrating the melting data sets with the IBS-SBN, wherein the melting data sets had been obtained from the instrument without a hardware adjustment.

As shown in Table 18, The $2^{nd}$ calibrated melting data sets provided by calibrating the melting data sets with the IBS-SBN, wherein the melting data sets had been obtained from the instrument without a hardware adjustment, have following characteristics: When compared with the melting data sets obtained from the instrument without a hardware adjustment, (i) the intra-instrument coefficient of variation of the melting peak was reduced by more than a half; and (ii) the inter-instrument coefficients of variations of the melting peaks at the respective reference temperatures of 55° C. and 85° C. were remarkably reduced by 36.0 P % (percentage points) and 35.5 P % (percentage points) respectively. In addition, when compared with the melting data sets obtained from the instrument with a hardware adjustment, (i) the intra-instrument coefficient of variation of the melting peak was reduced by more than a half, and (ii) the inter-instrument coefficients of variations of the melting peaks at the respective reference temperatures of 55° C. and 85° C. were remarkably reduced by 5.7 P % (percentage points) and 5.2 P % (percentage points) respectively.

It would be demonstrated that the present method of calibrating the data sets using the IBS-SBN can effectively reduce the inter- and intra-instrument variations of the derivatives of the raw melting data sets. In particular, it would be understood that the IBS-SBN have more excellent calibration effects than methods of adjusting a hardware of an instrument, addressing that a melting signal calibration effect better than that of the hardware adjustment can be successfully accomplished by using only the IBS-SBN without a hardware adjustment of an instrument.

When the results according to the reference temperature (reference cycle) were compared, it was analyzed that there was little difference in the reduction rate of the variations of the derivative of the raw melting data sets according to the reference temperature and it was also analyzed that the coefficient of variation of the derivative of the raw melting data sets was reduced irrespective of the reference temperature. Accordingly, the experiments in the following examples were performed under the reference temperature of 55° C.

TABLE 18

| Calibration Method | Instrument Blank Signal Subtraction and Specific Background-signal based Normalization (IBS-SBN) | – | – | + (55° C.) | + (85° C.) |
|---|---|---|---|---|---|
| | Hardware Adjustment | – | + | – | – |
| Results of Analysis of Melting Signal (Coefficient of Variation, CV %) | Instrument 1 | 4.9 | 5.8 | 1.8 | 1.5 |
| | Instrument 2 | 5.9 | 8.3 | 1.1 | 1.9 |
| | Instrument 3 | 7.5 | 7.9 | 1.8 | 2.5 |
| | Total | 37.8 | 7.5 | 1.8 | 2.3 |

B. Analysis of the Results of Calibration of Melting Data Sets Obtained from an Instrument with a Hardware Adjustment The melting data sets obtained from the instrument with a hardware adjustment were further calibrated by the IBS-SBN through the steps 1 to 4 and resulted in the $2^{nd}$ calibrated melting data sets. The $2^{nd}$ calibrated melting data sets were analyzed.

Figure 15A:
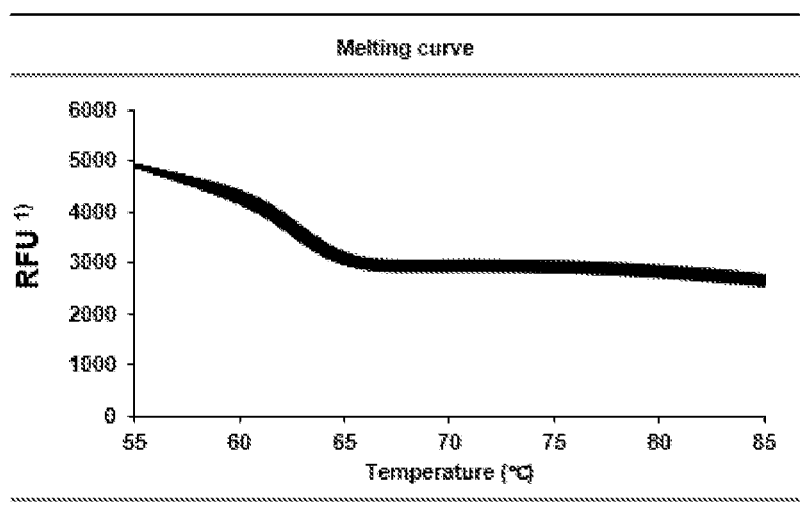
FIG. 15a represents melting curves of calibrated melting data sets obtained by calibration of three groups of raw melting data sets by the IBS-SBN using a common reference value and a reference temperature of 55° C. as a reference cycle, wherein the raw melting data sets are obtained respectively from three instruments with a hardware adjustment.

FIG. 15A shows the melting curves of the $2^{nd}$ calibrated melting data sets which were provided by subtracting the instrument blank signal from the melting data sets obtained from the instrument with a hardware adjustment and then calibrating the subtracted melting data sets through the steps 1 to 4.

Figure 15B:
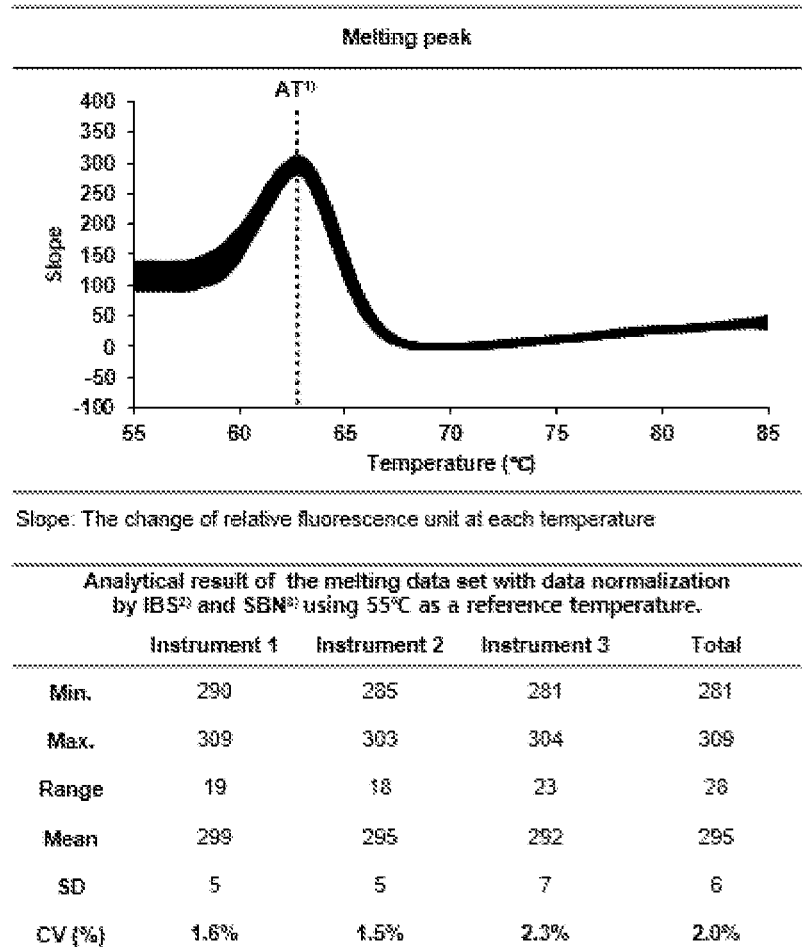
FIG. 15b represents melting peaks obtained by plotting the derivatives of the calibrated melting data sets obtained by calibration of three groups of raw melting data sets by the IBS-SBN using a common reference value and a reference temperature of 55° C. as a reference cycle, wherein the raw melting data sets are obtained respectively from three instruments with a hardware adjustment and analytical results of the inter- and the intra-instrument coefficient of variation of maximum derivatives of the data sets.

FIG. 15B shows the intra- and inter-instrument coefficients of variations obtained from the melting peaks of the derivatives of the raw melting data sets for the $2^{nd}$ calibrated melting data sets.

The melting curves were obtained by plotting the $2^{nd}$ calibrated melting data sets. FIG. 15A shows the melting curves provided by plotting the $2^{nd}$ calibrated melting data sets without baseline subtraction, in which the intensities of the melting signals can be compared with each other. As represented in FIG. 15A, the inter-instrument signal variations were highly reduced by the signal calibration using the IBS-SBN at the reference temperature of 55° C. In particular, all of the RFUs at the reference temperature of 55° C. were identical with the reference value designated, addressing that there is no signal variation.

In addition, the derivatives of the raw melting data sets were obtained from the $2^{nd}$ calibrated melting data set, the melting derivative curves (melting peaks) were obtained by plotting the derivatives of the raw melting data sets, and the coefficient of variation at the reference temperature of 55° C. was calculated.

FIG. 15B represents the melting peaks of the $2^{nd}$ calibrated melting data sets which were calibrated with the reference temperature of 55° C. The coefficient of variation of the melting peaks (i.e., the coefficient of variation of a derivative of the melting data set) were analyzed. The intra-instrument coefficients of variations of the melting peaks were 1.6%, 1.5% and 2.3% respectively and the inter-instrument coefficient of variation of the melting peak was 2.0%.

The following three coefficients of variations were compared and analyzed: (i) the coefficient of variation of the melting peaks calculated from the derivatives of the melting data sets obtained from the instrument without a hardware adjustment in Example <3-2>; (ii) the coefficient of variation of the melting peaks calculated from the derivatives of the melting data sets obtained from the instrument with a hardware adjustment in Example <3-3>; and (iii) the coefficient of variation of the melting peaks calculated from the derivatives of the $2^{nd}$ calibrated melting data sets provided by calibrating the melting data sets with IBS-SBN, wherein the melting data sets had been obtained from the instrument with a hardware adjustment.

As shown in Table 19, the $2^{nd}$ calibrated melting data sets provided by calibrating the melting data sets with the IBS-SBN, wherein the melting data sets had been obtained from the instrument with a hardware adjustment, have following characteristics: when compared with the melting data sets obtained from the instrument without a hardware adjustment, (i) the intra-instrument coefficient of variation of the melting peaks was reduced by more than a half; and (ii) the inter-instrument coefficient of variation of the melting peaks at the reference temperature of 55° C. was remarkably reduced by 35.8 P % (percentage points). In addition, when compared with the melting data set obtained from the instrument with a hardware adjustment, (i) the intra-instrument coefficient of variation of the melting peaks was reduced by more than a half; and (ii) the inter-instrument coefficient of variation of the melting peaks at the reference temperature of 55° C. was remarkably reduced by 5.5 P % (percentage points).

It would be demonstrated that the present method of signal calibration using the IBS-SBN can reduce the inter- and intra-instrument variations of the derivatives of the raw melting data sets. In particular, it would be understood that the additional calibration effects on the melting data sets can be accomplished when the melting data sets obtained from the instrument with a hardware adjustment is further normalized by the IBS-SBN of the present invention.

TABLE 19

| Calibration Method | Instrument Blank Signal Subtraction and Specific-Background signal based Normalization (IBS-SBN) | – | – | + (55° C.) |
|---|---|---|---|---|
| | Hardware Adjustment | – | + | – |
| Results of Analysis of Melting Signal (Coefficient of Variation, CV %) | Instrument 1 | 4.9 | 5.8 | 1.6 |
| | Instrument 2 | 5.9 | 8.3 | 1.5 |
| | Instrument 3 | 7.5 | 7.9 | 2.3 |
| | Total | 37.8 | 7.5 | 2.0 |

<3-4-2-2> Calibration of 1st Calibrated Melting Data Set by SBN Using Instrument-Specific Reference Value Determined Based on Total Signal Change Value The instrument-specific reference value was determined with consideration for inter-instrument variations and the melting data set was calibrated using the determined instrument-specific reference value. The standard data sets were obtained using the target analyte of standard concentration as described in Example <2-3-2>. It was investigated whether the method using the instrument-specific reference value could be also applied to the melting curve analysis.

<Step 1>

The instrument-specific standard melting data set was obtained by performing a standard signal-generating process using a target analyte of standard concentration under the same reaction condition as that of the practical signal-generating process performed for obtaining melting data sets from a real experimental sample in the respective instruments. A signal value and a total signal change value to determine a reference value were obtained from the standard data set.

Because the temperature of 55° C. was designated as a reference temperature (the reference cycle) in Example, the melting signal value at 55° C. of the standard melting data sets was designated as the signal value for use in determination of the reference value.

In order to calculate the total signal change value of the standard melting data sets, the 1st calibrated melting data sets were provided using the obtained standard melting data sets according to the same method as described in Example <3-4-2> and the derivatives of the melting data sets were obtained according to the same method as described in Example <3-1>. The total signal change value was calculated from the derivative of the melting data sets. The maximum value of the derivatives of the melting data sets (i.e., the maximum value of the melting peaks) was designated as the total signal change value.

In this Example, three standard melting data sets were obtained from each instrument and the total signal change values of the respective melting data sets and the signal value to be used for determining the reference value were calculated. Specifically, the mean of the three total signal change values calculated from three instrument-specific standard melting data sets was designated as the total signal change value of the relevant instrument. The mean of the three signal values at the reference cycle (reference temperature) calculated from three instrument-specific standard melting data sets was designated as the signal value to be used for determining the reference value of the relevant instrument.

The total signal change values (TSCs) and the signal values used for determining the reference values of the standard melting data sets obtained from the instruments 1, 2, and 3 without or with a hardware adjustment were measured as shown in Table 20.

TABLE 20

| Number of Instrument | Hardware Adjustment | TSC of the Standard Melting Data Sets (Slope) | Signal Value of Reference Cycle of Standard Melting Data Sets (Signal Value Used for Determining Reference Value) (RFU) |
|---|---|---|---|
| Instrument 1 | − | 234 | 3786 |
| Instrument 2 | − | 467 | 7787 |
| Instrument 3 | − | 572 | 9431 |
| Instrument 4 | + | 305 | 4961 |
| Instrument 5 | + | 257 | 4246 |
| Instrument 6 | + | 274 | 4539 |

<Step 2>

The reference total signal change value (R-TSC) used for determining the instrument-specific reference value together with the calculated total signal change value, was designated. In this example, the value of slope 300 which is similar to the mean of the total signal change values of the data sets obtained from three instrument with a hardware adjustment of Example <3-1>, was designated as the reference total signal change value (see FIG. 13B).

<Step 3>

The reference values to be applied to the respective instruments were calculated using the following equation from the three values of (i) the total signal change value of the standard melting data sets (step 1), (ii) the signal value at the reference temperature (the reference cycle) of the standard melting data sets (step 1), and (ii) the reference total signal change value (step 2):

Reference Value=Signal Value at Reference Cycle of Standard Melting Data Set÷(Total Signal Change Value of the Standard Melting Data Set/Reference Total Signal Change Value)

Upon analyzing the standard melting data sets obtained from the respective instruments, the reference values to be used for calibrating the data sets obtained from the instruments 1, 2, and 3 with or without a hardware adjustment were determined as shown in Table 21.

TABLE 21

| Hardware Adjustment | Instrument Number | A) Total Signal Change Value of Standard Melting Data Sets (TSC) (Unit: Slope) | B) Reference Total Signal Change Value (R-TSC) | C) Ratio of TSC To R-TSC [A/B] | D) Signal, Value at Reference Cycle of Standard Melting Data Sets (Unit: RFU) | E) Determined Reference Value [D/C] |
|---|---|---|---|---|---|---|
| − | 1 | 234 | 300 | 0.7800 | 3786 | 4854 |
|   | 2 | 467 | 300 | 1.5556 | 7787 | 5006 |
|   | 3 | 572 | 300 | 1.9078 | 9431 | 4943 |

TABLE 21-continued

| Hardware Adjustment | Instrument Number | A) Total Signal Change Value of Standard Melting Data Sets (TSC) (Unit: Slope) | B) Reference Total Signal Change Value (R-TSC) | C) Ratio of TSC To R-TSC [A/B] | D) Signal, Value at Reference Cycle of Standard Melting Data Sets (Unit: RFU) | E) Determined Reference Value [D/C] |
|---|---|---|---|---|---|---|
| + | 4 | 305 | 300 | 1.0178 | 4961 | 4875 |
|  | 5 | 257 | 300 | 0.8556 | 4246 | 4963 |
|  | 6 | 274 | 300 | 0.9144 | 4539 | 4963 |

<Step 4>

The six groups of the $1^{st}$ calibrated melting data sets prepared in Example <3-4-2> were calibrated through the same method as described in Example <3-4-3-1> using the instrument-specific reference value determined in the above step 3 and resulted in the six groups of the $2^{nd}$ calibrated melting data sets.

Figure 16A:
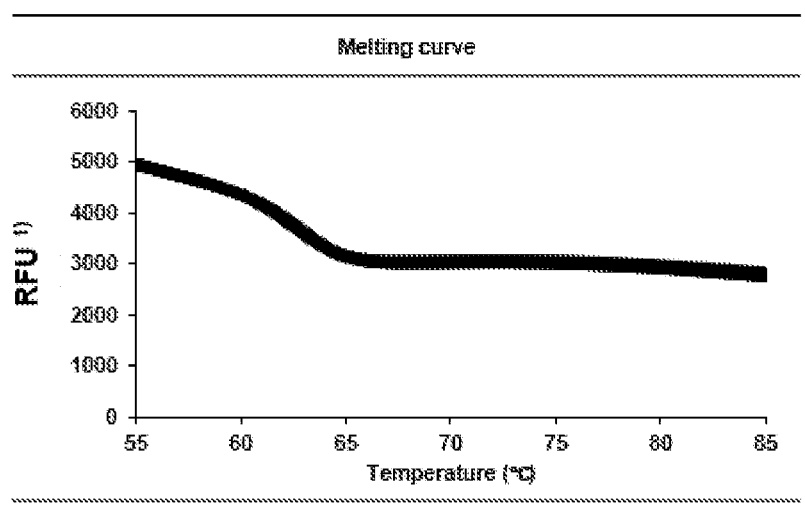
FIG. 16a represents melting curves of calibrated melting data sets obtained by calibration of three groups of raw melting data sets by the IBS-SBN using an instrument-specific reference value and a reference temperature of 55° C. as a reference cycle, wherein the raw melting data sets are obtained respectively from three instruments without a hardware adjustment.
Figure 16B:
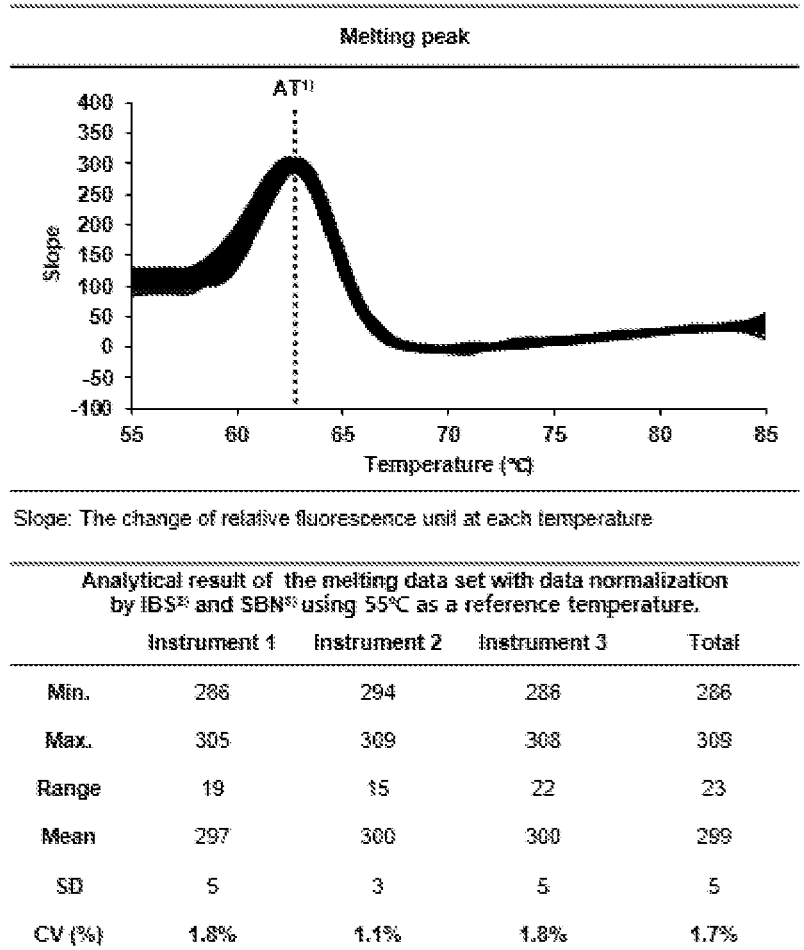
FIG. 16b represents melting peaks obtained by plotting the derivatives of the calibrated melting data sets obtained by calibration of three groups of raw melting data sets by the IBS-SBN using an instrument-specific reference value and a reference temperature of 55° C. as a reference cycle, wherein the raw melting data sets are obtained respectively from three instruments without a hardware adjustment and analytical results of the inter- and the intra-instrument coefficient of variation of maximum derivatives of the data sets.

A. Analysis of the Results of Calibration of Melting Data Sets Obtained from an Instrument without a Hardware Adjustment The melting data sets obtained from an instrument without a hardware adjustment were calibrated by the IBS-SBN using the instrument-specific reference value and resulted in the $2^{nd}$ calibrated melting data sets. The obtained $2^{nd}$ calibrated data sets were analyzed. FIG. 16A shows the melting curves for the results of calibrating the melting data sets obtained from the instrument without a hardware adjustment through the above steps 1 to 4. FIG. 16B shows the intra- and inter-instrument coefficients of variations obtained from the melting peaks for the results of calibrating the melting data sets obtained from the instrument without a hardware adjustment through the above steps 1 to 4. The melting curves were obtained by plotting the $2^{nd}$ calibrated melting data sets provided by calibrating the raw melting data sets using the IBS-SBN with the instrument-specific reference value, in which the raw melting data sets had been obtained from the instrument without a hardware adjustment.

FIG. 16A shows the melting curves obtained by plotting the $2^{nd}$ calibrated melting data sets without baseline subtraction, in which the intensities of the melting signals can be compared. The signal values at the reference temperature of 55° C. of the melting data sets of three instruments were calibrated into the instrument-specific reference values of RFU 4854, 5006, and 4943, respectively and thus the melting signals became similar to one another.

The derivatives of the raw melting data sets were obtained from the $2^{nd}$ calibrated melting data sets, the melting derivative curves (melting peaks) were obtained by plotting the derivative of the raw melting data sets, and the coefficient of variation at the reference temperature of 55° C. was calculated from the melting derivative curves.

FIG. 16B shows the melting peaks of the $2^{nd}$ calibrated melting data sets which were calibrated with the reference temperature of 55° C. The coefficients of variations of the melting peaks (i.e., the coefficients of variations of derivatives of the melting data sets) were analyzed. The intra-instrument coefficients of variations of the melting peaks were 1.8%, 1.1%, and 1.8% respectively and the inter-instrument coefficient of variation of the melting peaks was 1.7%.

The following three coefficients of variations were compared and analyzed: (i) the coefficient of variation of the melting peaks calculated from the derivatives of the melting data sets obtained from the instrument without a hardware adjustment in Example <3-2>; (ii) the coefficient of variation of the melting peaks calculated from the derivatives of the melting data sets obtained from the instrument with a hardware adjustment in Example <3-3>; and (iii) the coefficient of variation of the melting peaks of the derivatives of the $2^{nd}$ calibrated melting data sets provided by calibrating the melting data sets by the IBS-SBN using the instrument-specific reference value, wherein the melting data sets had been obtained from the instrument with a hardware adjustment.

As shown in Table 22, the $2^{nd}$ calibrated melting data sets provided by calibrating the melting data sets by the IBS-SBN using the instrument-specific reference value, wherein the melting data sets had been obtained from the instrument without a hardware adjustment, have following characteristics: When compared with the melting data sets obtained from the instrument without a hardware adjustment, (i) the intra-instrument coefficient of variation of the melting peak was reduced by more than a half; and (ii) the inter-instrument coefficient of variation of the melting peak was remarkably reduced by 36.1 P % (percentage points). In addition, when compared with the melting data sets obtained from the instrument with a hardware adjustment, (i) the intra-instrument coefficient of variation of the melting peak was reduced by more than a half; and (ii) the inter-instrument coefficient of variation of the derivative was remarkably reduced by 5.8 P % (percentage points).

It would be demonstrated that the present method of adjusting the instrument-specific reference value using the instrument-specific standard melting data set can effectively reduce the intra- and inter-instrument signal variations of the melting data sets in which the temperature corresponds to the cycle, addressing that a melting signal calibration effect better than that of the hardware calibration can be successfully accomplished by using only the IBS-SBN with the reference value determined by the signal total change value without a hardware adjustment of the instrument.

TABLE 22

| Calibration Method | IBS-SBN Applied with Instrument-Specific Reference Value | − | − | + |

TABLE 22-continued

|  | Hardware Adjustment | − | + | − |
|---|---|---|---|---|
| Results of Analysis of Melting Signal (Coefficient of Variation, CV %) | Instrument 1 | 4.9 | 5.8 | 1.8 |
|  | Instrument 2 | 5.9 | 8.3 | 1.1 |
|  | Instrument 3 | 7.5 | 7.9 | 1.8 |
|  | Total | 37.8 | 7.5 | 1.7 |

Figure 17A:
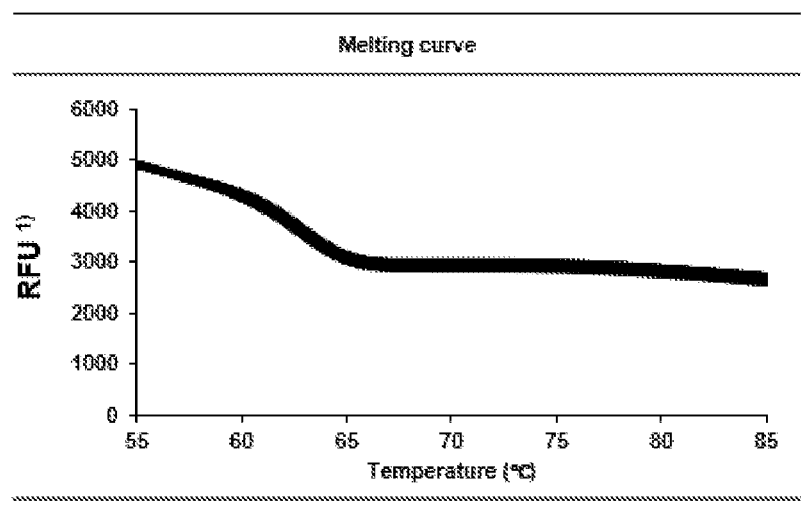
FIG. 17a represents melting curves of calibrated melting data sets obtained by calibration of three groups of raw melting data sets by the IBS-SBN using an instrument-specific reference value and a reference temperature of 55° C. as a reference cycle, wherein the raw melting data sets are obtained respectively from three instruments with a hardware adjustment.
Figure 17B:
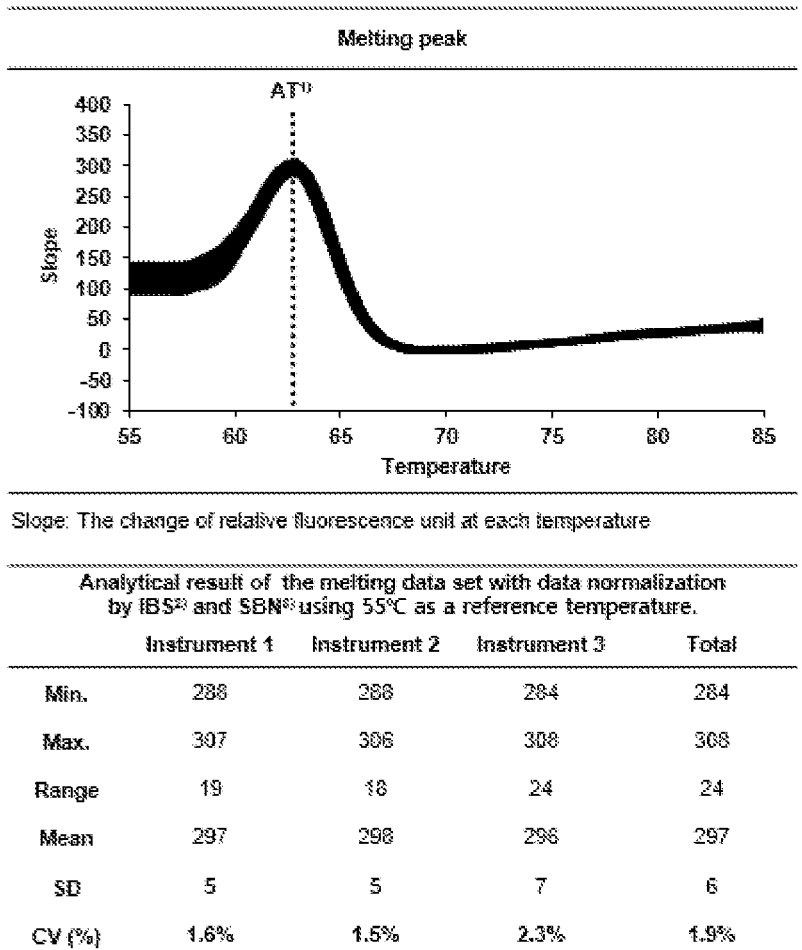
FIG. 17b represents melting peaks obtained by plotting the derivatives of the calibrated melting data sets obtained by calibration of three groups of raw melting data sets by the IBS-SBN using an instrument-specific reference value and a reference temperature of 55° C. as a reference cycle, wherein the raw melting data sets are obtained respectively from three instruments with a hardware adjustment and analytical results of the inter- and the intra-instrument coefficient of variation of maximum derivatives of the data sets.

B. Analysis of the Results of Calibration of Melting Data Sets Obtained from an instrument with a Hardware Adjustment The melting data sets obtained from an instrument with a hardware adjustment were further calibrated by the IBS-SBN with the instrument-specific reference value and resulted in the $2^{nd}$ calibrated melting data sets. The obtained $2^{nd}$ calibrated melting data sets were analyzed. FIG. 17A shows the melting curves for the results of calibrating the melting data sets obtained from the instrument with a hardware adjustment through the above steps 1 to 4. FIG. 17B shows the intra- and inter-instrument coefficients of variations of the melting peaks for the results of calibrating the melting data sets obtained from the instrument with a hardware adjustment through the above steps 1 to 4. The melting curves were obtained by plotting the $2^{nd}$ calibrated melting data sets provided by calibrating the raw melting data sets using the IBS-SBN with the instrument-specific reference value, in which the raw melting data sets had been obtained from the instrument with a hardware adjustment.

FIG. 17A shows the melting curves obtained by plotting the $2^{nd}$ calibrated melting data sets without baseline subtraction, in which the intensities of the melting signals can be compared. The signal values at the reference temperature of 55° C. of the melting data sets of the respective three instruments were calibrated into the instrument-specific reference values of RFU 4875, 4963 and 4963, respectively and thus the melting signals became similar to one another.

The derivatives of the raw melting data sets were obtained from the $2^{nd}$ calibrated melting data sets, the melting derivative curves (melting peaks) were obtained by plotting the derivatives of the raw melting data sets, and the coefficient of variation at the reference temperature of 55° C. was calculated from the melting derivative peaks.

FIG. 17B shows the melting peak of the $2^{nd}$ calibrated melting data sets which were calibrated with the reference temperature of 55° C. The coefficients of variations of the melting peaks (i.e., the coefficients of variations of derivative of the melting data sets) were analyzed. The intra-instrument coefficients of variations of the melting peaks were 1.6%, 1.5%, and 2.3% respectively and the inter-instrument coefficient of variation of the melting peak was 1.9%.

The following three coefficients of variations were compared and analyzed: (i) the coefficient of variation of the melting peaks calculated from the derivatives of the melting data sets obtained from the instrument without a hardware adjustment in Example <3-2>; (ii) the coefficient of variation of the melting peaks calculated from the derivatives of the melting data sets obtained from the instrument with a hardware adjustment in Example <3-3>; and (iii) the coefficient of variation of the melting peaks calculated from the derivatives of the $2^{nd}$ calibrated melting data sets provided by calibrating the melting data sets by the IBS-SBN using the instrument-specific reference value, wherein the melting data sets had been obtained from the instrument with a hardware adjustment.

As shown in Table 23, the $2^{nd}$ calibrated melting data sets provided by calibrating the melting data sets by the IBS-SBN using the instrument-specific reference value, wherein the melting data sets had been obtained from the instrument with a hardware adjustment, have following characteristics: When compared with the melting data sets obtained from the instrument without a hardware adjustment, (i) the intra-instrument coefficient of variation of the melting peaks was reduced by more than a half; and (ii) the inter-instrument coefficient of variation (CV) of the melting peaks was remarkably reduced by 35.9 P % (percentage points). In addition, when compared with the melting data sets obtained from the instrument with a hardware adjustment, (i) the intra-instrument coefficient of variation of the melting peaks was reduced by more than a half; and (ii) the inter-instrument coefficient of variation of the melting peaks was remarkably reduced by 5.6 P % (percentage points).

It would be demonstrated that a more accurate calibration effect can be accomplished when the melting data sets obtained from the instrument with a hardware adjustment are further normalized by the IBS-SBN using the reference value determined by the signal total change value.

TABLE 23

| Calibration Method | IBS-SBN Applied with Instrument Specific Reference Value | − | − | + |
|---|---|---|---|---|
|  | Hardware Adjustment | − | + | − |
| Results of Analysis of Melting Signal | Instrument 1 | 4.9 | 5.8 | 1.6 |
|  | Instrument 2 | 5.9 | 8.3 | 1.5 |
|  | Instrument 3 | 7.5 | 7.9 | 2.3 |
| (Coefficient of Variation, CV %) | Total | 37.8 | 7.5 | 1.9 |

Accordingly, the present method of a signal calibration using the IBS-SBN is also applicable to the calibration of the melting signals as well as amplification signals with the same effect. Because the melting curve analysis requires fine control of the temperature for the detection of signals, there is a higher possibility of the inter-instrument signal variations in the melting curve analysis compared to the amplification curve analysis. Therefore, it is expected that the signal calibration method of the invention will be more useful in the melting curve analysis.

Example 4: The Control of the Signal Intensity of the Data Set by Using Instrument Blank Signal Subtraction and Specific Background Signal Based Normalization (IBS-SBN)

It was investigated in Example 4 whether the signal intensity control as well as the signal calibration can be made in the data sets by using the Instrument Blank Signal Subtraction and Specific Background Signal Based Normalization (IBS-SBN) and whether the concentration of materials used as signal generation means (e.g., TaqMan probe) can be decreased by the control of the signal intensity of the data sets.

First, the data sets were obtained through a real-time PCR as to the target nucleic add molecule by using a low concentration of a TaqMan probe and then the $2^{nd}$ calibrated data sets were obtained by calibrating them using the IBS-SBN applied with the various reference values. The $2^{nd}$ calibrated data sets were analyzed by comparing with the data sets which had been obtained through a real-time PCR as to the target nucleic acid molecule using various practical concentrations of TaqMan probes.

Furthermore, it was also investigated whether the change of the signal variations between the instruments in the data sets was generated when the data sets were calibrated using the IBS-SBN applied with various reference values.

<4-1> Comparison of the Data Sets Calibrated Using the IBS-SBN with the Concentration-Specific Data Sets A real-time PCR for the target nucleic add molecule was performed using a TaqMan probe as the signal-generating means with 50 cycles of an amplification in the CFX96™ Real-Time PCR Detection System (Bio-Rad).

Four raw data sets were obtained using a single instrument with various TaqMan probe concentrations of 1 pmole, 2 pmole, 3 pmole, and 5 pmole per reaction.

The concentration-specific baseline subtracted data sets (Group A) were calculated from the raw data sets through the same method as described in Example <1-1>.

The three $2^{nd}$ calibrated data sets were provided by calibrating the data sets obtained using 1 pmole of a TaqMan probe according to the method described in Example 2, in which three $2^{nd}$ calibrated data sets have the signal values similar to those of the respective data sets obtained using 2 pmole, 3 pmole and 5 pmole.

Specifically, the instrument blank signal used was measured by the same method as described in Example <2-1>. The instrument blank signal was measured as RFU 3466. The $1^{st}$ calibrated data set was obtained by subtracting the instrument blank signal of RFU 3466 from the data set obtained using 1 pmole of a TaqMan probe.

The three $2^{nd}$ calibrated data sets were provided by designating the $5^{th}$ cycle of the $1^{st}$ calibrated data sets as the reference cycle and also designating RFU 2,700, 4,100, and 5,900 as the reference values respectively so that the signal intensities similar to those of the TaqMan probe concentration-specific data sets were detected. The baseline subtracted data sets (Group B) were calculated from the $2^{nd}$ calibrated data sets according to the method described in Example <1-1>.

The data sets of Groups A and B were compared and analyzed by plotting them.

First, the signal values of the Groups A and B at the last cycle (i.e., $50^{th}$ cycle) were compared in order to compare the signal intensities of the data sets.

Figure 18:
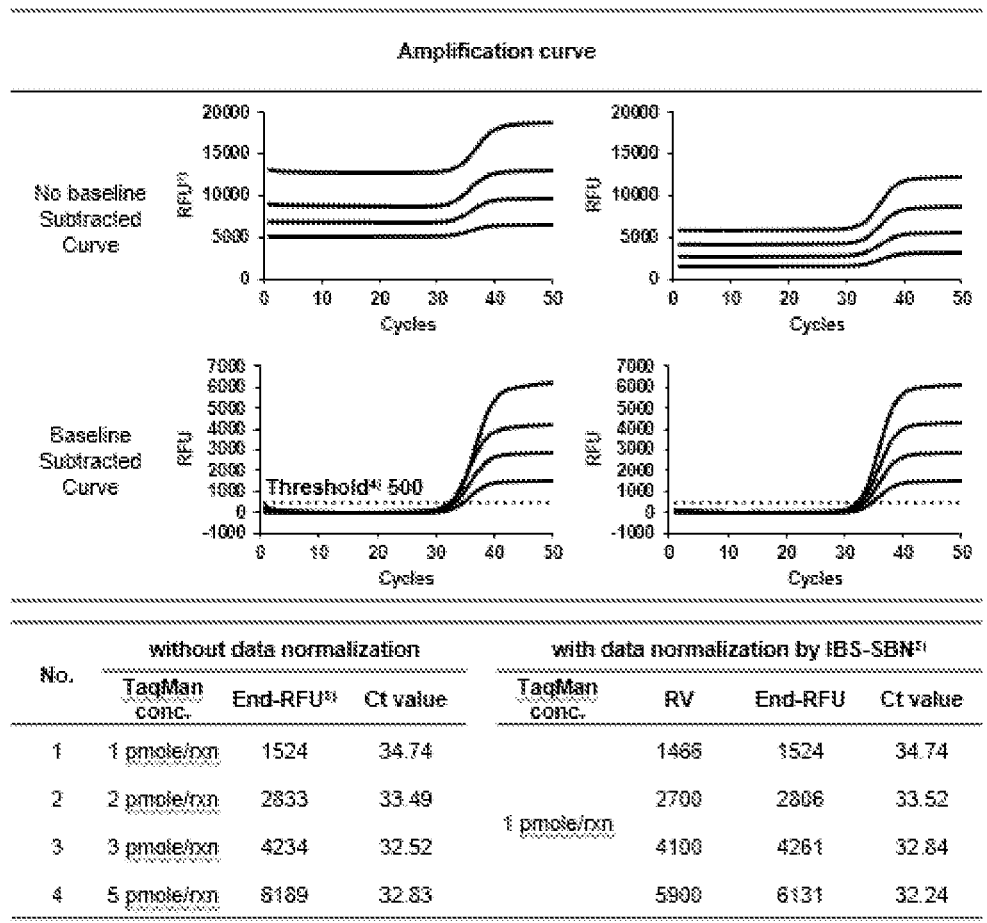
FIG. 18 represents a comparative result of data sets obtained using probes of various concentrations and calibrated data sets obtained by the IBS-SBN using various reference values.

As a result, as shown in FIG. 18, the pattern of the increase in the signal intensity of the data sets of Group A induced by the increase of the TaqMan probe concentration is similar to the pattern of the increase in the signal intensity of the data sets of Group B induced by the change of the reference value using the IBS-SBN.

Second, the Ct (threshold cycle) values of the respective data sets of Groups A and B were analyzed in order to compare the difference in the time to detect the target between the data sets in Groups A and B. The Ct value was set as the cycle value corresponding to the threshold value of RFU 500.

As shown in FIG. 18, the Ct values of the TaqMan probe concentration-specific data sets of Group A are similar to the Ct values of the reference value-specific data sets of Group B.

As demonstrated in the above, the signal intensity of the data sets can be controlled discretionally by the reference value change, which proves the fact that the signal intensity of the data sets can be adjusted software-wise without the hardware adjustment of the instrument or without increasing the concentration of the signal-generating materials (e.g., TaqMan probe).

It was investigated in Example <4-2> below whether there is a difference in the calibration effect on the signal variations when the signal intensity is controlled by the reference value change using the IBS-SBN.

<4-2> Confirmation of Coefficient of Variation of Calibrated Data Sets According to Control of Signal Intensity by IBS-SBN It was investigated whether a change in the signal variation (i.e., coefficient of variation) of the data sets was induced by the reference value control when the $2^{nd}$ calibrated data sets were obtained in which their intensities were controlled by the IBS-SBN method.

The $2^{nd}$ calibrated data sets were obtained by calibrating the $1^{st}$ calibrated data sets using the SBN with the reference values of RFU 5,000, 10,000, and 15,000 according to the same method as described in Example 2-3, in which the $1^{st}$ calibrated data sets had been obtained from three instruments without a hardware adjustment in Example <2-2>. After that, the amplification curve and the coefficient of variation were obtained through the same method as described in Example <1-2>. The $5^{th}$ cycle was designated as reference cycle. The results were shown in Table 24.

TABLE 24

| | RV | | | | | | | | |
|---|---|---|---|---|---|---|---|---|---|
| | 5000 | | | 10000 | | | 15000 | | |
| | Instrument | | | | | | | | |
| | 1 | 2 | 3 | 1 | 2 | 3 | 1 | 2 | 3 |
| | Intra-Instrument | | | | | | | | |
| Min. | 4176 | 4124 | 4158 | 8352 | 8248 | 8317 | 12527 | 12372 | 12475 |
| Max. | 4418 | 4364 | 4328 | 8836 | 8728 | 8655 | 13254 | 13093 | 12983 |
| Range | 242 | 240 | 169 | 484 | 481 | 338 | 726 | 721 | 508 |
| Mean | 4299 | 4233 | 4242 | 8599 | 8467 | 8484 | 12898 | 12700 | 12726 |
| SD | 49 | 54 | 36 | 98 | 108 | 71 | 147 | 162 | 107 |
| CV (%) | 1.10% | 1.30% | 0.80% | 1.10% | 1.30% | 0.80% | 1.10% | 1.30% | 0.80% |
| | Inter-Instrument | | | | | | | | |
| Min. | | 4124 | | | 8248 | | | 12372 | |
| Max. | | 4418 | | | 8836 | | | 13254 | |

TABLE 24-continued

| | RV | | | | | | | | |
|---|---|---|---|---|---|---|---|---|---|
| | 5000 | | | 10000 | | | 15000 | | |
| | | | | Instrument | | | | | |
| | 1 | 2 | 3 | 1 | 2 | 3 | 1 | 2 | 3 |
| Range | | 294 | | | 588 | | | 882 | |
| Mean | | 4258 | | | 8517 | | | 12775 | |
| SD | | 55 | | | 110 | | | 166 | |
| CV (%) | | 1.30% | | | 1.30% | | | 1.30% | |

Min.: Minimum;
Max.: Maximum;
Range: Max-Min;
SD: Standard Deviation;
CV: Coefficient of variation As shown in Table 24, even though the maximum signal, the minimum signal, the range, the mean value, and the standard deviation of the respective instruments were changed according to the change of the reference value, the coefficients of variations which correspond to the intra-instrument and inter-instrument signal variations had the same value irrespective of the change of the reference value.

As demonstrated in the above, since the software adjustment of the signal intensity in the data sets can be successfully accomplished by the reference value change using the IBS-SBN, there is no need of a hardware adjustment on the instrument or no need to control the concentration of the signal-generating materials (e.g., TaqMan probe) in order to increase the signal intensity. It is expected that the method of the invention has the effect of a reducing a production cost of the materials for a calibration, time for a calibration, and a cost for a production of signal-generating materials. The method of the invention has the usefulness in view of that the signal variations of the data sets can be calibrated software-wise at the same time.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for reducing inter- and intra-instrument signal variations of a data set of a target analyte in a sample comprising:
   (a) providing a normalization coefficient for calibrating the data set by using a reference value, a reference cycle and the data set;
      wherein the data set is obtained from a signal-generating process for the target analyte using a signal-generating means; wherein the signal-generating process is a polymerase chain reaction (PCR) or a real-time polymerase chain reaction (real-time PCR); wherein the data set comprises a plurality of data points comprising cycles of the signal-generating process and signal values at the cycles;
      wherein step (a) comprises the following steps:
      performing PCR or real-time PCR on the sample;
      obtaining the data set via by the PCR or real-time PCR;
      selecting the reference cycle from the cycles of the data set; and
      determining a signal value at the reference cycle;
      wherein the reference value is a value arbitrarily determined from a real number except zero;
      providing the normalization coefficient by defining a relationship between the reference value and a signal value at a cycle of the data set corresponding to the reference cycle;
      wherein the relationship between the signal value at the cycle of the data set corresponding to the reference cycle and the reference value is a difference between the signal value at the cycle of the data set corresponding to the reference cycle and the reference value; and
   (b) providing a calibrated data set by obtaining calibrated signal values by applying the normalization coefficient to the signal values of the data set.

2. The method according to claim 1, wherein the data set of the target analyte has information indicating the presence or absence of the target analyte in the sample.

3. The method according to claim 1, wherein the signal-generating process generates signals in a manner dependent on the presence of the target analyte in the sample.

4. The method according to claim 1, wherein the target analyte is a target nucleic acid molecule.

5. The method according to claim 4, wherein the signal-generating process comprises performing an amplification of the target nucleic acid molecule.

6. The method according to claim 1, wherein the signal-generating process is a polymerase chain reaction (PCR) or a real-time PCR.

7. The method according to claim 1, wherein step (a) further comprises removing an instrument blank signal from the data set.

8. The method according to claim 1, wherein the reference cycle comprises at least two reference cycles.

9. The method according to claim 1, wherein the process amplifying the signal values comprises providing signal values of a background signal region and a signal amplification region; wherein the reference cycle is selected within the background signal region.

10. The method according to claim 9, wherein the signal-generating process is PCR or real-time PCR, and the reference cycle is selected within a background signal region before a signal amplification region of the PCR or the real-time PCR.

11. The method according to claim 1, wherein the signal-generating process comprises a plurality of signal-generating processes performed in different reaction vessels; wherein the data set comprises a plurality of data sets obtained from the plurality of signal-generating processes.

12. The method according to claim 11, wherein the method further comprises a step of calibrating the plurality of data sets by using an identical reference value.

13. The method according to claim 11, wherein at least two data sets of the plurality of data sets are calibrated by using different reference values from each other.

14. The method according to claim 11, wherein the method further comprises a step of calibrating the plurality of data sets by using an identical reference cycle.

15. The method according to claim 11, wherein the method comprises performing the plurality of the signal-generating processes on different instruments from each other.

16. The method according to claim 11, wherein the method comprises determining the reference value within the average ±standard deviation of signal values at cycles of the plurality of data sets corresponding to the reference cycle.

17. The method according to claim 1,
wherein the method comprises determining the reference value by (i) a ratio of a total signal change value of a standard data set to a reference total signal change value; wherein the standard data set is obtained by using a reaction site which is identical to that used for obtaining the data set from the signal-generating process for the target analyte; and
wherein the method further comprises determining the reference total signal change value by one or more data sets comprising a data set obtained from a signal-generating process using a reaction site which is different from that used for obtaining the data set from the signal-generating process for the target analyte and (ii) the standard data set.

18. The method according to claim 1, wherein the difference between the signal value at the cycle of the data set corresponding to the reference cycle and the reference value is a ratio of the signal value at the cycle of the data set corresponding to the reference cycle to the reference value.

19. The method according to claim 1, wherein the method comprises using the calibrated data set for qualitative detection of the target analyte in the sample.

20. The method according to claim 1, wherein the method comprises obtaining the calibrated signal value the following mathematical equation 1:

Calibrated signal value=signal value/normalization coefficient.

21. The method according to claim 1, wherein the method further comprises the following step before the step (a): performing the signal-generating process to obtain a data set of the target analyte in the sample.

22. The method according to claim 1, the method comprises using the calibrated data set for quantitative detection of the target analyte in the sample.

23. A non-transitory computer-readable storage medium containing instructions to configure a processor to perform a method for reducing inter-and intra-instrument signal variations of a data set of a target analyte in a sample, the method comprising:
(a) providing a normalization coefficient for calibrating the data set by using a reference value, a reference cycle and the data set;
wherein the data set is obtained from a signal-generating process for the target analyte using a signal-generating means; wherein the signal-generating process is a polymerase chain reaction (PCR) or a real-time polymerase chain reaction (real-time PCR); wherein the data set comprises a plurality of data points comprising cycles of the signal-generating process and signal values at the cycles;
wherein step (a) comprises the following steps:
performing PCR or real-time PCR on the sample;
obtaining the data set via by the PCR or real-time PCR;
selecting the reference cycle from the cycles of the data set; and
determining a signal value at the reference cycle;
wherein the reference value is a value arbitrarily determined from a real number except zero;
providing the normalization coefficient by defining a relationship between the reference value and a signal value at a cycle of the data set corresponding to the reference cycle;
wherein the relationship between the signal value at the cycle of the data set corresponding to the reference cycle and the reference value is a difference between the signal value at the cycle of the data set corresponding to the reference cycle and the reference value; and
(b) providing a calibrated data set by obtaining calibrated signal values by applying the normalization coefficient to the signal values of the data set.

24. A device for performing an analysis method for calibrating a data set of a target analyte in a sample, comprising (a) a computer processor and (b) the computer-readable storage medium of claim 23 coupled to the computer processor.

* * * * *